(12) United States Patent
Bach et al.

(10) Patent No.: US 11,602,293 B2
(45) Date of Patent: Mar. 14, 2023

(54) IDENTIFYING AND STRENGTHENING PHYSIOLOGICAL/NEUROPHYSIOLOGICAL STATES PREDICTIVE OF SUPERIOR PERFORMANCE

(71) Applicant: Optios, Inc., San Diego, CA (US)

(72) Inventors: David Bach, San Diego, CA (US); Suhas Chelian, San Jose, CA (US); Paul Deguzman, Valley Cottage, NY (US); Jacek Dmochowski, Montclair, NJ (US); Amy Kruse, Annapolis, MD (US); Will McBurnett, Austin, TX (US); Steven L. Miller, Pacifica, CA (US); Thomas F. Nugent, III, Riva, MD (US); Paul Sajda, New York, NY (US)

(73) Assignee: Optios, Inc., San Diego, CA (US)

( * ) Notice: Subject to any disclaimer, the term of this patent is extended or adjusted under 35 U.S.C. 154(b) by 817 days.

(21) Appl. No.: 16/504,098

(22) Filed: Jul. 5, 2019

(65) Prior Publication Data

US 2020/0008725 A1    Jan. 9, 2020

Related U.S. Application Data

(60) Provisional application No. 62/831,134, filed on Apr. 8, 2019, provisional application No. 62/798,922, filed (Continued)

(51) Int. Cl.
*A61B 5/16* (2006.01)
*A61B 5/369* (2021.01)

(52) U.S. Cl.
CPC .............. *A61B 5/165* (2013.01); *A61B 5/369* (2021.01); *A61B 2503/12* (2013.01)

(58) Field of Classification Search
None
See application file for complete search history.

(56) References Cited

U.S. PATENT DOCUMENTS

| | | | |
|---|---|---|---|
| 4,683,891 A * | 8/1987 | Cornellier | A61B 5/16 600/480 |
| 4,928,704 A | 5/1990 | Hardt | |

(Continued)

OTHER PUBLICATIONS

Alec Smith, et al., Irrational exuberance and neural crash warning signals during endogenous experimental market bubbles, Jul. 22, 2014, www.pnas.org, vol. 111, No. 29, pp. 10503-10508 (Year: 2014).*

(Continued)

*Primary Examiner* — Kirk W Hermann
(74) *Attorney, Agent, or Firm* — Miller Johnson

(57) ABSTRACT

To identify physiological states that are predictive of a person's performance, a system provides physiological and behavioral interfaces and a data processing pipeline. Physiological sensors generate physiological data about the person while performing a task. The behavioral interface generates performance data about the person while performing the task. The pipeline collects the physiological and performance data along with reference data from a population of people performing the same or similar tasks. In various implementations, the physiological states are brain states. In one implementation, the pipeline computes bandpower ratios. In another implementation, the pipeline decomposes the physiological data into frequency-banded components, identifies brain states derived from the decomposed data—for example, clusters of correlations of decomposed data envelopes—grades the performance data, compares the graded performance data to the brain states, and identifies statistical relationships between the brain states and levels of performance.

20 Claims, 33 Drawing Sheets

Related U.S. Application Data on Jan. 30, 2019, provisional application No. 62/793,171, filed on Jan. 16, 2019, provisional application No. 62/725,605, filed on Aug. 31, 2018, provisional application No. 62/725,626, filed on Aug. 31, 2018, provisional application No. 62/725,638, filed on Aug. 31, 2018, provisional application No. 62/725,535, filed on Aug. 31, 2018, provisional application No. 62/725,517, filed on Aug. 31, 2018, provisional application No. 62/725,590, filed on Aug. 31, 2018, provisional application No. 62/725,503, filed on Aug. 31, 2018, provisional application No. 62/725,567, filed on Aug. 31, 2018, provisional application No. 62/725,548, filed on Aug. 31, 2018, provisional application No. 62/724,660, filed on Aug. 30, 2018, provisional application No. 62/724,665, filed on Aug. 30, 2018, provisional application No. 62/711,668, filed on Jul. 30, 2018, provisional application No. 62/694,268, filed on Jul. 5, 2018.

(56) References Cited

U.S. PATENT DOCUMENTS

| | | | |
|---|---|---|---|
| 5,083,571 | A | 1/1992 | Prichep |
| 5,273,037 | A | 12/1993 | Itil et al. |
| 5,295,491 | A | 3/1994 | Gevins |
| 5,662,117 | A | 9/1997 | Bittman |
| 7,771,320 | B2 | 8/2010 | Riley et al. |
| 2004/0092809 | A1* | 5/2004 | DeCharms ............ A61B 5/0048 600/410 |
| 2005/0153268 | A1 | 7/2005 | Junkin et al. |
| 2009/0099623 | A1 | 4/2009 | Bentwich |
| 2010/0016677 | A1* | 1/2010 | Oetringer ............... A61B 5/165 600/300 |
| 2011/0105859 | A1* | 5/2011 | Popovic ............... A61B 5/0006 600/301 |
| 2012/0130266 | A1* | 5/2012 | Mathan ................. A61B 5/4833 600/544 |
| 2012/0143020 | A1 | 6/2012 | Bordoley et al. |
| 2014/0316230 | A1 | 10/2014 | Denison et al. |
| 2014/0323190 | A1 | 10/2014 | Hinman et al. |
| 2015/0050626 | A1 | 2/2015 | Tully |
| 2015/0199010 | A1 | 7/2015 | Coleman et al. |
| 2015/0216439 | A1 | 8/2015 | Muraskin et al. |
| 2016/0007899 | A1* | 1/2016 | Durkee .................. G09B 23/28 600/300 |
| 2016/0077547 | A1* | 3/2016 | Aimone ............... A61B 5/6814 345/8 |
| 2016/0180234 | A1* | 6/2016 | Siebach ................. G06N 5/048 705/321 |
| 2016/0235324 | A1* | 8/2016 | Mershin ............... A61B 5/6803 |
| 2016/0262703 | A1 | 9/2016 | Maccallum |
| 2017/0086729 | A1* | 3/2017 | Bruno ..................... A61B 5/16 |
| 2017/0109627 | A1 | 4/2017 | Sherwin et al. |
| 2017/0143228 | A1 | 5/2017 | Leuthardt, Jr. et al. |
| 2017/0229037 | A1 | 8/2017 | Gazzaley |

OTHER PUBLICATIONS

Shantipriya Parida and Satchidananda Dehuri, Applying Machine Learning Techniques for Cognitive State Classification, *International Conference in Distributed Computing & Internet Technology (ICDCIT—2013) Proceedings published in International Journal of Computer Applications® (IJCA)* (0975-8887).

Dylan Schmorrow and Amy Kruse, Augmenting This . . . Augmented That: Maximizing Human Performance, Conference Paper • Jan. 2004, ResearchGate.

Scott Makeig, et al., Evolving Signal Processing for Brain-Computer Interfaces, Proceedings of the IEEE | vol. 100, May 13, 2012.

Christian Jarrett, Caffeine causes widespread brain entropy (and that's a good thing), Research Digest, Brain, Intelligence Apr. 10, 2018May 1, 2018.

Joshua Poore and Andrea Webb, Uncertainty and Feedback-Related States in a Semi-Structured, Participant-Driven Task, Conference Paper, Apr. 2014, ResearchGate.

Vijayalakshmi, et al., Independent Component Analysis of EEG Signals and Real Time Data Acquisition Using MyDAQ and Labview, International Journal of Innovative Research in Advanced Engineering (IJIRAE) ISSN: 2349-2163 vol. 1 Issue 9 (Oct. 2014).

Ertugrul, et al., Encoding the Local Connectivity Patterns of fMRI for Cognitive State Classification, 1610.05036v1 [cs.Cv] Oct. 17, 2016.

Dorneich, et al., An Evaluation of Real-Time Cognitive State Classification in a Harsh Operational Environment, Proceedings of the Human Factors and Ergonomics Society, Baltimore, MD, Oct. 1-5.

Schlink, et al., Independent Component Analysis and Source Localization on Mobile EEG Data Can Identify Increased Levels of Acute Stress, Frontiers in Human Neuroscience, published: Jun. 16, 2017, doi: 10.3389/fnhum.2017.00310.

Fenton-O'Creevy, et al.,(2012). Emotion regulation and trader expertise: heart rate variability on the trading floor. Journal of Neuroscience, Psychology and Economics, 5(4) pp. 227-237.

Barnabás Póczos, Introduction to Independent Component Analysis, University of Alberta, Nov. 26, 2009.

Mark Fenton-O'Creevy, et al., Thinking, feeling and deciding: The influence of emotions on the decision making and performance of traders, Journal of Organizational Behavior, J. Organiz. Behav. 32, 1044-1061 (2011) Published online Jul. 26, 2010 in Wiley Online Library (wileyonlinelibrary.com) DOI: 10.1002/job.720.

Nelson J. Trujillo-Barreto, Bayesian model averaging in EEG/MEG imaging, NeuroImage 21 (2004) 1300-1319.

Giby Raphael, Neurophysiologic Approaches for Optimizing Teams, Conference Paper Oct. 2012, ResearchGate.

J. M. Coates, et al., Endogenous steroids and financial risk taking on a London trading floor, PNAS Apr. 22, 2008, vol. 105, No. 16, 6167-6172.

Tim Mullen, et al., Real-Time Modeling and 3D Visualization of Source Dynamics and Connectivity Using Wearable EEG, Conf Proc IEEE Eng Med Biol Soc. 2013; 2013: 2184-2187.

Fiona MacDonald, Scientists Show Human Consciousness Could Be a Side Effect of 'Entropy', https://www.sciencealert.com/human-consciousness-could-be-a-result-of-entropy-study-science.

Josef Faller, et al., Regulation of arousal via online neurofeedback improves human performance in a demanding sensory-motor task, www.pnas.org/cgi/doi/10.1073/pnas.1817207116.

Chris Berka, et al., Exploring Subjective Experience during Simulated Reality Training with Psychophysiological Metrics, Conference Paper Jan. 2011, ResearchGate.

* cited by examiner

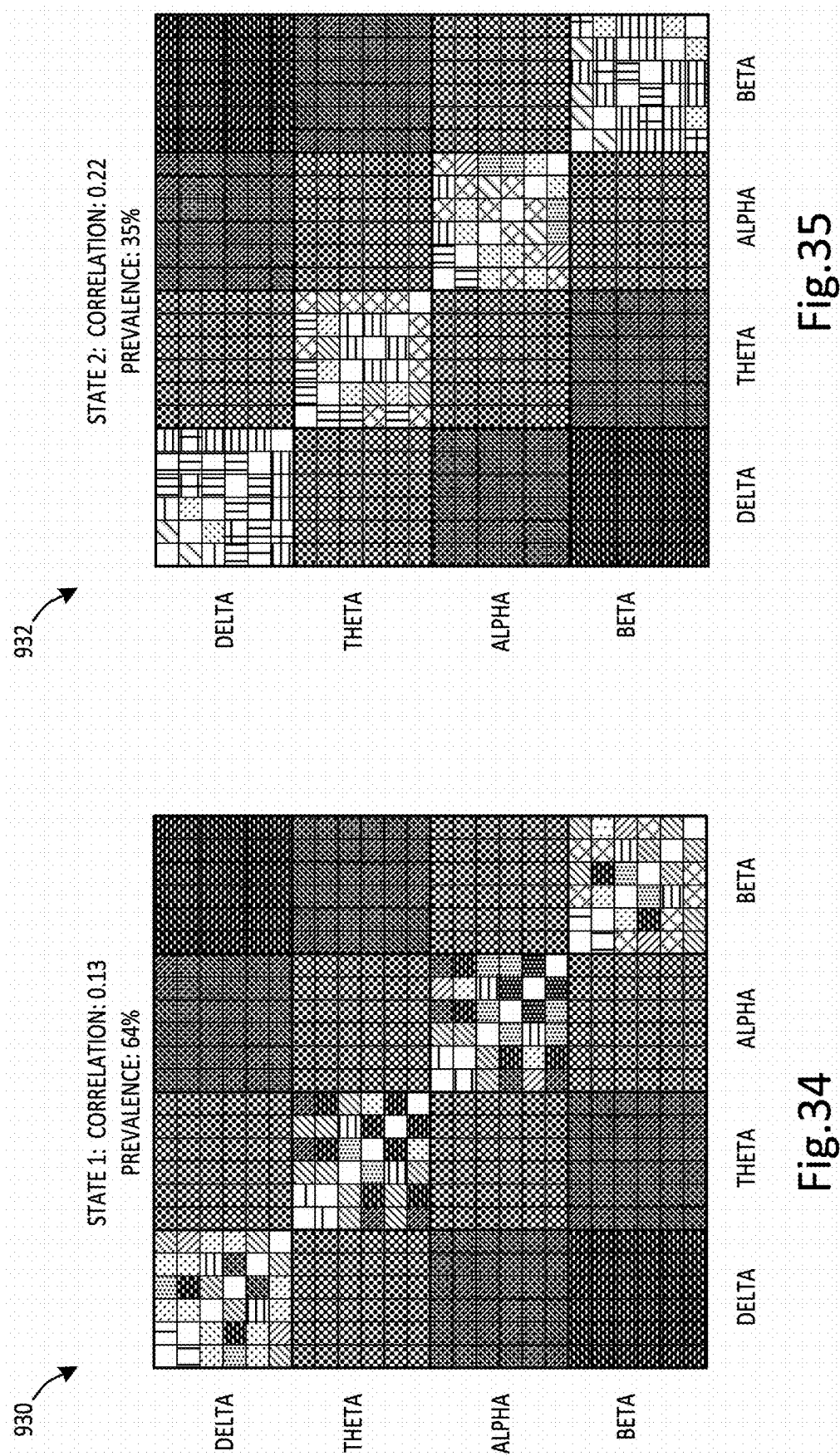

IDENTIFYING AND STRENGTHENING PHYSIOLOGICAL/NEUROPHYSIOLOGICAL STATES PREDICTIVE OF SUPERIOR PERFORMANCE

RELATED APPLICATIONS

This application claims the benefit of the following provisional applications, all of which are herein incorporated by reference:

| Docket No. | Ser. No. | Date Filed | Title |
| --- | --- | --- | --- |
| PLAT.0110 | 62/694,268 | Jul. 5, 2018 | Human 2.0 |
| PLAT.0100 | 62/711,668 | Jul. 30, 2018 | Neuroscience-Based Assessments and Closed-Loop Interventions |
| PLAT.0102 | 62/725,503 | Aug. 31, 2018 | Brain Imagery Feedback to Enhance Performance |
| PLAT.0103 | 62/725,517 | Aug. 31, 2018 | Method of Enhancing Team Preparation and Coaching |
| PLAT.0104 | 62/725,535 | Aug. 31, 2018 | Integrity Map of the Brain's Functional Systems |
| PLAT.0105 | 62/725,548 | Aug. 31, 2018 | Identifying Signatures of Task-Driven Brain Activity |
| PLAT.0106 | 62/725,567 | Aug. 31, 2018 | Neuroscience-Based Assessments and Closed-Loop Interventions |
| PLAT.0107 | 62/725,590 | Aug. 31, 2018 | Engagement Monitoring System to Improve Learning |
| PLAT.0108 | 62/725,605 | Aug. 31, 2018 | Method of Diagnosing Functional Systems of the Brain |
| PLAT.0109 | 62/725,626 | Aug. 31, 2018 | Closed-Loop Adaptive Training System Using Neurofeedback |
| PLAT.0111 | 62/725,638 | Aug. 31, 2018 | Neurocognitive Testbed |
| PLAT.0112 | 62/724,660 | Aug. 30, 2018 | Individual Assessment Report |
| PLAT.0113 | 62/724,665 | Aug. 30, 2018 | Human 2.0 |
| PLAT.0114 | 62/793,171 | Jan. 16, 2019 | Increasing Cognitive Health and Brain Health in Corporate Executives |
| PLAT.0115 | 62/798,922 | Jan. 30, 2019 | Neurological and Biological Feedback Method of Analysis, Training and Management of High-Risk Operations |
| PLAT.0116 | 62/831,134 | Apr. 8, 2019 | Neurological and Biological Feedback Method of Analysis, Training and Management of High-Risk Operations |

TECHNICAL FIELD

The present disclosure generally relates to the fields of neuroscience and neuroplasticity, and more particularly to neuroscience-based assessments and interventions.

BACKGROUND

The adult human brain has as many as 100 billion neurons. Each neuron is connected to up to 10,000 other neurons, implying as many as a quadrillion synaptic connections. The adult brain is also "plastic." It can be profoundly re-wired by experience, learning, and training. In the past decade, scientists have begun learning how to proactively "rewire" the brain. Efforts, with varying degrees of success, have been made to accelerate skill acquisition, enhance language learning, and delay the onset of cognitive decline. Innovations are needed to enable people to more effectively and quickly improve their decision-making, perception, cognition and motor performance.

In the past decade, the Defense Advanced Research Projects Agency (DARPA) conducted a study showing that the brains of marksmanship experts look different from those of novices when they are "in the zone." They also demonstrated a neurofeedback program where novices rapidly learned to create the expert brain state in marksmanship, doubling their accuracy within just a few training sessions. Other research has shown that visual processing speed is directly related to how many assists and steals a player generates in basketball, passing in soccer, and other sports-specific improvements. Further research has found relationships between high testosterone, antecedent-focused emotional regulation strategies, high-frequency heart rate variability and higher returns.

Relatedly, there has been interest in what factors influence traders in decision-making. In 2007, J. M. Coates and J. Herbert published an article in the Apr. 22, 2008 issue (vol. 105, no. 16, at pages 6167-6172) of the Proceedings of the National Academy of the Sciences of the United States of America (PNAS) entitled "Endogenous steroids and financial risk taking on a London trading floor," which is herein incorporated by reference. The article reported the findings of a study of endogenous steroids taken from a group of male traders in real working conditions in London. The study found that higher testosterone may contribute to economic return.

In 2011, Mark Fenton-O'Creevy, Emma Soane, Nigel Nicholson, and Paul Willman published an article in the Jul. 26, 2010 issue (32, 1044-1061) of the Journal of Organizational Behavior entitled "Thinking, feeling and deciding: The influence of emotions on the decision making and performance of traders," which article is herein incorporated by reference. The article reported on the influence of emotions in decision making in traders in four City of London investment banks. The investigation found that traders deploying antecedent-focused emotional regulation strategies performed better than those employing primarily response-focused strategies.

In 2012, Mark Fenton-O'Creevy, Jeffrey Lins, Shalini Vohra, Daniel Richards, Gareth Davies and Kristina Schaaff published an article in the Journal of Neuroscience, Psychology and Economics, 5(4) pp. 227-237 entitled "Emotional regulation and trader expertise: heart rate variability on the trading floor," which article is herein incorporated by reference. The article described a psychophysiological study of the emotion regulation of investment bank traders. The study found a significant inverse relationship between high-frequency heart rate variability (HF HRV) and market volatility and a positive relationship between HF HRV and trader experience.

On Feb. 19, 2019, Josef Faller, Jennifer Cummings, Sameer Saproo and Paul Sajda published an article in the PNAS entitled "Regulation of arousal via online neurofeedback improves human performance in a demanding sensory-motor task," which is herein incorporated by reference. The study demonstrated that online neurofeedback could shift an individual's arousal from the right side of the "Yerkes-Dodson curve" (which posits an inverse-U relationship between arousal and task performance) to the left toward a state of improved performance. Furthermore, the study demonstrated that simultaneous measurements of pupil dilation and heart-rate variability showed that neurofeedback reduced arousal, indicating that neurofeedback could be used to shift arousal state and increase task performance.

There is a need for further research and development into relationships between brain states and performance across a variety of fields. In particular, there is a need to discover relationships that yield improved sensory and feedback systems, which requires further research on ways to characterize and recognize physiological states and brain states that correlate with different levels of performance. There is also a need to develop improved data-based intervention and training programs to enable humans to reach greater potentials and levels of achievements. There are significant challenges in designing systems and methods that can practically and efficiently harness this knowledge into accelerated learning programs and better productivity and performance.

SUMMARY

A system and method are provided to measure and assess baseline brain performance, boost performance in targeted areas, and demonstrate, visualize, and track success. The system and method have many inventive aspects, not all of which are recited (or required) in every claim. In a first aspect, the system/method provides quantitative measures of cognitive reserve, brain entropy, and other cognitive traits.

In a second aspect, the system/method provides visualized brain state feedback derived from a stream of neurophysiological sensor data directly to the subject whose brain state is being visualized, in order to enhance performance. In a third aspect, the system/method uses neurophysiological sensor data (at least) to investigate and reveal functional systems of the brain. In a fourth aspect, the system/method uses neurophysiological sensor data (at least) to enhance team preparation and coaching. In a fifth aspect, the system/method uses neurophysiological sensor data and correlated performance data (at least) to identify brain pathways associated with a given task and signatures (representative patterns) of task-driven brain activity.

In a sixth aspect, the system/method generates a map of selected brain's functional systems (which in one implementation includes all of the brain) superimposed with colored regions and pathways to illustrate the strength and integrity of the selected functional systems, which comprise one or more brain regions and the pathways, if any, that connect them. In a seventh aspect, the system/method generates a predictive model of performance based on the neurophysiological data (at least). In an eighth aspect, the system/method examines the neurophysiological sensor data to monitor a subject's attention. The system/method also interrupts a task or activity, and/or administers a stimulus (either in combination or singularly—e.g., haptic, visual, or auditory) to help the subject refocus on and re-engage with the task or activity. In a ninth aspect, the system/method uses neurophysiological sensor data to adapt the training system in real time.

Advantageously, the system and method's use of neurometric data substitutes or complements traditionally qualitative and behavioral assessments and observational evaluations of brain performance with actual quantitative measures of brain performance.

This application also describes ways to test cognitive reserve or resilience that are adapted for identifying experts in the performance area and in training persons to become expert in the performance area.

In one embodiment, brain performance is quantified by measuring the decrement in performance between an initial, baseline measure of motor speed, and a final measure of motor speed. In between the initial and final measures, the subject is challenged to perform multiple tasks that create various pressures on the subject's ability to perform. In one implementation, the subject is given a motor speed test followed by an extended cognitive test followed by another motor speed test. The ability to not be impacted by the incremental changes in cognitive load provides a measure of resilience and reserve across time.

In another embodiment, subjects are provided a set of tasks which are varied by practice, day, sleep cycle, time from last meal, and other variables. Task pressures are modified to better understand how different pressures affect a subject's reserve. As one type of pressure is increased, how much can the subject adapt to maintain the same level of performance before decrements in performance are observed? For example, distractions, irritations, and provocations are incorporated into the tasks to understand how loud noises, interruptions and other forms of stimulus, morale, competitive pressure, and competitive affinity pressure (pressure of a team) affect a subject's performance.

Applications of the invention include developing proficiency in secondary language acquisition, real-world practical memory performance, and performance enhancement in groups of non-impacted individuals (e.g., not sleep deprived) or high performing individuals. Additional applications include developing precision learning models at the individual brain network level, versus for groups of brains. Tailored applications of the invention are described for athletes, employees, and financial traders.

A method is provided for improving analysis, performance and management of intense, high-risk operations such as security trading and portfolio management. In late 2018, Applicant conducted a research study to understand and characterize the impact that neurophysiological factors have on the financial performance of portfolio managers (i.e., traders). The specific intent was to identify measurable neurophysiological "states" that are reliably correlated with performance.

Following months of data analysis, the research study succeeded in identifying and characterizing the trader's brain states during their trading day using an unsupervised machine learning algorithm. To characterize the traders' brain states, the traders' neurophysiological data was transformed into a space that efficiently represented their brain activity as a set of nodes. With this in hand, connectivity between these nodes was calculated via correlational measures in the neural activity, yielding distinct functional connectivity patterns and an ability to differentiate the traders' brain states based on whether or not they were exhibiting functional connectivity among specified brain regions.

Multiple distinct brain states that each of the traders went in and out of during their trading day were identified. In one of these states, the traders' brains demonstrated a high degree of "functional connectivity," meaning that several distinct regions within their brains were functionally interconnected and operating in synchrony with one another. In the other state (broadly defined), this type of functional connectivity was not present. It is worth noting that the functional connectivity (FC) pattern identified via the unsupervised machine learning algorithm was remarkably consistent among the traders.

Other systems, devices, methods, features, and advantages of the disclosed system and methods will be apparent or will become apparent to one with skill in the art upon examination of the following figures and detailed description. All such additional systems, devices, methods, features, and advantages are intended to be included within the description and to be protected by the accompanying claims.

BRIEF DESCRIPTION OF THE DRAWINGS

The present disclosure can be better understood with reference to the following figures. Corresponding reference numerals designate corresponding parts throughout the figures, and components in the figures are not necessarily to scale.

It will be appreciated that the drawings are provided for illustrative purposes and that the invention is not limited to the illustrated embodiment. For clarity and in order to emphasize certain features, not all of the drawings depict all of the features that might be included with the depicted embodiment. The invention also encompasses embodiments that combine features illustrated in multiple different drawings; embodiments that omit, modify, or replace some of the features depicted; and embodiments that include features not illustrated in the drawings. Therefore, it should be understood that there is no restrictive one-to-one correspondence between any given embodiment of the invention and any of the drawings.

FIG. 34 is a symmetric functional connectivity plot revealing correlations between brain waves and correlations between PCA components of a first brain state.

FIG. 35 is a plot like that of FIG. 34, but for a second brain state.

DETAILED DESCRIPTION

Figure 1:
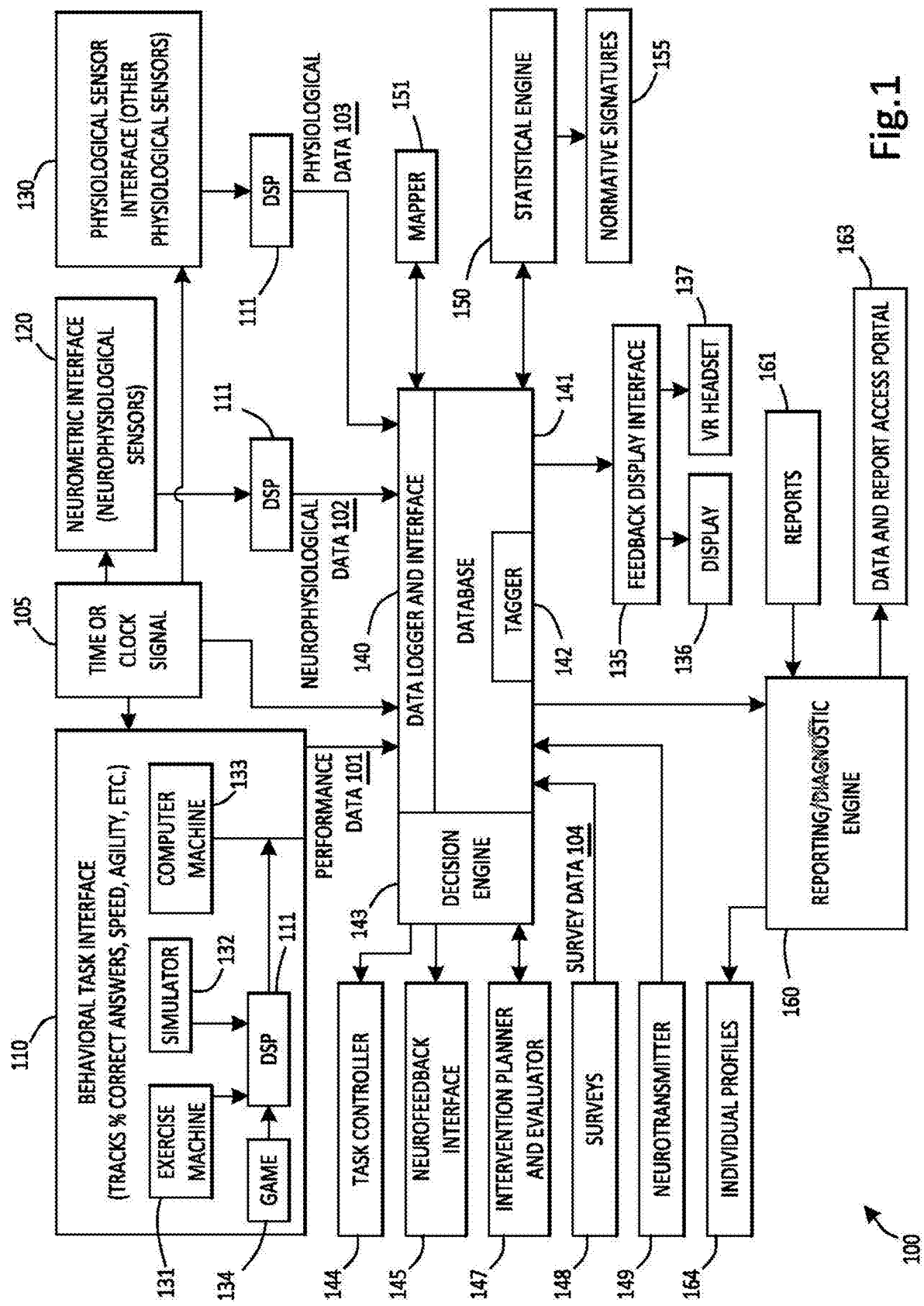
FIG. 1 is a block diagram illustrating components of one embodiment of a neurometric-enhanced performance assessment system.

Specific quantities (e.g., spatial dimensions) can be used explicitly or implicitly herein as examples only and are approximate values unless otherwise indicated. Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges can independently be included in the smaller ranges is also encompassed within the invention, subject to any specifically excluded limit in the stated range. Where the stated range includes one or both of the limits, ranges excluding either both of those included limits are also included in the invention.

In describing preferred and alternate embodiments of the technology described herein, various terms are employed for the sake of clarity. Technology described herein, however, is not intended to be limited to the specific terminology so selected, and it is to be understood that each specific element includes all technical equivalents that operate similarly to accomplish similar functions. Where several synonyms are presented, any one of them should be interpreted broadly and inclusively of the other synonyms, unless the context indicates that one term is a particular form of a more general term.

In the specification and claims, conventionally plural pronouns such as "they" or "their" are sometimes used as non-gendered singular replacements for "he," "she," "him," or "her" in accordance with emerging norms of pronoun usage. Also, although there may be references to "advantages" provided by some embodiments, other embodiments may not include those same advantages, or may include different advantages. Any advantages described herein are not to be construed as limiting to any of the claims.

To provide a better appreciation of the invention, the following neuroscience concepts and terms of art are explained.

Systems of the Brain

One traditional anatomical model characterizes the brain as consisting of a plurality of anatomical systems, such as the prefrontal cortex, visual cortex, auditory cortex, primary motor cortex, and primary sensory cortex. Another anatomical model characterizes each hemisphere of the brain as consisting of a frontal lobe, insular cortex, limbic lobe, temporal lobe, parietal lobe, occipital lobe, cingulate gyms, subcortical structures, and cerebellum. Many of these brain structures can be further subdivided. For example, the subcortical structures of the brain include the forebrain, the midbrain, and the hindbrain. Each of these comprises a plurality of substructures, and many of the substructures can be characterized as having their own smaller subparts, and so on. More information can be found in the article by Tim Mullen et al., "Real-Time Modeling and 3D Visualization of Source Dynamics and Connectivity Using Wearable EEG," Conf Proc IEEE Eng Med Biol Soc. 2013; 2013: 2184-2187, which is herein incorporated by reference.

Another model characterizes the brain as having a visual association area, auditory association area, somatic motor association area, somatic sensory association area, Wernicke's area (for understanding speech), and Broca's area (for production of speech).

The brain also includes several major neural pathways. A neural pathway refers to the connection formed by axons that project from neurons to make synapses onto neurons in another location, to enable signals to be sent from one region to another. Neurons may be connected by either a single axon or a bundle of axons known as a nerve tract. The gray matter of the brain contains many short neural pathways. Long pathways may be made up of myelinated axons, which constitute white matter. A neural highway refers to a pathway with a large number or bundle of neural connections.

There are several well-studied major neural pathways, just a few of which are described here. The corpus callosum is the largest white matter structure in the brain, connecting the left and right cerebral hemispheres. The arcuate fasciculus connects Broca's Area to Wernicke's Area, both of which are specialized for language. The medial forebrain bundle connects the septal area of the forebrain with the medial hypothalamus, all of which are considered part of the reward system of the brain, but which also have a role in the brain's grief/sadness system. The cerebral peduncle connects parts of the midbrain and is important in refining motor movements, learning motor skills, and converting proprioceptive information into balance and posture maintenance. The corticobulbar tract conducts brain impulses associated with voluntary movement to the spinal cord. The corticospinal tract is involved in movement in muscles of the head, including facial expressions. The dorsal column-medial lemniscus pathway is a sensory pathway that conveys sensations of fine touch, vibration, two-point discrimination, and proprioception from the skin and joints.

One functional model characterizes the brain as having five major systems: cognition, attention and language, sleep and consciousness, memory, and emotion. Functional models are being adapted to recognize that a given cognitive function may recruit many different anatomical regions and pathways of the brain.

In "Structural and Functional Brain Networks: From Connections to Cognition," dated Nov. 1, 2013 and which appeared in Vol. 342 of the magazine "Science," and which is herein incorporated by reference, authors Hae-Jeong Park and Karl Friston characterize the brain as comprising a "modules," which largely correspond with what previous researchers referred to as "functional networks" or "intrinsic connectivity networks" (ICNs), examples of which include the default mode network, dorsal attention network, executive control network, salience network, and the sensorimotor, visual, and auditory systems. Each module is characterized by dense intrinsic connectivity within the module and sparse and weak extrinsic connections to other modules. Each module comprises a plurality of "submodules" that are characterized by synchronously active, persistently stable voxels. Each submodule comprises a plurality of hierarchically structured "nodes" or "voxels." Each node is equipped with intrinsic connections and states. Finally, each node is connected by "edges" to other nodes. The "edges" can be defined by any of three notions of connectivity: structural, functional, and effective. The authors also characterize node clusters that are highly interconnected to other modules as "rich-club hubs," which are critically important for global communication between brain modules. Specialized brain functions, the authors found, are characterized by local integration within segregated modules and the functions of perception, cognition, and action by global integration of modules.

Park and Friston's 2013 article was not the first to characterize complex brain networks in terms of graph theory. In "Complex brain networks: graph theoretical analysis of structural and functional systems," dated March 2009 and which appeared in volume 10 of the journal "Nature," and which is herein incorporated by reference, authors Ed Bullmore and Olaf Sporns describe some measures that have emerged for the analysis of brain networks. The "degree" of a node is defined by the number of connections that link it to the rest of the network. Collectively, the degrees of all the nodes defines a degree distribution. Assortativity relates to the correlation between degrees of connected nodes. Path length is the minimum number of edges that must be traversed to go from one node to the other. The "centrality" of a node refers to the number of shortest paths between all other node pairs in the network that must pass through the node. The authors also noted that the concept of a "node" or "voxel" may be defined by the imaging resolution producing the brain image (which is insufficient to distinguish each neuron). For example, a node may be the anatomically localized region or voxel of an fMRI image or equate to whatever group of neurons an individual EEG electrode or MEG sensor senses.

Collectively, these models establish that effective connectivity and functional connectivity is constrained by structural connectivity, but structural connectivity does not fully determine functional or effective connectivity.

Cognition

Cognition is the mental action or process of acquiring knowledge and understanding through thought, experience, and the senses. Cognition encompasses several processes, including attention, knowledge formation, memory and working memory, judgment and evaluation, reasoning and computation, problem solving and decision making, and language comprehension and production. The fields of biology, neuroscience, psychiatry, psychology, logic, systemics, linguistics, and anesthesia each analyze cognitive states from different perspectives.

Cognitive State

A cognitive state refers to one's thought processes and state of mind. The classification of cognitive processes is, as a matter of practice, described using terms already found in English. For example, one study of children classified the following cognitive states: confidence, puzzlement, hesitation. Another study of military personnel classified the following states: planning, movement, giving/receiving orders, receiving information, clearing a building, responding to enemy, responding to civilians, reporting, responding to action, defending, securing, requesting, maintaining vigilance, preparing equipment, and after-action review. Other examples include distracted, confused, engrossed, amnesia, and paramnesia. These states are defined on the basis of how the person is acting and responding.

Brain State

Brain states are often discussed, but rarely defined. Discussions about the meaning of "brain state" are most frequently found in philosophical journals and forums. Richard Brown, in his article "What is a Brain State" published in the Journal of Philosophical Psychology, 23 Nov. 2006, argues that "brain states are patterns of synchronous neural firing, which reflects the electrical face of the brain; states of the brain are the gating and modulating of neural activity and reflect the chemical face of the brain." One student by the name of Karl Damgaard Asmussen argues: "A brain state is a snapshot of everything in the central-nervous-system. A brain state is said to contain everything about a person right the instant it is snapshotted: memories, emotions, skills, opinions, knowledge, etc." What these definitions have in common is that "brain state" is objective, material, and in some way quantifiable, in contradistinction to "cognitive state" and "mental state," which are typically described using social constructs—although plausible philosophical arguments can be made that a "cognitive state" is nothing more than a "brain state." There are many different ways to characterize a "brain state," including power spectral density, activated networks and patterns of correlation between brain waves.

This application embraces a practical definition of a brain state, as an objectively discernable and quantifiable pattern of power density, neuronal firing, correlations between brain waves, and/or other dynamic physical characteristics of the brain. As used in this application, brain states can be statistically defined and may not have a one-to-one relationship with a "cognitive state" or "mental state" label. These brain states can be observed during conscious, subconscious and/or sleep stages. Moreover, because as a practical matter it is impossible to obtain an infinitely detailed "snapshot of everything in the central-nervous system," a "brain state," as used herein, encompasses practical, detailed-enough-to-be-useful snapshots of dynamic physical characteristics of the brain. For example, a "brain state" may be characterized by the functional coordination of the connectivity and coherent phase-amplitude coupling between a brain's delta, theta, alpha, and beta frequency waves.

Cognitive Domain

In 1956, under the leadership of Dr. Benjamin Bloom, a taxonomy of learning domains was created. The learning domains consisted of the cognitive, affective and psychomotor domains. The cognitive domain was described in terms of six classifications: knowledge, comprehension, application, analysis, synthesis, and evaluation. The affective domain was classified as how a person receives and responds to phenomena, attaches worth or value to something, compares, relates, synthesizes values, and internalizes values. The psychomotor domain was classified as perception, set, guided response, basic proficiency, complex overt response, adaptation, and origination.

These taxonomies have evolved over time. For example, the Alzheimer's Association identifies the following as the four core cognitive domains: recent memory—the ability to learn and recall new information; language—either its comprehension or its expression; visuospatial ability—the comprehension and effective manipulation of nonverbal, graphic or geographic information; and executive function—the ability to plan, perform abstract reasoning, solve problems, focus despite distractions, and shift focus when appropriate. Others have created other cognitive domain taxonomies that are multi-dimensional.

As can be seen from the above discussion, there is some overlap and blurring of the definitions of "cognitive state" and "cognitive domain." Moreover, all three of the learning domains are sometimes referred to as "cognitive domains." Also, in some of the classifications, there is no rigorous consistent rationale for why the classifications are chosen. In the claims, the use of these terms is not limited to any one set of the aforementioned classifications.

Default Node Network

The default node network is a set of posterior, anterior medial, and lateral parietal brain regions that comprise the default mode network. These regions are consistently deactivated during the performance of diverse cognitive tasks. They are most active when a person is in a state of wakeful rest, such as daydreaming or "mind wandering." The default mode network activates immediately and "by default" after a person has completed a task.

Attention

The American Psychological Association describes attention as a state in which cognitive resources are focused on certain aspects of the environment rather than on others and the central nervous system is in a state of readiness to respond to stimuli. Human beings do not have an unlimited capacity to attend to everything. They must focus on certain items at the expense of others. A neuroscience-based definition of attention is "a process or computation including a group of distributed brain regions resulting in a non-linear summation of competing environmental information, the result of which is to bias selection and action to one option while simultaneously filtering interference from the remaining alternatives."

Researchers have identified (at least) two anatomically and functionally distinct attention networks, which are referred to as the dorsal and ventral attentional systems or networks. The dorsal frontoparietal system, also referred to as the task-positive network, mediates goal-directed top-down guided allocation of attention to locations or features. It supports the ability of someone to voluntarily focus increased attention on an attention-demanding task and to tune out other sensory inputs. The ventral frontoparietal system, mediates stimulus-driven, bottom-up attention and is involved in involuntary actions. It exhibits increased activity when detecting unattended or unexpected stimuli and triggering shifts of attention.

Functional Brain Connectome

A functional brain connectome is a comprehensive description of the brain's structural and functional connections in terms of brain networks.

Physiological and Neurophysiological Sensors

A physiological sensor is a sensor that senses some physiological signal or function of a living organism or its parts. A subset of physiological sensors comprises neurophysiological sensors. Neurophysiology is a discipline concerned with the integration of psychological observations on behavior and the mind with neurological observations on the brain and nervous system. Neurophysiological sensors include sensors that measure brain signals, or a psychological function known to be linked to a particular brain structure or pathway. Neurophysiological measurements can be taken in conjunction with a stimulus, sometimes simple, sometimes complex such as a subject taking a behavioral test, viewing content or engaging in a work-related task.

Common but non-limiting examples of neurophysiological sensors include a portable electroencephalograph (EEG), a diffuse optical technology (DOT) scanner, a diffusion magnetic resonance imager (MRI), a functional magnetic resonance imager (fMRI), a magnetoencephalography imager (MEG), positron emission tomography (PET) and a functional near-image spectroscopy (fNIR).

EEG measures electrical signals in the brain, usually using a plurality of electrodes strategically placed on different parts of the scalp. The EEG electrodes are in contact with the scalp via several potential modalities (e.g., a water-based gel, hydrogel, capacitive dry sensor, etc.) and are used to record electrical potentials produced by electrical field activity in the brain. The brain contains many billions of neurons, no one of which can produce enough of a potential difference to be measured and identified. However, brain activity is characterized by significant levels of local field synchrony that, in the aggregate, produce far-field potentials that project, with different loadings, to nearly all of the EEG sensors in an EEG recording. EEG is also useful in revealing the effective connectivity of the brain. However, EEG sensors pick up not only genuine brain activity, but also spurious potentials from other sources (such as eye movements, scalp muscles, line noise, scalp and cable movements) and channel noise. These spurious sources may produce greater potentials than the cortical sources and should be accounted for in analysis.

Diffusion MRI measures the rate of water diffusion in the brain and is useful in revealing the structural connectivity of the brain. fMRI measures the difference between oxygenated and deoxygenated blood in the regions, from which activity is imputed. Because neuronal activity and blood flow are coupled, it is useful in revealing the functional and effective connectivity of the brain. However, it is currently very slow compared to EEG. A MEG maps brain activity by recording magnetic fields produced by electrical currents occurring naturally in the brain. Advantageously, MEG is very fast, like EEG. A DOT scanner captures tomographic images by utilizing light in the near-infrared region (700 nm to 1100 nm) that exerts minimal effects on the human body. fNIR is the use of the use of near-infrared spectroscopy (NIRS).

Nonlimiting examples of physiological sensors other than neurophysiological sensors include the following: an electrocardiogram (ECG); a respiratory inductive plethysmography band that measures respiration rate at the rib cage; a galvanic skin response (GSR), skin conductance response (SCR), or Electrodermal Activity (EDA); a skin temperature sensor using a surface probe thermistor; a pulse oximeter to measure blood oxygen levels and heartrate; a respirator analyzer to measure CO2 and O2 respiratory contents. There are many other examples, including sensors that quantify perspiration, muscle flexion, facial expressions, eye wincing, and blinking frequency, pupil dilation, head/body position, cortisol level, adrenaline level, and other hormone levels.

Brain Mapping

Brain mapping is the illustration of the anatomy and function of the brain and spinal cord through the use of imaging, immunohistochemistry, molecular genetics, optogenetics, stem cell and cellular biology, engineering, neurophysiology and/or nanotechnology. Typically, brain mapping is understood to involve the mapping of quantities or properties (generated by neuroscientific techniques) onto diagrams or spatial representations of the brain, wherein color-coding and/or line thickness is used to represent those quantities or properties. As used herein, a "brain map" is intended to be understood broadly as a symbolic depiction that emphasizes relationships between structures of the brain.

For example, a brain map may project a representation of brain activity onto brain regions, using neuroscientific techniques such as fMRI. Detected brain activation is frequently represented by color-coding the strength of activation across the brain or a selected region of the brain.

Another example of a brain map is a connectome (aka connectogram) that depicts cortical regions around a circle, organized by lobes. This type of brain map is a diagram rather than a spatial representation of the brain. Separate halves of the connectome are used to depict the left and right sides of the brain. Each half is subdivided into lobes of the brain, and each lobe is further subdivided into cortical regions. Inside the circle are concentric rings that represent attributes of the corresponding cortical regions, including the grey matter volume, surface area, cortical thickness, and degree of connectivity. Inside the rings, lines are used to connect regions of the brain that are found to be structurally connected. An opacity of each line is used to reflect the density of the connection. The color of each line is used to represent the degree of anisotropy (directional dependency) of a diffusion process in that pathway.

Entropy

Entropy refers to a lack of dynamism and order in brain activity as a function of information presented to an individual. Entropy is frequently accompanied by subjective uncertainty or "puzzlement." The field of neuroscience characterizes entropy with a quantitative index of a dynamic system's randomness or disorder. The more a relevant system of the brain (e.g., the visual cortex) desynchronizes—e.g., is disrupted from a smooth, rhythmic, brain frequency, or the more pronounced is the change in the system's brain activity in response to information or stimulus—the more information is held or is being encoded by the brain. The extent of desynchronization is a measure of the system's information processing load, which leads also, conversely, to a measure of entropy across that system.

Brain entropy is not always necessarily bad. Two recent studies have found that greater resting-state brain entropy is correlated with higher verbal IQ and reasoning ability. Another study in Scientific Reports found that caffeine causes a widespread increase in cerebral entropy. They suggest that entropy can be an indicator of the brain's readiness to process unpredictable stimuli from the environment. Another recent study speculates that human consciousness may be a by-product of brain entropy.

Cognitive Reserve

Cognitive reserve refers to the capacity of the brain (processing) to do further work or decision making. In habit/willpower literature, there is some speculation that people essentially have a reserve of willpower. As a person make decisions throughout the day, this decrements the person's decision-making power. By the end of the day, the person has made so many decisions and exercised so much willpower that it depletes the person's cognitive reserve, making that person more susceptible into being talked into something. Accordingly, cognitive reserve refers to the resilience of a person's decision-making ability.

Cognitive reserve and cognitive resilience also refer to the ability of the brain to optimize or maximize performance through the differential recruitment of brain networks or alternate cognitive strategies. The scientific literature doesn't describe measurements for reserve very well, except with respect to decremented nervous systems, such as those beset by Alzheimer's and dementia.

Behavioral Data

Behavioral data refers to observational information collected about conscious actions and activities of a person under the circumstances where that behavior actually occurs. This includes, for example, a person's responses on a keyboard, mouse, game controller, or other input device to a computer task such as a game on a typical work-related task. In this specification, behavioral data is distinguished from physiological or neurophysiological data.

"Flow"

"Flow," a term in the field of positive psychology also colloquially known as being "in the zone," refers to a mental state of operation in which a person performing an activity, such as a sport, is fully immersed in a feeling of energized focus, full involvement, and enjoyment in the process of the activity. It is a state in which a person, while concentrated on the present moment, acts almost instinctively without distraction while focused intensely on a specific task or goal. It is often accompanied by a sense of personal control, a merging of action and awareness, a distortion of temporal experience, a loss of reflective self-consciousness, and even disregard for the person's need for food, water, and sleep.

Description of the Drawings

FIG. 1 is a block diagram illustrating components of one embodiment of a neurometric-enhanced performance assessment system (NEPAS) 100. The NEPAS 100 identifies relationships between brain state characteristics and performance of specific tasks by collecting performance and physiological (including neurophysiological) data from a subject, as well as from a population of subjects, while that subject and population of subjects perform tasks (optionally including tests). The population may be representative of, for example, the general public, a demographic group or subgroup, a professional group, or a specific team. Moreover, tasks are selected that are physiologically important, meaning that they differentially activate a part of the brain of which the system is testing the integrity. This enables NEPAS 100 to disassociate the integrity of two different parts of a subject's brain.

The NEPAS 100 utilizes this data in a plurality of ways, including modifying the tasks as a function of detected brain activity, identifying pathways in the brain associated with a given activity, identifying signatures of brain activity from the population, assessing the subject's brain activity and inferring the subject's brain functional connectivity, generating reports for the subject and the subject's trainer or coach (if any), building an intervention plan for the subject, and providing visual feedback of the brain's activity.

The NEPAS 100 comprises a neurometric interface 120 (also referred to as neurophysiological sensor interface or neurometric monitor), an optional physiological sensor interface 130, and a behavioral task interface 110. Digital signal processors (DSPs) 111 digitize any analog information collected by these interfaces 110, 120, and 130, and deliver neurophysiological data 102, physiological data 103, and performance data 101, respectively, to a data interface and logger/recorder 140. The logger/recorder 140 recorder collects and records neurometric data 102 from the neurometric interface 120, physiological data 103 from the physiological interface 130, the performance data 101 from the behavioral task interface 110 or some other source, and survey responses 104 from surveys 140. In one implementation, the collection of data 101, 102, and 103 are done simultaneously. The survey responses 104, task performance measurements 101, and physiological and neurophysiological data 102 and 103 can be collected from both internal and external sources (e.g., sports stats databases, financial databases) and delivered through several different modalities (e.g., tablet, laptop, VR headset, etc.).

The table below presents a list of physiological (including neurophysiological) metrics and the brain states or constructs to which they relate.

TABLE 1

Neuro/Physiological Metrics and Related Brain States or Constructs

| Neuro/Physiological Metric | Constructs/brain states |
|---|---|
| Heart rate variability | Emotional regulation |
| Affective state classifier | Emotional valence |
| Engagement classifier | Engagement |
| Midline theta | Attention, memory encoding and retrieval, positive emotions, and relaxation |
| Heart rate | Emotions and arousal (including stress) |
| Mu suppression | Empathy |
| Prefrontal gamma | Perception, attention, memory, and narrative comprehension |
| Workload classification | Workload |
| Left occipital alpha slow suppression | Visual imagery |
| Right occipital alpha slow suppression | Visual imagery |
| Left parietal alpha slow suppression | Kinesthetic imagery |
| Left parietal alpha slow suppression | Kinesthetic imagery |
| Gamma power phased lock to Hippocampal theta | Working memory span |
| Frontal theta and occipital alpha | Attention and novelty detection |

A tagger 142 links and tags the data 101, 102, 103, 104, and any other data about the subject that is input, with metadata, including synchronizing time or clock data as well as profile data. For example, a system 100 built for a basketball or football team can include player positions, such as point guard, offensive linemen, and defensive linemen. The data 101, 102, 103, 104, and any other data about the subject, complete with database links and metatags, is recorded into the database 141.

The behavioral task interface 110 is configured to facilitate the person's performance on one or more tasks. The behavioral task interface 110 also acquires performance data 101 while the person performs the task(s). It one implementation, the behavioral task interface 110 comprises one or more exercise machines 131, simulators 132, computer exercises 133, and games 134 (collectively, equipment for performing tasks) that have sensors, transducers and analyzers that produce signals and evaluations indicative of the subject's attentiveness, comprehension, visual processing, accuracy, decision-making prowess, performance under pressure, recovery/resilience, mobility, flexibility, reaction speed, physical speed, strength, agility, endurance and/or other performance metrics on the tasks. The behavioral task interface 110 prompts the subject to perform one or more tasks and collects performance data about a subject while the subject is performing the task. In one implementation, the tasks are predefined and automated, and performance data 101 is automatically generated. For example, a computer game or exercise could be programmed to make the computer automatically track aspects of the subject's performance. For other tasks, such as a worksite task, the behavioral task interface 110 can be an API to a worksite system. In an example applicable to financial traders, the behavioral task interface 110 would comprise a trading interface and various trading tools. Data relating to each of the trader's transactions would be collected and compared with market data to assess the player's performance.

In another implementation, a task-performance monitor (not shown), such as a speedometer, track sensor, GPS, a human observer, a game statistician provides the NEPAS 100 with access to measures of the subject's performance.

In one embodiment, the behavioral task interface 110 also provides feedback to the person. The feedback can be in the form of a startling light, sound, or haptic stimulus to refocus the training subject. In one implementation, the behavioral task interface 110 couples neurometric-based feedback with words of encouragement.

In one embodiment, the behavioral task interface 110 is mobile and the tasks are free-form, not automated. For example, a task can be playing a position in a game or sport or performing on a multi-tasking job. The subject wears portable physiological and/or neurophysiological sensors, and optionally also gyroscopes, motion sensors, counters and the like, while performing the free-form task. The equivalent of behavioral or task performance data could be supplied by an observer, a sport statistician, a database of stats about a game, work records about the quality and efficiency of the subject's performance on the task, etc.

The neurometric interface 120 can comprise any of or several of the neurophysiological sensors described in the background section of this application. In one implementation designed to identify the least restrictive and least expensive set of sensors that will adequately indicate the person's brain activity, the neurometric interface 120 is multimodal. For example, one neurometric interface 120 comprises both an EEG, which is portable, and a fMRI, which is not. The EEG comprises sensors that detect electrical activity in the brain. The sensory data is Fourier-transformed to identify brain wave frequencies of different parts of the brain. The fMRI and EEG measurements are taken simultaneously for an initial test audience to find correlations between the relatively more abundant and accurate fMRI data and the relatively sparse EEG data. With an adequate database of fMRI correlation data, EEG data can be interpreted more accurately to indicate activity in various brain regions and pathways. In another implementation, the neurometric interface 120 is simplified, such as being made to operate without the fMRI or with fewer EEG sensors or be distributed among a smaller surface area of the head, after sufficient data is obtained to demonstrate that reasonably accurate measurements of brain activity can still be obtained. In another implementation, the neurophysiological sensors are EEG sensors that are distributed across left and right hemispheres of the brain, to ensure that a differential analysis can be made of brain activity on the left and right hemispheres of the brain.

In another implementation, the neurometric interface 120 comprises a plurality of neurophysiological sensors arranged on a base, such as a headband or virtual reality headset 137, plus a power supply and a transmitter that transmits neurometric data to the recorder. The base is configured to be worn on the subject's head and to place the neurophysiological sensors in contact with the head.

The optional physiological interface 130 can comprise any of the physiological sensors described in this application. Some of the sensors can be incorporated in devices such as wrist watches, chest bands, and the like, that minimally impede, if at all, the subject's performance of the tasks.

Physiological data such as heartrate, respiration rate and depth, blood oxygen levels, and stress levels (as, for example, estimated from cortisol levels) provide important insight into characteristics of a brain state. Correlating physiological data with performance data and neurophysiological data facilitates the development of even keener evaluations, subject diagnoses, recommendations, and training programs. Further examples of physiological characteristics that are measured in other implementations of NEPAS 100 include:

a skin capacitance/galvanic response of the subject;
a temperature of the subject;
a stress level of the subject;
perspiration by the subject;
a tightening of a muscle (e.g., jaw muscle clenching teeth);
whether the subject is wincing;
whether the subject's pupils are dilating;
eye movements;
the subject's head or body position;
the subject's cortisol level;
the subject's adrenaline level; and
the subject's blinking frequency.

A time or clock signal 105 (such as one or more synchronized time servers, a common clock signal, or more generally a "synchronizer") synchronizes the performance data 101, the neurophysiological data 102, and the physiological data 103, ensuring that each increment of simultaneously-collected data is tagged with the same time or clock value. In one implementation, each of the interfaces 110, 120, and 130 are fed a common time value 150 from one or more synchronized time servers, such as time.apple.com or time.windows.com, to which they are communicatively coupled. In another implementation, a periodic signal (not necessarily representative of time) is fed directly by wire into each of the interfaces 110, 120 and 130 to synchronize the data 101, 102 and 103. In yet another implementation, already-time-stamped external data, such as market-wide financial trading data, is synchronized with internally collected data.

In one implementation, the NEPAS 100 incorporates information from not only mechanical interfaces, but also surveys 148. The surveys 148 ask the subject to self-report about his/her workload, sleep quality, feelings of stress, mental focus and attentiveness versus distractibility, and motivation, as well as other emotions (e.g., anxiety, frustration, anger). The surveys 148 can be used not only for assessment, but also for training. For example, a survey completed right after a subject has a disappointing performance (e.g., a loss) can be followed by a mindfulness application to drive the subject back to a baseline. Surveys can also be used to collect other information such as measurements of stress, insomnia, depression, demographics, or other particulars of a person's life, job, etc.

In another implementation, the NEPAS 100 incorporates information from neurotransmitter tests 149. The neurotransmitter tests 149 one or more of the following: urine tests and blood tests. For example, a baseline test panel can be taken that provides data on 11 key neurotransmitters and precursors: glutamate, epinephrine, norepinephrine, dopamine, PEA, GABA, serotonin, glutamine, histamine, glycine and taurine.

In another implementation, the NEPAS 100 also incorporates non-physiological contextual data, such as data about the environment (e.g., temperature, humidity, altitude, storm conditions, terrain), the opposing player, or the subject (e.g., sick, suffering from an injury). The assessment takes this contextual data into account when assessing the subject and the subject's performance data.

The data interface and logger/recorder 140 collects the performance, neurophysiological, physiological, and survey data 101, 102, 103 from not only a particular subject, but also a plurality of subjects in order to identify patterns that statistically correlate performance data and sensed physiological characteristics across the plurality of subjects.

Responses 104 from surveys 148 and results of neurotransmitter tests 149 are also input to the data interface and logger/recorder 140.

The data interface and logger/recorder 140 logs and records the data into the database 141. In one implementation, the database 141 is a relational, query-retrievable database.

To process and use the data 101, 102, 103 and 104, the NEPAS 100 provides one or more of a feedback display interface 135, a statistical engine 150, a mapper 151, a reporting engine 160, a database 141, and a decision engine 143. The mapper 151 superimposes a preferably live representation of brain activity derived from the neurophysiological data 102 onto a 3D model of a brain. This illustrates areas and/or pathways of the brain that are activated by a given task, and how those area and pathways change over time while the person performs the tasks. The 3D model can be representative of either a normal brain or the brain of the subject being assessed, or it can be a caricature of the brain. The 3D model is presented to the feedback display interface 135, which is a monitor, screen, video-containing headset, VR headset 137, game headset, glasses-embedded display, or other display device. The feedback display interface 135 is located within a viewing range of the subject and while the subject performs the tasks. The feedback display interface 135 provides the subject a visualization of the mapped 3D model to the subject while the subject is performing the task. In some implementations, the visualization is live, in real-time, with relatively little lag time. In other implementations, one or more visualizations are provided after the task is completed. In another implementation, the feedback display interface 135 also provides real-time assessment information about the subject's performance and physiological (including neurophysiological) characteristics.

The statistical engine 150 processes and analyzes the data 101, 102, 103, and 104 collected from a population of subjects to build normative models of brain activity and correlated performance levels for each of a plurality of task conditions (i.e., states). The statistical engine 150 can make use of machine learning, deep learning, and neural networks to identify patterns between the performance data 101 and other data and brain activity.

Figure 27:
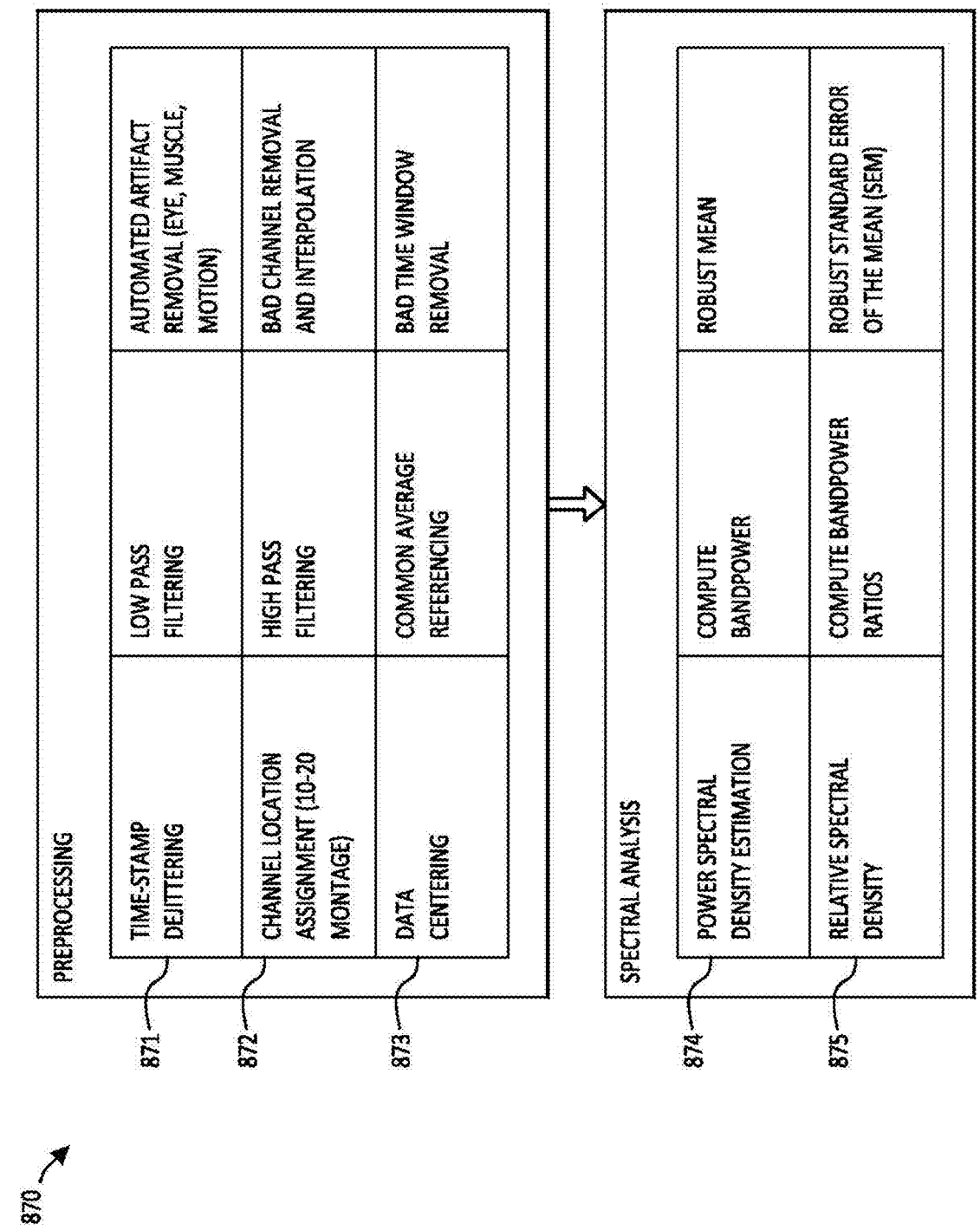
FIG. 27 is a flow chart illustrating preprocessing and spectral analysis steps used to analyze EEG data in pre-training and post-training assessments.

FIG. 27 illustrates one embodiment of a preprocessing and spectral analysis data pipeline 870. First, the data or a single one of the data sets 101-104 are preprocessed by undergoing filtering, including timestamp dejittering 871, channel location assignment 872, and data centering 873. The dejittering 871 utilizes low pass filtering to automatically remove eye and muscle motion artifacts. The channel location assignment 872 involves high pass filtering and interpolation to remove bad channels. The data centering 873 involves common average referencing to remove bad time windows. Second, the data undergoes a spectral analysis, including both a power spectral density estimation 874 and a relative density estimation 875. The power spectral density estimation 874 decomposes the signal data into one more individual frequency components, in order to determine a baseline power of pathways of the brain and the calculation of a robust mean. The relative density estimation 875 involves determining the power of those same pathways during the execution of a complex skill or task, calculating a ratio between this power and the baseline power, and calculating a robust standard error of the mean (SEM).

The statistical engine 150, in another embodiment, uses unsupervised and/or supervised principal component analysis (PCA) to identify brain states that explain the greatest amount of variance in performance. FIGS. 29-40 illustrate the use of PCA in an application of NEPAS 100 to financial traders. PCA is similarly applicable to data related to other domains, such as sports efficiency and teamwork. In another embodiment or in addition to PCA, independent component analysis (ICA) is used to identify independent source components of the data, for example, EEG artifacts caused by eye and muscle movements as well as components related to brain states.

The statistical engine 150 processes the data 101, 102, 103, and 104 from the population. In particular, the statistical engine 150 compares the spatial-temporal pattern of the physiological indicators across the task conditions (states) to make inferences of the neurophysiological basis of various states (e.g., inattention or overloaded). From this information and analysis, the statistical engine 150 generates models of task-oriented brain activity that include brain activity "signatures" comprising the degree of connectivity, speed, and directionality of a brain network of a subject, a population, and/or a real or normative expert performance cognitive state.

The statistical engine 150 creates normative wide-population signatures 155 of spatially distributed brain activity for the population of subjects performing various tasks, as well as normative expert-level signatures 155 of brain activity of experts who perform exceedingly well on those tasks. As used herein, "expert" can refer to persons who perform anywhere in the top X percentile of the population, wherein X refers to a threshold percentile number, such as 1%, 5%, 10%, 15%, etc., wherein population may refer to either the general population or a particular profession. Alternatively, "expert" can refer to persons who have well-defined neural signals or functional connectivity patterns (as quantified by a suitable metric), compared with those of a general population, during performance of a task. For example, it has been shown that expert sharpshooters exhibit a well-defined neural signal when they are engaging in known-distance shooting.

For a particular subject, the statistical engine 150 produces a real-time assessment of the subject's performance and that performance's relationship to a physiological state of the subject, wherein the physiological state is determined by the neurometric data.

The reporting engine 160 queries the database 141 to build or obtain a profile 164 for the subject, generate an assessment of the subject's performance and physiological characteristics from the performance data 101, the neurometric data 102, and the physiological data 103, and produce graphical & textual reports 161 about the subject's neurophysiological and behavioral performance on the tasks. The reporting engine 160 also optionally use the normative signatures 155 of performance as a baseline against which to compare a subject's brain activity and/or functional connectivity.

Figure 22:
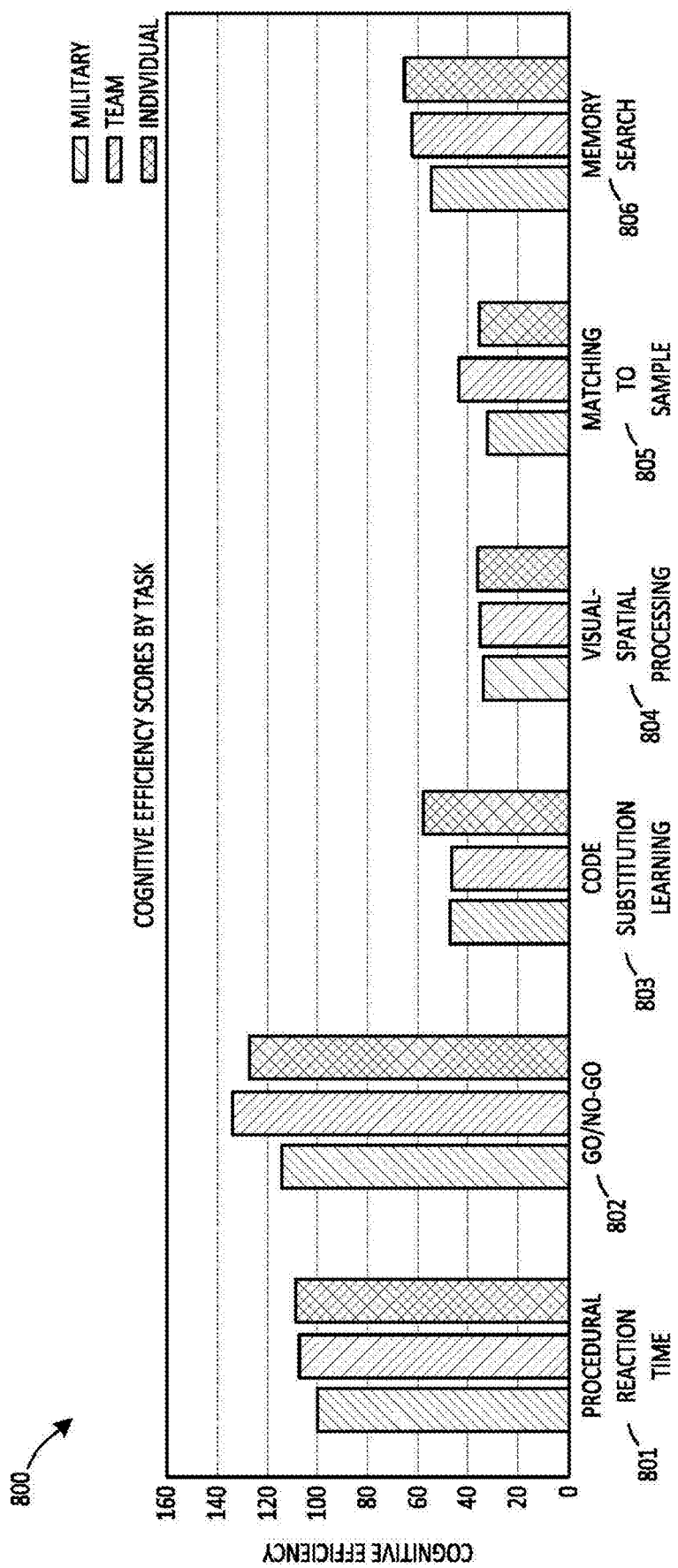
FIG. 22 is a clustered bar chart comparing the cognitive efficiencies of two groups and one individual in performing a set of tasks.

The report 161 also provides a summary and detailed review of the subject's performance on tasks or tests, as well as a review of the subject's sleep quality, levels of stress, and emotional resilience. For example, FIG. 22 illustrates a clustered bar chart 800 that appears in a group-level comparative brain training implementation of the report 161. The bar chart 800 illustrates cognitive efficiency scores (which are function of both speed and accuracy) across several tasks 801-806. The bars on the right side of each cluster show the individual's scores. The bars in the middle of each cluster show the average team score. Finally, the bars on the left side of each cluster show comparable performances by an elite team of special forces on the same tasks. In the report, the chart of FIG. 22 can be broken up into separate clusters, each of which is accompanied by an explanation of what the task reveals. For example, the report 161 may explain that simple reaction time 801 is a measure of pure reaction time and accuracy, and that Go-No-Go 802 is a measure of sustained attention and impulsivity, assessing the speed and accuracy of targets, omissions, and commissions.

Figures 23, 24:
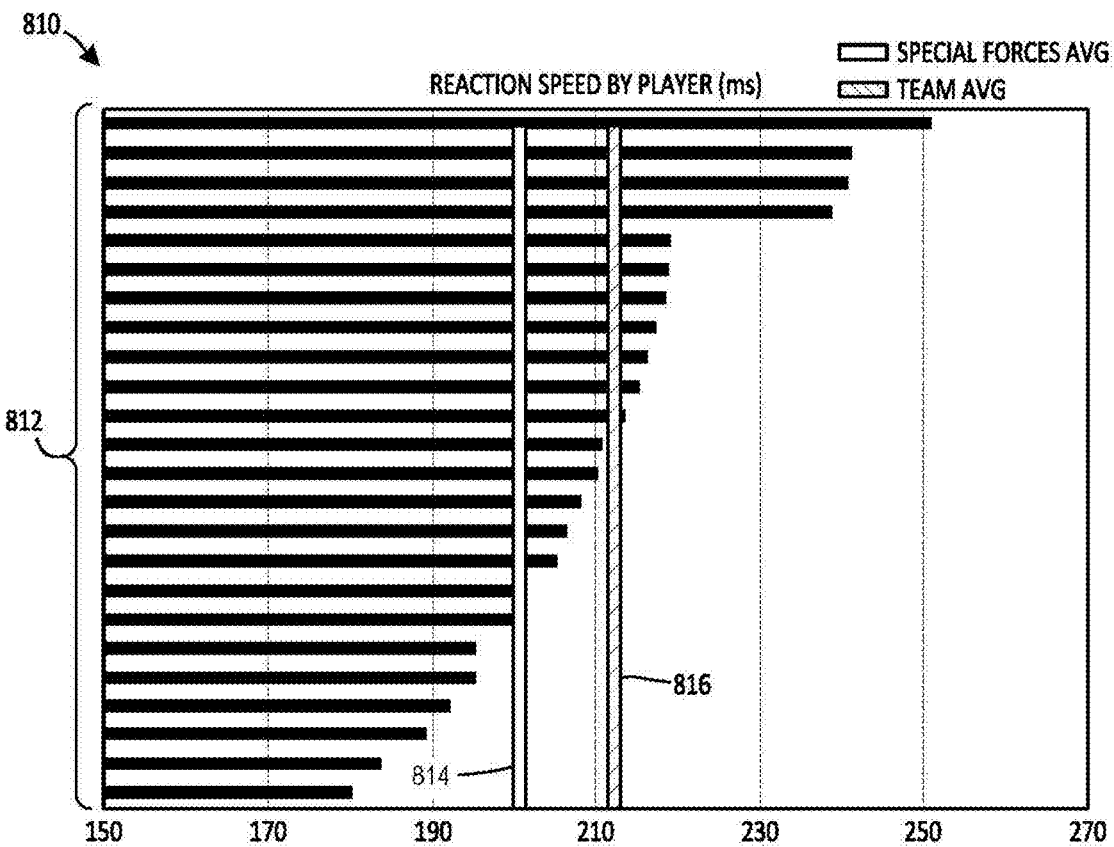
FIG. 23 is a bar chart comparing the reaction speeds of a team's players with the team average and an expert group (used as an external objective reference).
FIG. 24 is a bar chart illustrating a relationship between the reaction speeds of the team's players with the positions that they play.

FIG. 23 illustrates a player/team-member-comparative chart 810 in an embodiment of a report particularly intended for coaches, trainers, or managers. The chart 810 compares the reaction speeds of each player 812 on the team, and further compares those reaction speeds with benchmark values, such as the average speed 814 of the players on the team, the average speed 816 of an elite group such as military special forces, and/or the average speed of a population of normal, healthy adults. In one implementation, not shown in the drawings, two sets of bars are provided for the player or team member for showing their reaction speeds both before and after completing some cognitively demanding tasks. This illustrates the impact that occurs in the players'/team-members' brains from cognitive fatigue.

FIG. 24 illustrates a chart 820 that groups the players/team-members according to their positions (e.g., backs 822, forwards 824, military 825, spine-no 826 and spine-yes 828; in a corporate environment, these groups might be programmers, designers, salespeople, those in marketing, etc.) in the sport/corporate environment and illustrates the average cognitive efficiency score for each group. In this example of Rugby players, backs and spine players are shown to perform better than forwards in tests for visual spatial memory and pattern recognition.

Figure 25:
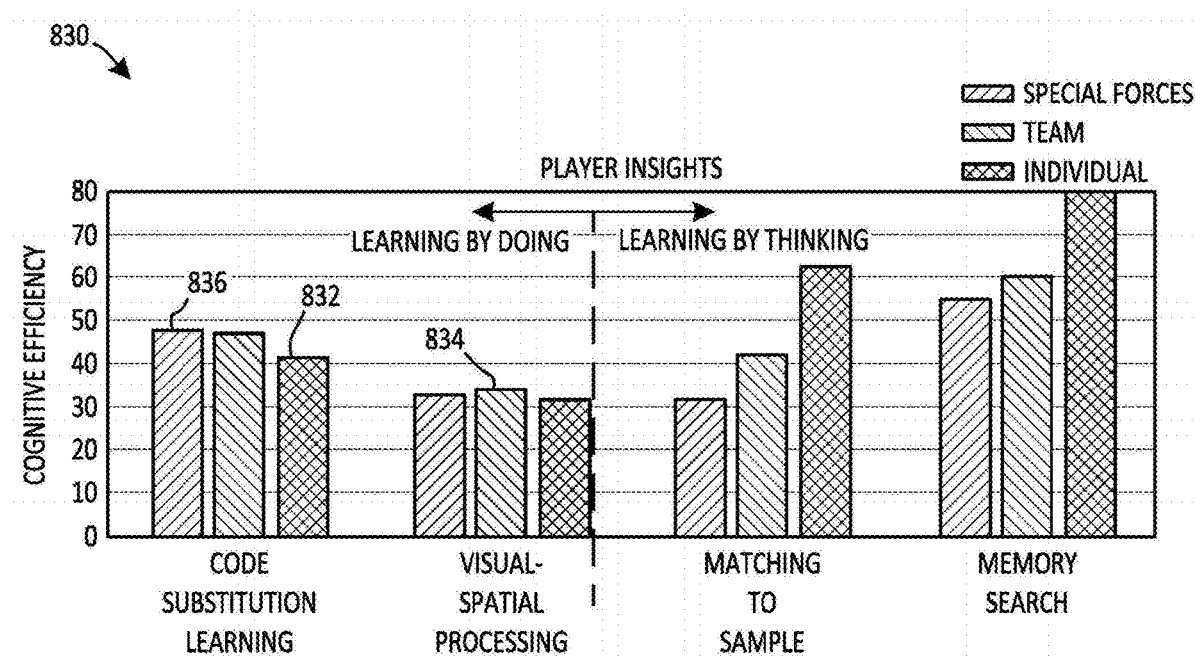
FIG. 25 is a clustered bar chart illustrating how one player's strengths lie in tasks that involve learning by thinking as opposed to learning by doing.

FIG. 25 illustrates a clustered bar chart 830 that compares the performances of an individual player/team-member 832, the team 834, and an elite military group 836 on code substitution learning, visual-spatial processing, matching to sample, and memory search tasks. The player/team-member in this example has a clear learning-by-thinking preference. This indicates that the player/team-member is more information driven and would benefit most from that type of coaching approach. This aids a coach, trainer, or manager in determining the relative importance and prevalence of different cognitive skills for each position/role.

In one implementation, the report 161 states that the subject has high levels of stress on a daily basis. Or it can state that the subject showed resilience to adverse events like a missed shot, an unforced error, or a bad call. In a sports implementation, NEPAS 100 might require either human input or game data from a game statistician, or a machine learning program that has image processed and analyzed the game, to produce the game data. The report 161 also describes each of the tasks or tests and explains which aspects of cognitive skill they reveal.

The report 161 also includes one or more images or videos, or one or more links thereto, of the subject's brain activity during a task and/or during a baseline task in which the subject rested with closed eyes. In one implementation shown in FIGS. 2 and 3, at least two images of the brain, one image 170 illustrating regions of the brain that are more active, and the second image 171 illustrating pathways in a manner that reveals their connectivity strength. Alternatively, the video can show side-by-side images of the subject's brain and a normal, expert, or ideal brain performing a task. In yet another alternative, the video can show a map or graph illustrating the state and/or functional connectivity of the subject's brain.

Figure 26:
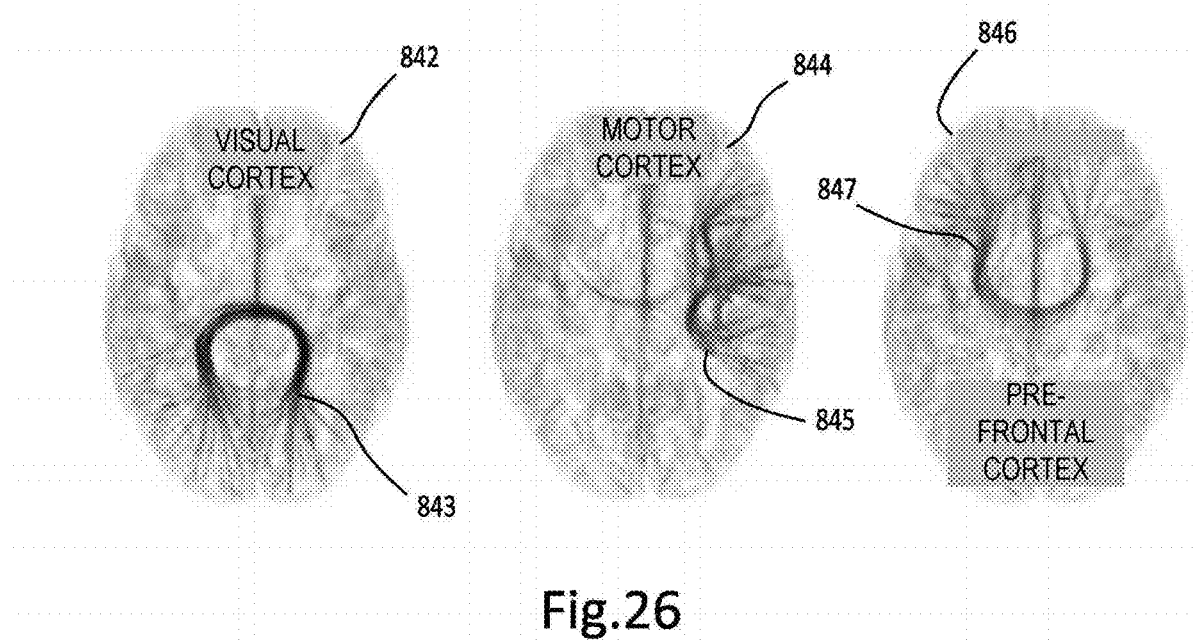
FIG. 26 are brain images that illustrate pathways in three principal brain regions of interest—the visual cortex, the motor cortex, and pre-frontal cortex.

FIG. 26, for example, illustrates three brain images 842, 844, and 846 from the prior art whose darker areas represent three brain regions of interest—the visual cortex 843, the motor cortex 845, and the pre-frontal cortex 846. The report 161 can include similar images with color, breadth and/or brightness to illustrate the strength of key inter-cortical pathways for a player, team-member, trader, salesperson, or other subject.

In another implementation, the report 161 identifies physiological (including neurophysiological) characteristics that are correlated with aspects of the subject's performance.

In one implementation, data processed using PCA and/or ICA is used to generate 3D maps or graphs illustrating the state and/or functional connectivity of the subject's brain and/or 3D maps or graphs that use color, brightness, and/or thickness to illustrate a ratio or other comparison between the pathways' task-state power values and the baseline power values.

The report 161 explains and/or displays how the subject's physiological and neurophysiological data, as well as the subject's self-reported characteristics on attention, distractibility, workload, and sleep deprivation are correlated with the subject's performance. In one implementation, the report 161 provides one of four observations based upon a comparison between simple reaction times for the first and last tasks of a session or day, where the subject also performed a series of cognitively challenging tasks in between: (1) both tasks were performed within normal limits and there was no significant difference in reaction times (meaning cognitive endurance was maintained), (2) both tasks were performed within normal limits but reaction times for the first task were better than for the last task (meaning cognitive fatigue occurred), (3) both tasks were performed within normal limits but reaction times for the last task were better than for the first task (meaning the participant could have benefited from a cognitive warm-up), and (4) one or both of the tasks was below normal limits (meaning that intervention is needed and cognitive reserve is depleted).

The report 161 also describes and graphically illustrates how the subject's measured cognitive efficiency, procedural reaction time, and go/no-go performance compares with that of one or more populations of persons. In one implementation, the report 161 includes brain activity images of the subject's brain. Another implementation of the report 161 adds a comparative view of brain activity representative of the population or a population norm. In another implementation, the report 161 includes contrasting images of the person's brain activity before and after performing the task a single time, or before and after performing the tasks over N repetitions, where N is greater than or equal to 1.

Moreover, the report 161 provides an inferential analysis of the integrity of the subject's brain systems, including a comparative assessment of the number of links or axon-formed connections in a relevant brain pathway and an assessment of the relative speed and bandwidth of the relative brain pathway.

Furthermore, the report 161 describes how the subject can get or keep his/her brain in optimal readiness and condition. For example, the report 161 describes ways in which the subject can get a full night's sleep, manage stress, and become more resilient. The report 161 can also provide a person with a reasonable achievement goal that includes an illustration of a sought-after brain signature. Finally, the report 161 also describes an optimized training regimen and schedule for the subject, or simply states that an optimized training regimen can be prepared.

In another embodiment, parts or all of the subject matter described in the report 161 are also displayed to the subject while the subject is performing the task.

As noted above, the reporting engine 160 generates reports 161 for both the individual and a third party (such as a coach, trainer or manager). The subject or a third party accesses the reports 161 through a data and report access portal 163. In one implementation, the data and report access portal 163 provides access to a dashboard 905 (FIG. 30) that includes visualizations 906-909 of the subject's physiological data 102. For the example, a brain state connectivity/brain wave correlation chart 906 would show the subject how active and focused their brain is. An efficiency bar graph 907 would show the subject variations across time in the subject's brain efficiency. A heart rate graph 908 would help the subject keep track of his/her heart rate. And a heart rate variability graph 909 would show the subject how significantly his/her heart rate is fluctuating. Other graphs (not shown) would show the subject how well their recent executions have performed relative to a benchmark.

It is contemplated that the elements of the dashboard 905 could fill the entire screen or a portion of the screen, such as a side bar or a bottom bar that extends along the length of the monitor 902.

In one implementation, different levels of access to the data 101 and 102 are provided. For example, a player or researcher might get access to the neurophysiological data 102 at a resolution of 60 Hz, a coach or personal trainer at a resolution of 20 Hz, or the league at a resolution of 1 Hz.

When NEPAS 100 is applied to sports training, the report 161 provides a high level of insight that coaches are very interested in obtaining and that can lead to interventions and boost strategies. NEPAS 100 recognizes and describes a pattern that goes with the behavior or state (e.g., emotional resilience) that is relevant to the coach. NEPAS 100 selects a recipe or regimen of tasks to address that behavior or state. For example, the regimen can include a warm-up of Posit Science tasks, Neurotracker, and baseline tasks to improve subsequent sports performance or can include a cool-down of meditative and neurofeedback tasks to allow an elite performer to down-regulate their emotional system after a highly competitive performance.

When NEPAS 100 is applied to corporate teamwork or financial trading, the reports 161 provide similarly high levels of insight for team managers or risk managers. NEPAS 100 recognizes and describes patters that go with brain states that are relevant to mediocre, average, and/or high performance. NEPAS 100 selects a recipe or regimen of tasks to address that behavior or state.

The decision engine 143 uses the data to program a task controller 143, a neurofeedback interface 144, and an intervention planner and evaluator 147. The task controller 143 modifies sensory stimulation or cognitive tasks and/or programs of training as a function of both the performance data and the neurophysiological data, and optionally also as a function of the physiological data. For example, adjustments could reduce or increase the attentional requirements of the task. In one implementation, the modifications are automatic and implemented in real time, while a task is being performed. In another implementation, the modifications are made to tasks subsequent to the one currently being performed.

In one implementation, the decision engine 160 identifies changes in the data 101, 102, or 103, or a running average of that data 101, 102, or 103, that exceed a predetermined threshold for a group or team of performers. Modifications to the individual are determined to benefit the overall group's performance. Modifications are selected to help keep the group, including the subject, paced, engaged and focused while performing the task, and to counteract boredom, fatigue and burnout.

It will be noted that there is no requirement that the group be confined to a particular physical space. The group members could be dispersed geographically and in various brain states (e.g., including sleep). For example, in an E-gaming or programming environment, a subject could be stimulated out of a sleep stage in order to contribute, and contribute maximally, to a team effort in that environment.

In one implementation, the neurofeedback interface 145 is one and the same as the display interface 135. In another implementation, the neurofeedback interface 145 comprises auditory, visual, stimulatory, oral, electrical and/or intravenous implements. The neurofeedback interface 145 provides one or more of the following stimuli or substances to the subject if the system detects that brain activity, a brain activity differential, or a brain activity change at a transition within the task, in a selected brain system has fallen below a threshold:

electrical or magnetic stimulation administered to the subject's head;
a neurotropic administered orally or intravenously to the subject;
a tactile stimulation administered to the subject's body;
a transient sound; and
a transient light.

The intervention planner and evaluator 147 plans and monitors a program of training and other interventions for the subject that are designed to facilitate the subject's development of an expert-level brain state. An intervention plan can include, but is not limited, to one or more of the following: an assessment, insights for a coach or trainer, suggestions on diet and neurotropics, brain stimulation, and cognitive stimulation. Details of the intervention plan can be included in, or provided separately from, the report.

In some implementations, the behavioral task interface 110, DSPs 103 and 111, data logger and interface 140, task controller 144, neurofeedback interface 145, intervention planner and evaluator 147, statistical engine 150, reporting engine 160, and feedback display interface 135 are embodied in one or more computers and one or more software applications for performing their functions.

Figure 2:
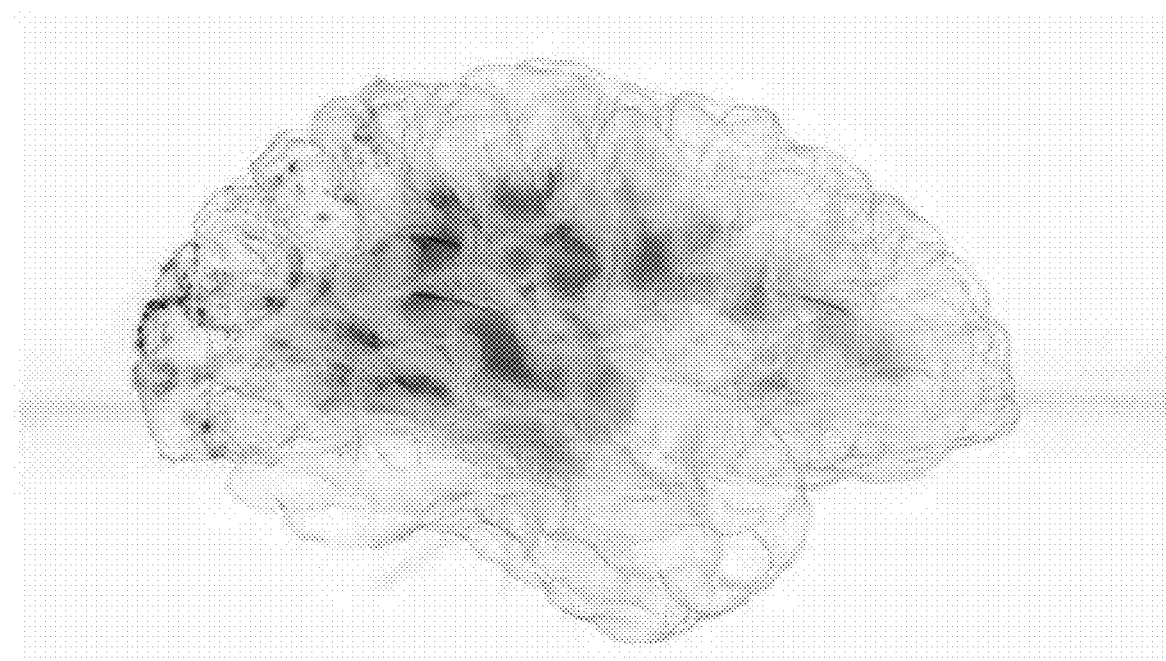
FIG. 2 illustrates one embodiment of a 3D spatial representation of a brain with extra-active pathways illuminated, oriented with a side view perspective.
Figure 3:
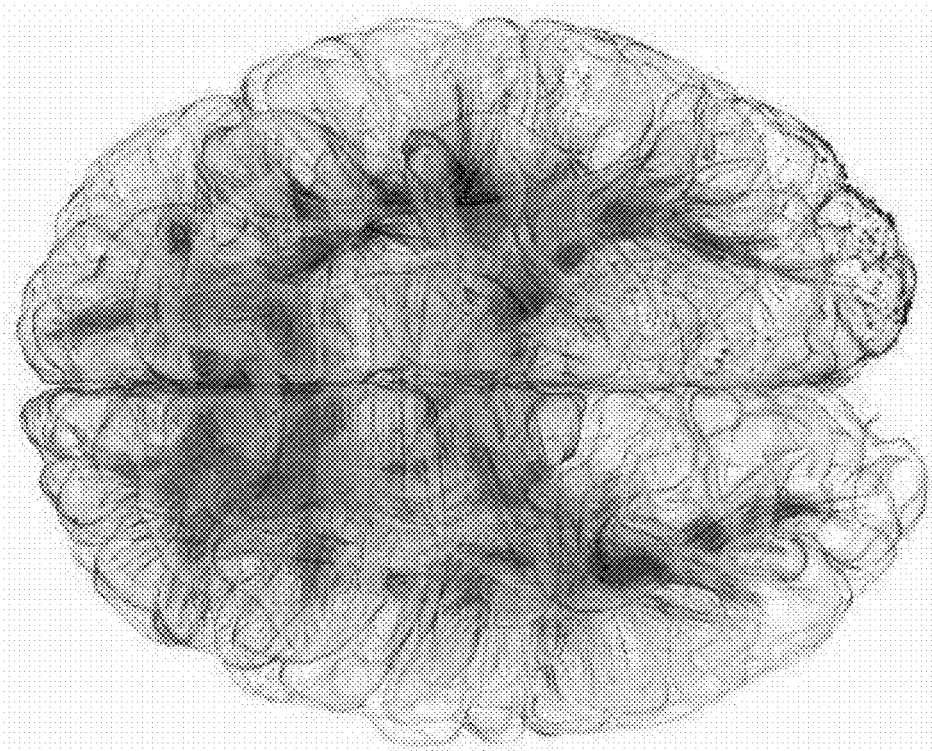
FIG. 3 illustrates one embodiment of a 3D spatial representation of a brain with extra-active pathways illuminated, oriented with a side view perspective.
Figure 4:
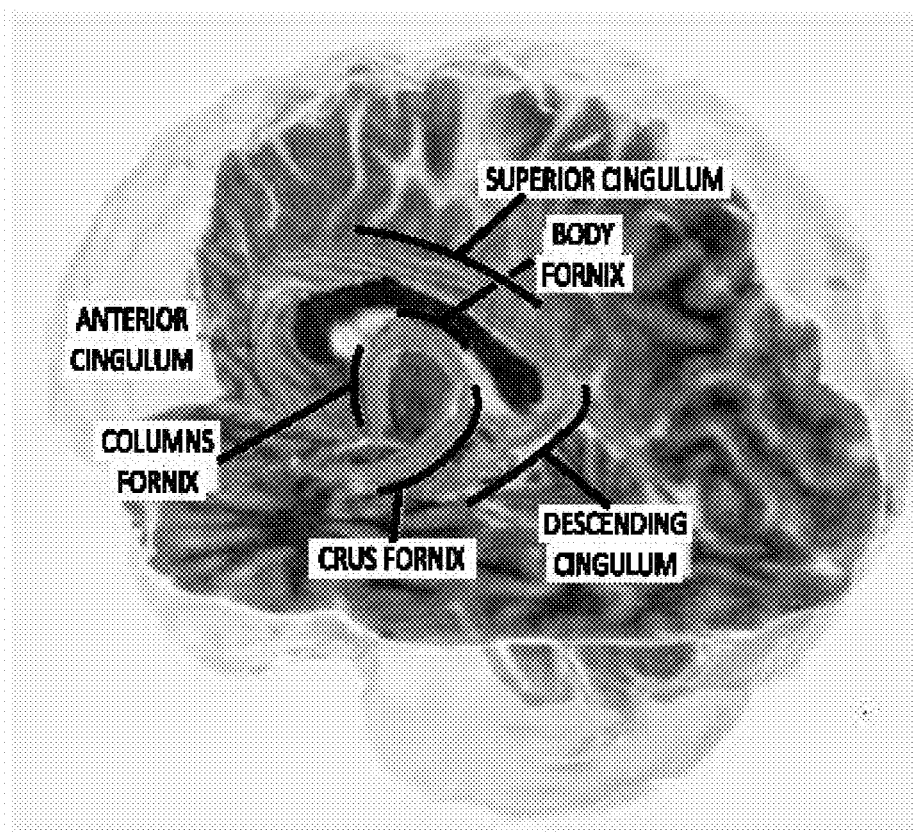
FIG. 4 illustrates one embodiment of a 3D spatial representation of brain in partial cross section illuminating selected pathways.

FIG. 2 illustrates one embodiment of a brain-mapped spatial representation 170 of brain activity, oriented to provide a side view perspective. The darker areas represent high activity. FIG. 3 illustrates another embodiment of a brain-mapped spatial representation 172 of the brain, oriented to provide a top-view perspective. In FIGS. 2 and 3, especially activated (i.e., differentially and positively activated, as compared to a baseline) pathways are illuminated, illustrating the strength and multiplicity of neural links between regions of the brain. A brain-mapped spatial representation 170 can display only selected regions of the brain. Certain exterior regions can be removed from view, as they are in FIG. 4, to better illustrate selected brain regions and pathways.

Brain-mapped spatial representations 170 and 172 can be generated using principal component analysis (PCA), independent component analysis (ICA), or other data transforms such as sparse and low-rank matrix decomposition, t-Distributed Stochastic Neighbor Embedding (tSNE), etc.

Figure 5:
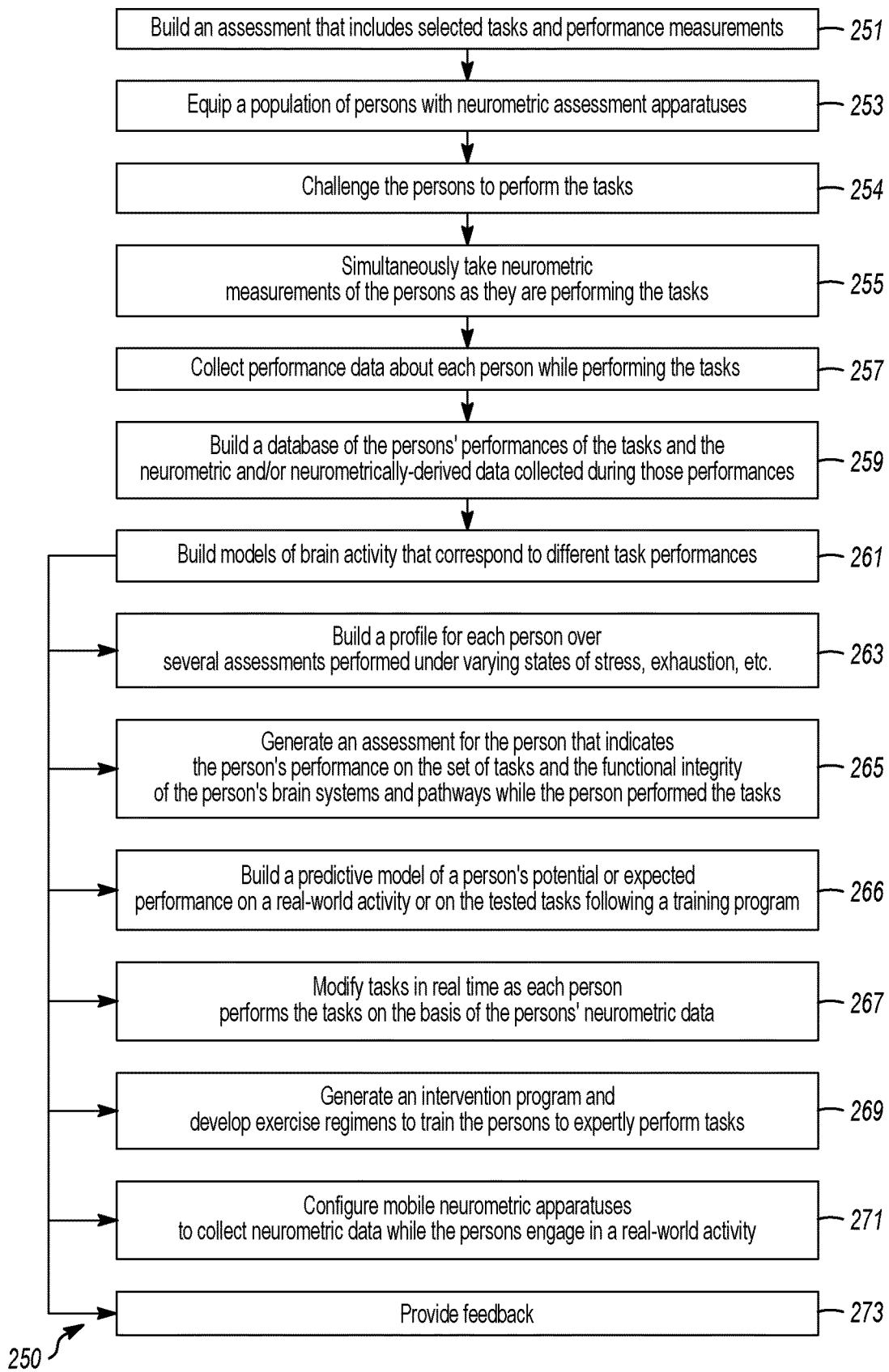
FIG. 5 illustrates one embodiment of a method of building a neurometric apparatus for enhancing a person's performance.

FIG. 5 illustrates an embodiment of a method 250 of constructing a neurometric apparatus to monitor, analyze, and/or enhance performance in a person or population of persons. The population of persons can consist or essentially consist of members of a team, an elite group, or a representative sample of the general population.

In block 251, select tasks that differentially recruit (i.e., preferentially activate or induce comparatively significant change, in a neuroscientifically distinguishable manner) selected systems, regions and/or pathways of the brain to incorporate into the assessment. Tasks can be selected to target a cognitive domain and detect abrupt brain activity changes in the person in an area associated with the cognitive domain. Such tasks are then used to indicate the integrity of specific systems of the brain. Also, select different types of tasks, such as at least one motor-behavioral task, at least one cognitively/neuropsychologically important task, at least one experiential task that the person performs in an unconfined or virtual-reality setting, and a survey-completion task. For example, the virtual-reality setting can provide a virtual representation of real settings such as golf courses, stadiums, fields, work environments, etc. Equip the person or configure a machine or computer interface to collect performance metrics while the person performs the tasks. Actions performed in the tasks should be detectable not only in a traditional way, such as through computer inputs, timers, force measurements, etc., but also through neurophysiological sensors that detect brain activity.

In block 253, equip the persons with neurometric apparatuses comprising neurophysiological sensors of brain activity. A neurometric apparatus can be formed as a neurophysiological head-mounted accessory such as a headset, a headband, a hat, helmet, or other item of apparel or device configured to be worn on the head and including a plurality of neurophysiological sensors configured to sense brain activity. In block 254, challenge the persons to perform the tasks. In one implementation, the first time a person performs the tasks, the performance data 101, neurophysiological data 102, and physiological data 103 are used to establish a baseline. This baseline is used to identify systems of the brain at which to target training.

In block 255, take neurometric measurements of each person both before and as he/she performs the tasks, and transmit the neurometric data to a record. In one implementation, neurometric measurements are taken before the tasks to evaluate the person's default mode network for a period in which the person is asked to do nothing but to lie quietly while staying awake. A representation of the person's brain activity when the default mode network is activated is used as a baseline against which the person's brain activity while performing the tasks is measured. In block 257, collect performance data about each person while the person performs the tasks, or after each task is or all of the tasks are completed, and transmit the performance data to the recorder. The neurometric data is synchronized with the performance data.

In block 259, build a database of the persons' performances of the tasks and the physiological and neurophysiological data (or information derived from such data) collected during those performances. Also identify correlations between the performance data and the neurometric data to construct a functional assessment of neurophysiological functions of the brain's highways from the neurometric data. To create a functional assessment, use baseline conditions or baseline stimuli and set ranges of brain activity during a brain state to determine training levels in subsequent tasks. For example, record the person's brain activity while resting to determine an average amount of energy in a specific frequency using specific scalp locations, and also record the person's brain activity while watching a video. When the person's brain activity drops below a level or a threshold—within a standard deviation (for example) of the person's resting level—use this level as a key performance indicator (KPI) of when the person is not engaged. When the person's brain activity pattern exceeds this resting activity range then assign the cognitive state of low, medium or high engagement based when compared to the resting state.

In block 261, query the database for data with which to build one or models. One model relates different types of brain activity in different regions and pathways of the brain to task performances. Another model is a 3D signature or model of brain activity corresponding to different task performances. The model or signature can be a statistical one based on a PCA and/or ICA of the data. In one implementation, multiple signatures are constructed associated with expert performance across a plurality of cognitive domains, with each signature representing expert performance in a particular cognitive domain. A person's brain activity while performing a task is compared with a corresponding signature to assess the integrity of the person's relevant brain regions and pathways.

Blocks 263-273 represent additional actions that are performed in various embodiments of the invention. All, some, or none of these actions can be included in the method 250.

In block 263, query the database for data with which to build profiles for the persons over several assessments that are conducted while the persons endure varying states of stress, exhaustion, emotional valence, etc. In block 265, generate an assessment for the person that indicates the person's performance on the tasks and describes a physiological and neurophysiological state of the subject based on the subject's performance and neurometric data. In one implementation, the assessment also assesses and illustrates, with mapped brain images, the functional integrity of the person's brain systems and pathways while the person performed the task. In block 266, build a predictive model that predicts the person's expected immediate and long-term performance and rate of progress on a related real-world activity or on the tested tasks themselves. In one implementation, an aspirational model of the person's brain activity when performing the tasks or real-world activity is presented. This can be in the form of a 3D representation of brain connectivity. The aspirational model, which is statistically based on empirical data derived from the database 141 for a whole population of persons, indicates how much the person's brain activity is expected to improve if the person completes a program of training. This aspirational model can be based upon a median of recorded brain activity improvements for persons who have completed the program of training.

In block 267, modify tasks in real time as each person performs the tasks, with the modification being a function of the person's neurometric data and optionally also the person's performance data. In block 269, generate an intervention plan, including recommendations for coaches or trainers and a customized, individual-specific training program that provides exercise regimens to train each person to expertly perform tasks.

In block 271, configure a mobile neurometric apparatus to collect neurometric data while the persons engage in a real-world activity, while another person or an interface records time-stamped observations about that activity. Examples of real-world activities include playing a sport, engaging in financial transactions in the open market, performing music, competing in a game, and performing a work task. In this manner, a person can be assessed while performing a work task, and then a training program can be created to help improve the person's productivity or to reach an expert state.

In block 273, provide feedback to each person as the person performs the real-world activity. Feedback can be provided on not only the person's performance but also the persons' cognitive states, wherein the feedback includes suggestions to improve the person's cognitive state in order to improve the person's performance. Feedback can also include comparisons of the person's scores with that of a team or greater population. Feedback can also comprise periodically updated predictions of how much longer the person will need to practice the training tasks to achieve the preselected level of proficiency (see FIG. 17). In a virtual-reality environment, the feedback can include information, graphs, tables, and/or imagery about the person's brain state which is incorporated into the virtual reality construct, which itself can be a construct of real settings such as golf courses and stadiums.

Figure 6:
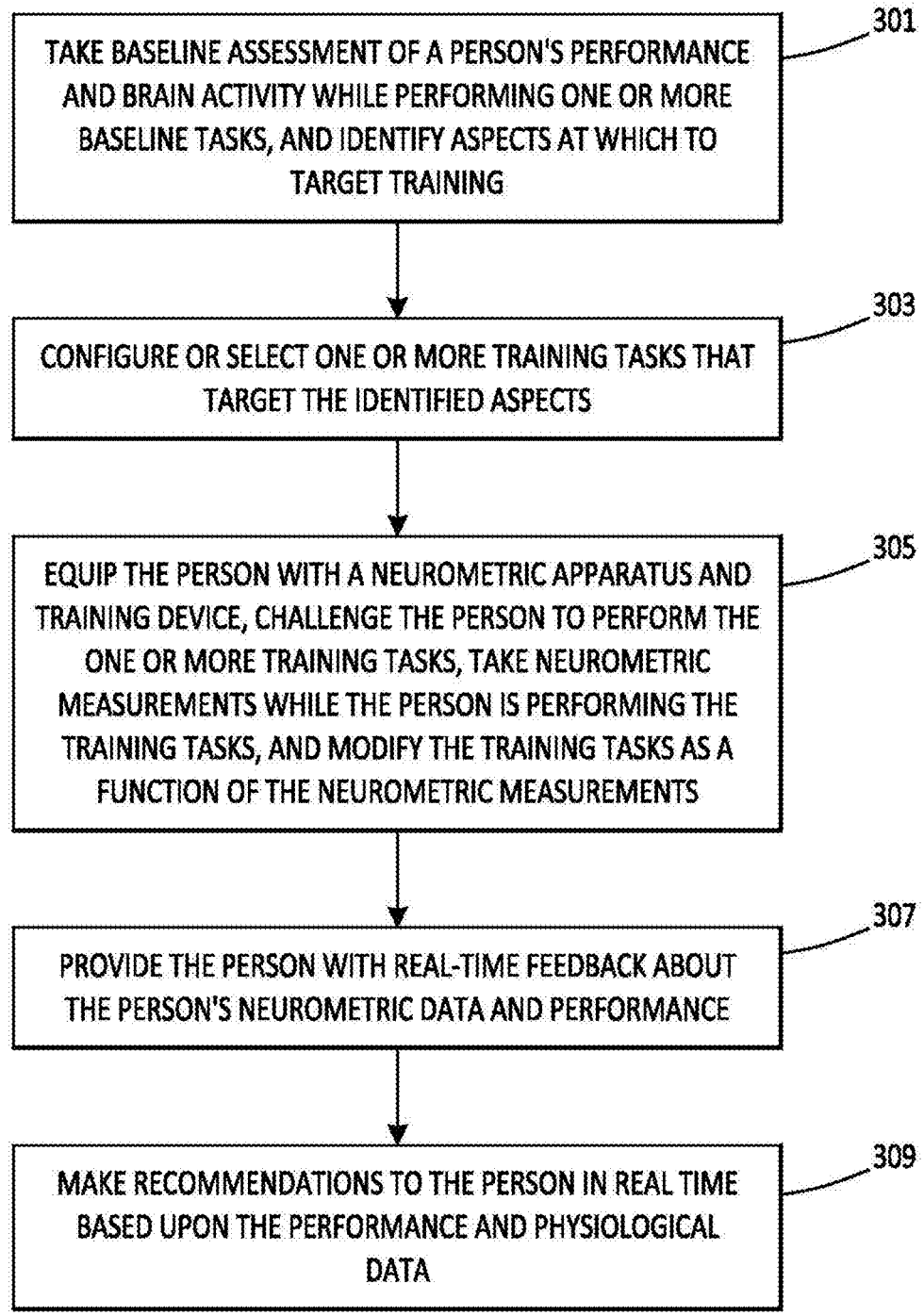
FIG. 6 illustrates one embodiment of a method of rapidly enhancing a person's performance.

FIG. 6 illustrates one embodiment of a method of rapidly enhancing a subject's performance. In block 301, take a baseline assessment of a subject's performance and brain activity while the subject performs one or more baseline tasks. Identify brain systems with subpar or suboptimal brain activity during the subject's performance of the activity. In block 303, configure or select one or more training tasks that target the identified area. Examples of training tasks include cognitive warmups, visual speed training, meditation/mindfulness, stress and recovery training. In the sports training context, cognitive warmups are daily warmups to prime the brain for practice and gameplay, focusing on improving attention, brain speed, memory, emotional recognition skills, intelligence, and navigation.

In block 305, equip the subject with a neurometric apparatus and training device, wherein the neurometric apparatus takes neurometric measurements while the subject is performing a training task. The training device challenges the subject to perform the one or more training tasks and modifies the one or more training tasks as a function of the neurometric measurements. In block 307, provide the subject with real-time feedback about the subject's neurometric data and performance. In block 309, make recommendations to the subject, optionally in real time, based upon the performance and physiological data.

Figure 7:
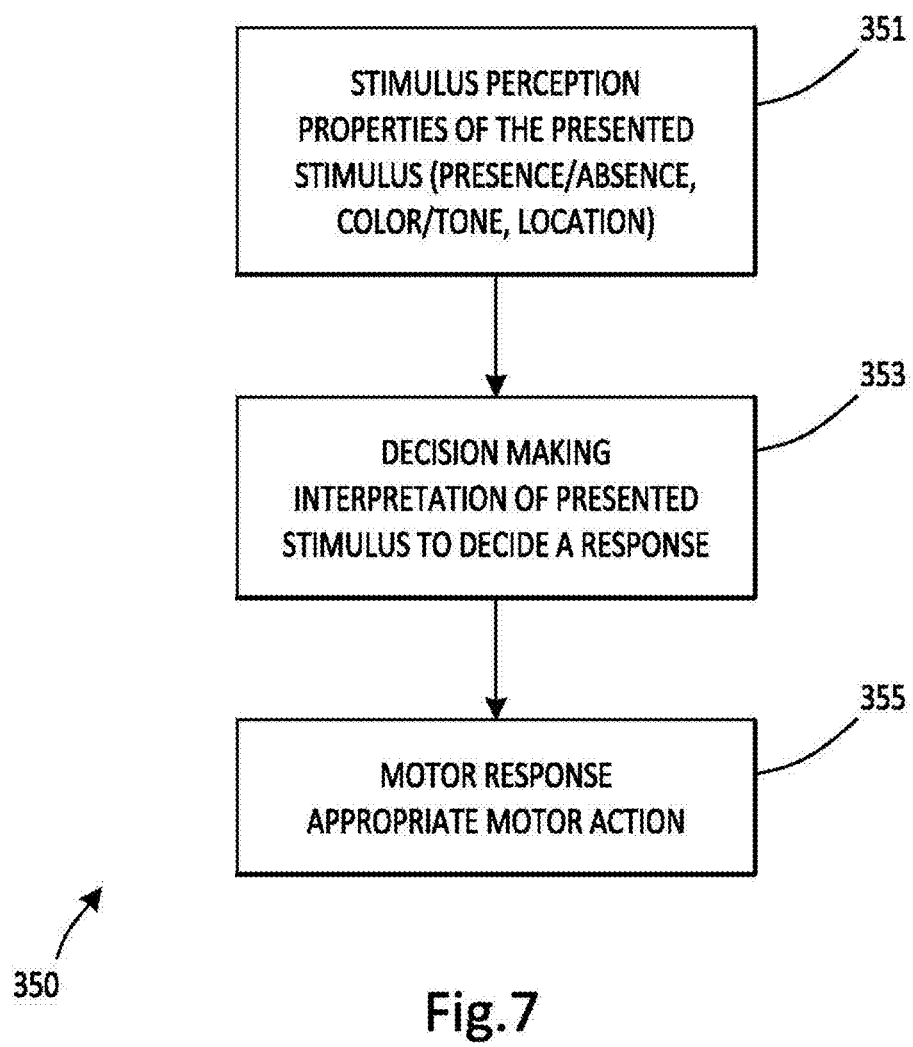
FIG. 7 illustrates three main assessment focal points for producing one embodiment of a measure of cognitive efficiency.

FIG. 7 illustrates three main assessment focal points 350 for producing one embodiment of a measure of cognitive efficiency. They are stimulus perception 351, decision making 353, and motor response 355. Stimulus perception 351 involves various properties that a subject perceives about a stimulus, such as presence/absent, color/tone, and location. Decision making 353 involves interpretations the subject makes of the presented stimulus to decide a response. Motor response 355 involves making appropriate motor actions in response to instructions.

Figure 8:
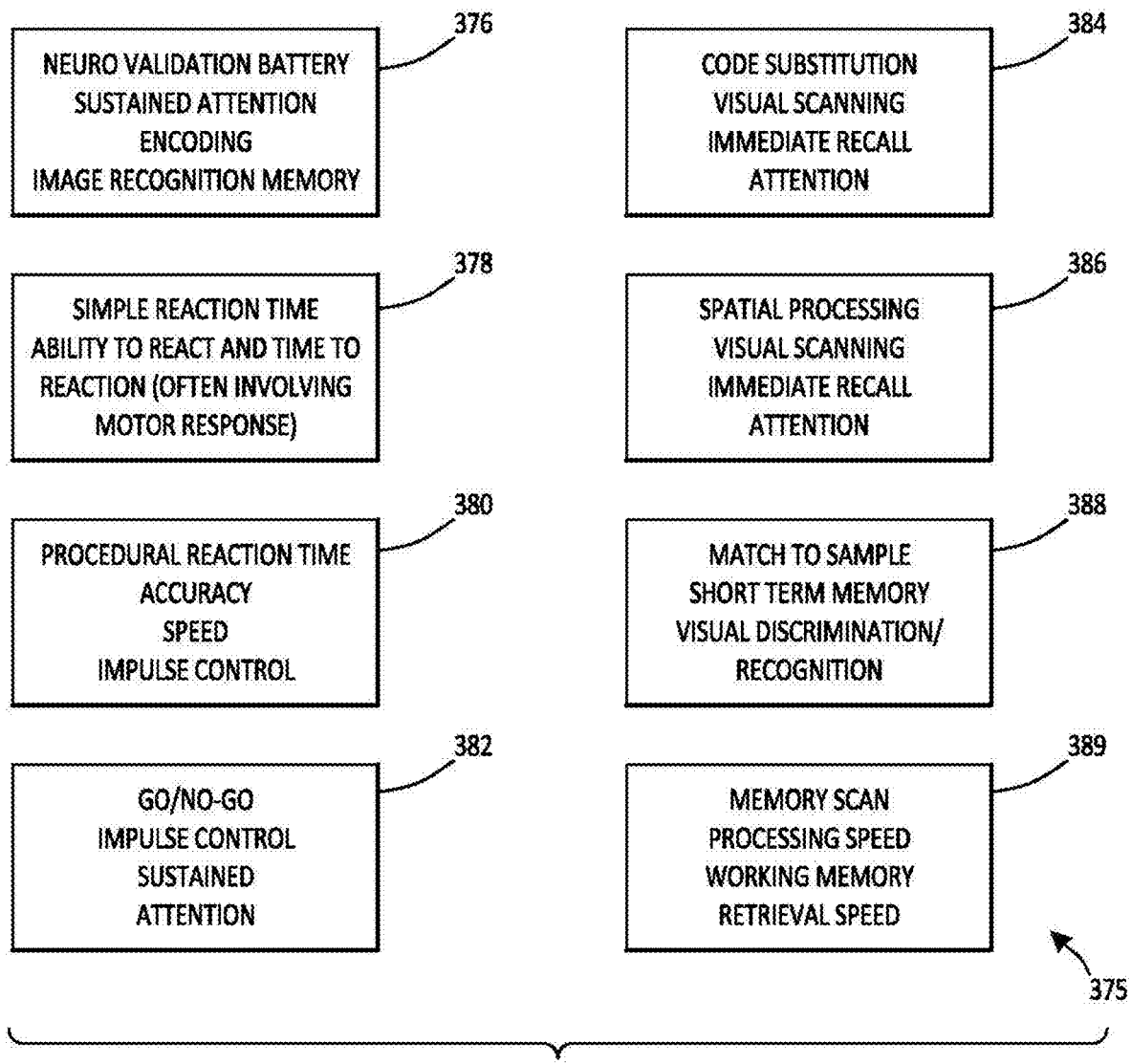
FIG. 8 illustrates one embodiment of a battery of assessment tasks.

FIG. 8 illustrates one embodiment of a bundle 375 of assessment tasks. The bundle 375 includes a neuro validation battery 376, a simple reaction time task 378, a procedural reaction time task 380, a go/no-go task 382, a code substitution task 384, a spatial processing task 386, a match to sample task 388, a memory search task 389, and another simple reaction time task 378 to measure reaction time after the rest of the tasks are completed. The neuro validation battery 376 comprises a sustained attention task, an encoding task, and an image recognition memory task.

Table 1 below describes a set of specific exercises subjects are tasked with doing in one implementation of the bundle 375.

TABLE 1

One embodiment of a set of assessment tasks

| Test Name | Task Description |
| --- | --- |
| Simple Reaction Time (SRT1) | Recognize the presence of an object and tap the object |
| Procedural Reaction Time (PRT) | Recognized 1 of 4 numbers and tap 1 of 2 buttons |
| Go/No-Go Task (GNG) | Recognize a green or gray object and only tap in response to gray. |
| Code Substitution Learning (CSL) | Recognize whether or not a symbol-digit pair matches the key code shown and tap "Yes" or "No" |
| Spatial Processing (SP) | Recognize rotation of a visual object and tap "same" or "different" |
| Matching to Sample (M2S) | Recall a 4 × 4 checkerboard pattern after it disappears for 5 seconds and two options appear |
| Memory Search (MS) | Recognize letters that have been previously memorized |
| Simple Reaction Time (SRT2) | Recognize the presence of an object and tap the object (after ~15 minutes of cognitive exertion) |

The simple reaction time task 378, often involving a motor response, measures the ability to react and time to reaction. The procedural reaction time task 380 tests accuracy, speed, and impulse control. The go/no-go task 382 tests impulse control and sustained attention. The code substitution task 384 tests visual scanning, immediate recall, and attention. The spatial processing task 386 tests visual scanning, immediate recall, and attention. In one implementation, the spatial processing task 386 challenges a participant to track multiple targets moving dynamically in 3D space.

The match to sample task 388 tests short term memory and visual discrimination and recognition. The memory search task 389 provides measures of processing speed and working memory retrieval speed. In one implementation, a subject's results on these tasks are incorporated into a report 161, along with a color-coded brain image that use warmer colors to encode areas of greater brain energy, and a brain connectivity map with lines whose size and color indicate brain connectivity strength.

Another embodiment of a bundle of assessment tasks comprises the battery of eight (8) cognitive tests (code substitution, matching sample, memory search, etc.) and seven (7) psychological surveys set forth in the Defense Automated Neurobehavioral Assessment (DANA). DANA typically takes about 20 minutes to complete and provides an automatic report which can be incorporated into NEPAS 100's report 161.

Figure 9:
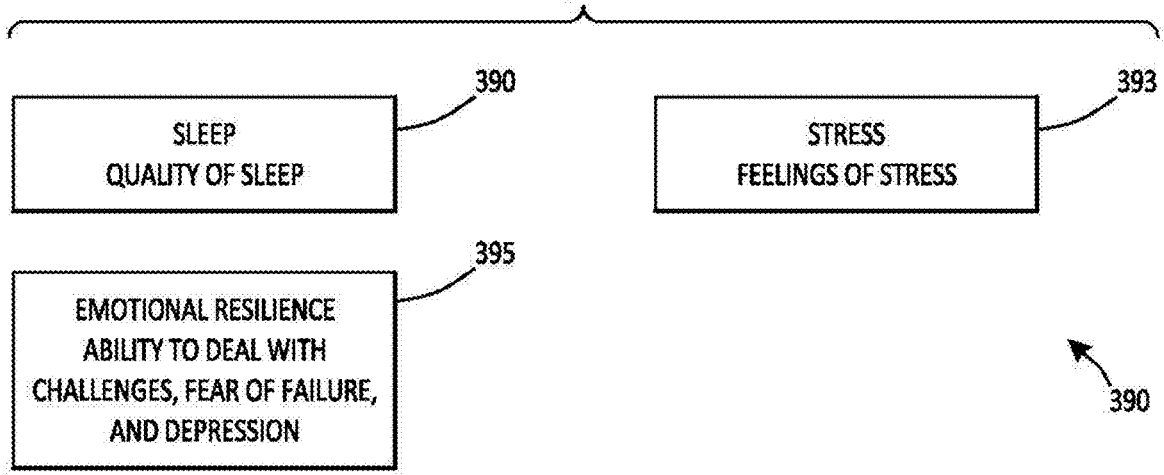
FIG. 9 illustrates components of one embodiment of a behavioral assessment.

FIG. 9 illustrates components of one embodiment of a behavioral assessment 390. The behavioral assessment 390 assesses a subject's sleep quality 391, feelings of stress 393, and emotional resilience 395. Emotional resilience 395 refers to the ability to deal with challenges that can take many different forms, including for example, fear of failure, exhaustion, frustration, adversity, criticism, humiliation, and depression.

Figure 10:
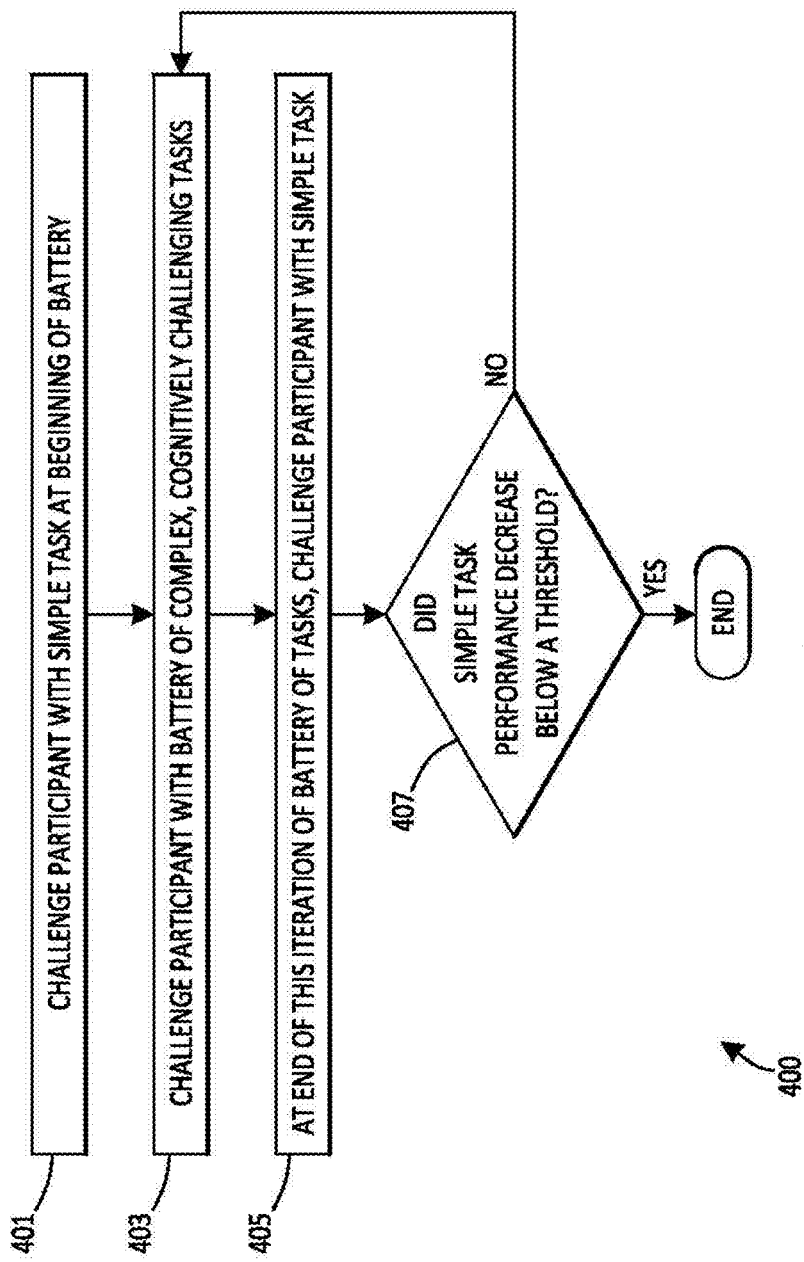
FIG. 10 illustrates one embodiment of a method of assessing cognitive reserve.

FIG. 10 illustrates one embodiment of a method 400 of assessing cognitive reserve. In step 401, challenge the participant with simple task at the beginning of an assessment. Afterwards, in step 403, challenge the participant with a battery of complex, cognitively challenging tasks. Then, in step 405, at end of the completion of one iteration of the battery of tasks, challenge the participant, once again, with a simple task. In step 407, compare the before and after simple task performances. If the post-battery simple task performance dropped at least a threshold amount below the pre-battery simple task performance, the process returns to step 403.

Figure 11:
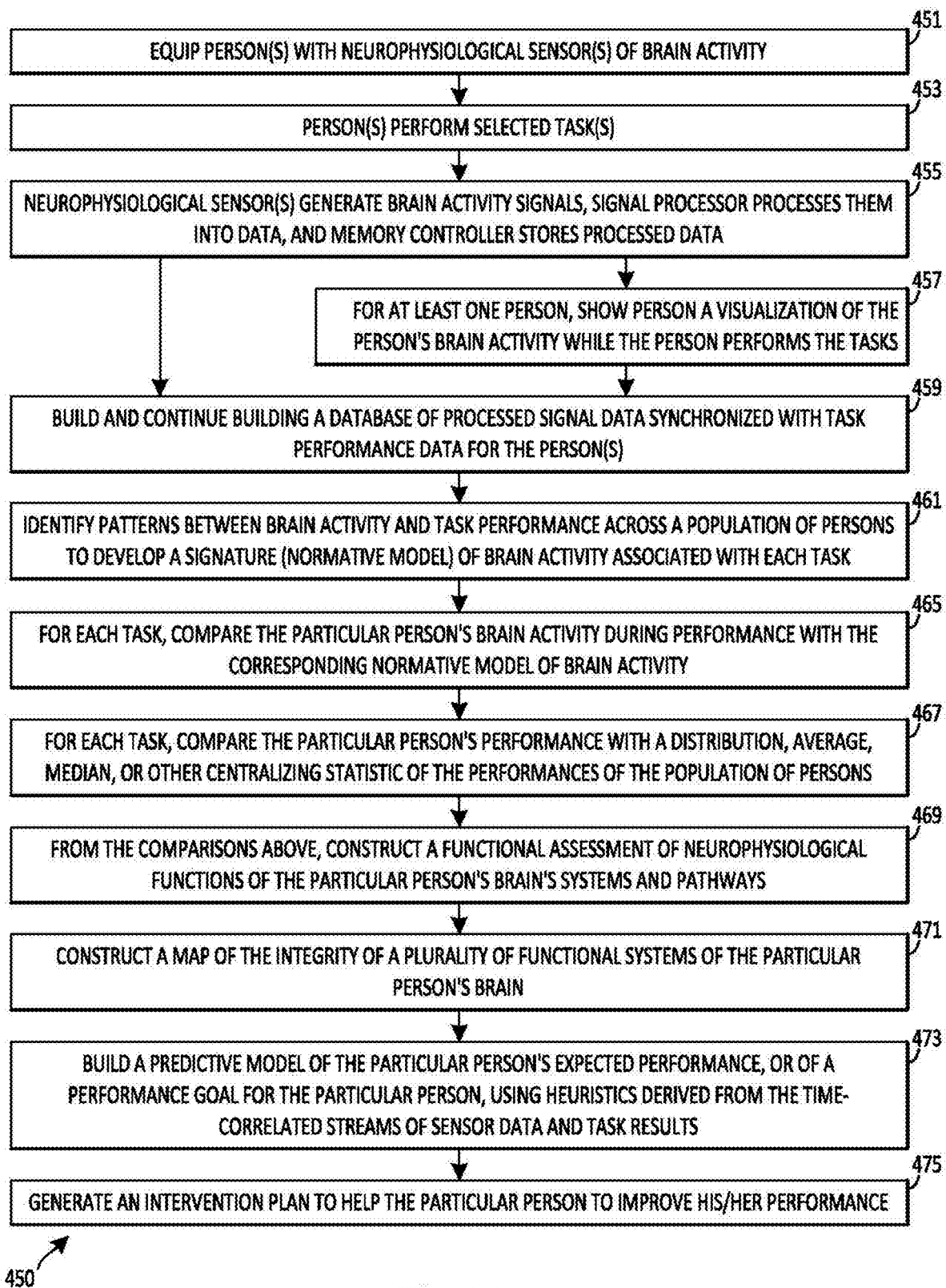
FIG. 11 illustrates one embodiment of a neurocognitive assessment and closed-loop feedback system that illustrates a subject's brain activity while the subject performs tasks, creates signatures of brain activity associated with different tasks, compares the subject's brain activity with those of a larger population, constructs a functional assessment and map of a subject's brain systems and pathways, and generates an intervention plan for the subject.

FIG. 11 illustrates one embodiment of a holistic neurocognitive assessment, training, and closed-loop feedback method 450 for illustrating a subject's brain activity while the subject performs tasks, creating signatures of brain activity or functional connectivity associated with different tasks, comparing the subject's brain activity with those of a larger population, constructing a functional assessment, and map of a subject's brain systems and pathways, and generating an intervention plan for the subject.

In block 451, equip one or more participants with neurophysiological sensors of brain activity. In block 453, the participant(s) perform(s) a series of selected tasks. In block 455, the neurophysiological sensor(s) generate brain activity signals, a signal processor processes them into data, and a memory controller stores the processed data. In block 457, show each participant a visualization of the participant's brain activity while the subject performs the tasks.

In block 459, build or add to a database of processed signal data synchronized with task performance data for the participants. In block 461, identify patterns between brain activity and task performance across a population of participants to construct a signature (normative model) of brain activity and/or functional connectivity associated with each task. This preferably involves distinguishing brain activity in multiple networks of the brain, including not only the network associated with the task activity, but also networks associated with emotional engagement. In one embodiment, PCA and/or ICA is performed to identify such patterns.

In block 465, compare a particular subject's brain activity during task performance with the corresponding normative model of brain activity. In block 467, compare the particular subject's performance of each task with a distribution, average, median, or other centralizing statistic of the performances of the population of subjects.

In block 469, construct, from the comparisons above, a functional assessment of neurophysiological functions of the particular subject's brain's systems and pathways. In block 471, construct a map—e.g., through spectral density estimation, PCA, ICA, etc.—of the integrity of a plurality of functional systems of the particular subject's brain.

In block 473, build a predictive model of the particular subject's expected performance, or of a performance goal for the particular subject, using heuristics derived from time-correlated streams of sensor data and task results. In one implementation, the predictive model predicts how long the subject will need to practice or train to achieve a predefined level of performance or proficiency. In another implementation, the model predicts a level of performance or proficiency that the particular subject will achieve if the subject keeps training indefinitely. In yet another implementation, the model predicts an asymptotic rate of progress over time that the subject will achieve with training. In block 475, generate an intervention plan to help the particular subject to improve his/her performance.

Figure 12:
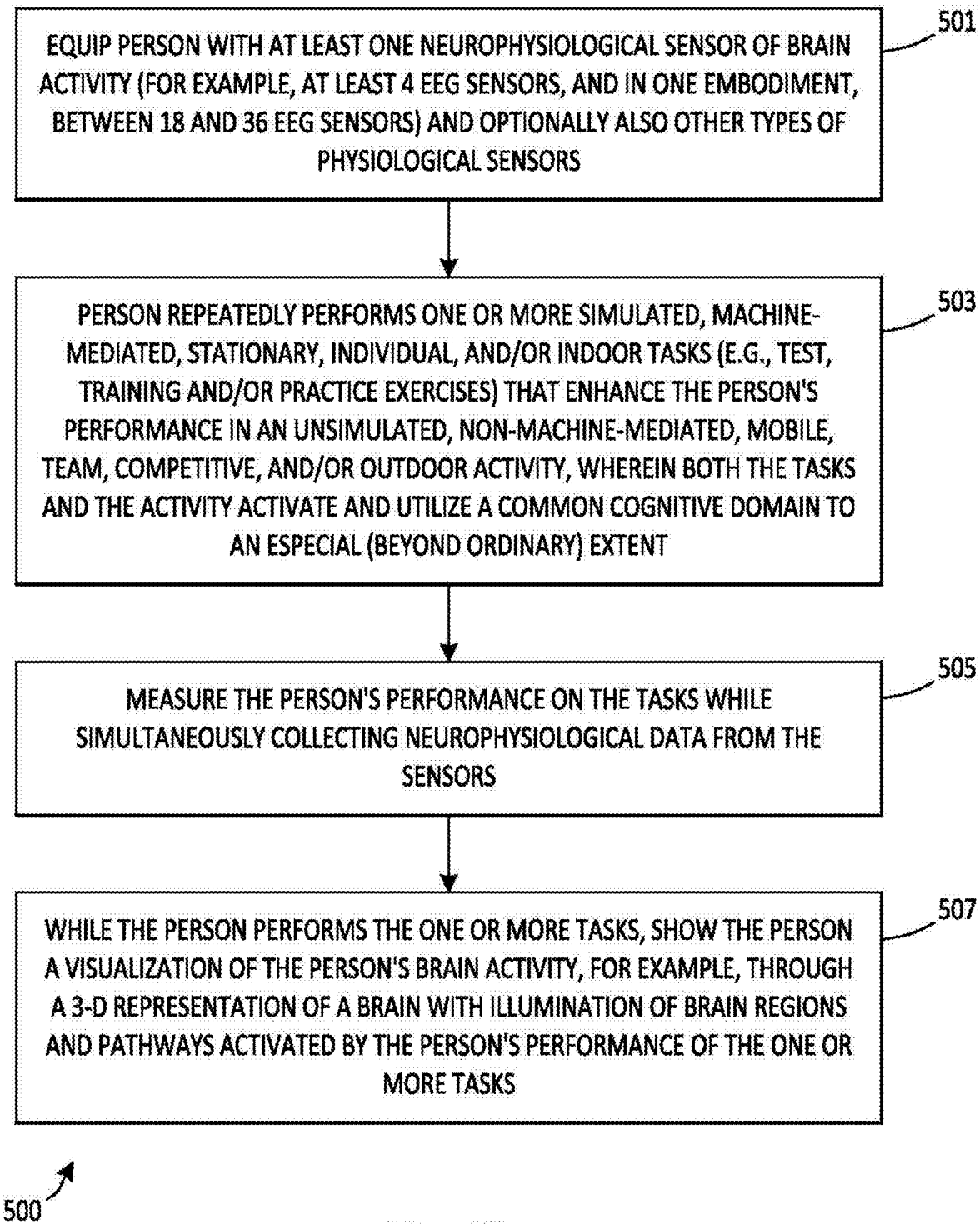
FIG. 12 illustrates one embodiment of a method of using brain imagery feedback to enhance performance.

FIG. 12 illustrates one embodiment of a method 500 of using brain imagery feedback to enhance performance in a real-world, un-simulated, and non-machine-guided activity such as a competitive sport, working at a job, or an outdoor activity. In block 501, equip a subject with at least one neurophysiological sensor of brain activity (for example, at least 4 EEG sensors, and in one embodiment, between 18 and 36 EEG sensors) and optionally also other types of physiological sensors. In block 503, select one or more simulated, machine-mediated, stationary, individual, and/or indoor tasks (e.g., test, training and/or practice exercises) that enhance the subject's performance in an un-simulated, non-machine-mediated, mobile, team, competitive, and/or outdoor activity. Moreover, select tasks that differentially recruit, activate, or utilize one or more common cognitive domains with the activity, as demonstrated by detectable changes in electrical or brain wave activity (e.g., higher-than-average frequency brain waves) of the associated system(s) of the brain, or as demonstrated by a comparison of systems of the brain significantly and markedly activated by a task with systems of the brain not significantly activated by the task. The tasks should be designed to produce a desired brain change—one that is closer to the brain state of an expert on the activity. Have the subject repeatedly perform the tasks over a period as short as a few minutes or as long as many years. In block 505, measure the subject's performance on the tasks while simultaneously collecting neurophysiological data from the sensors. In block 507, while the subject performs the one or more tasks, show the subject a visualization of the subject's brain activity, for example, through a 2D or 3D representation of a brain with illumination of brain regions and pathways activated by the subject's performance of the one or more tasks.

Figure 13:
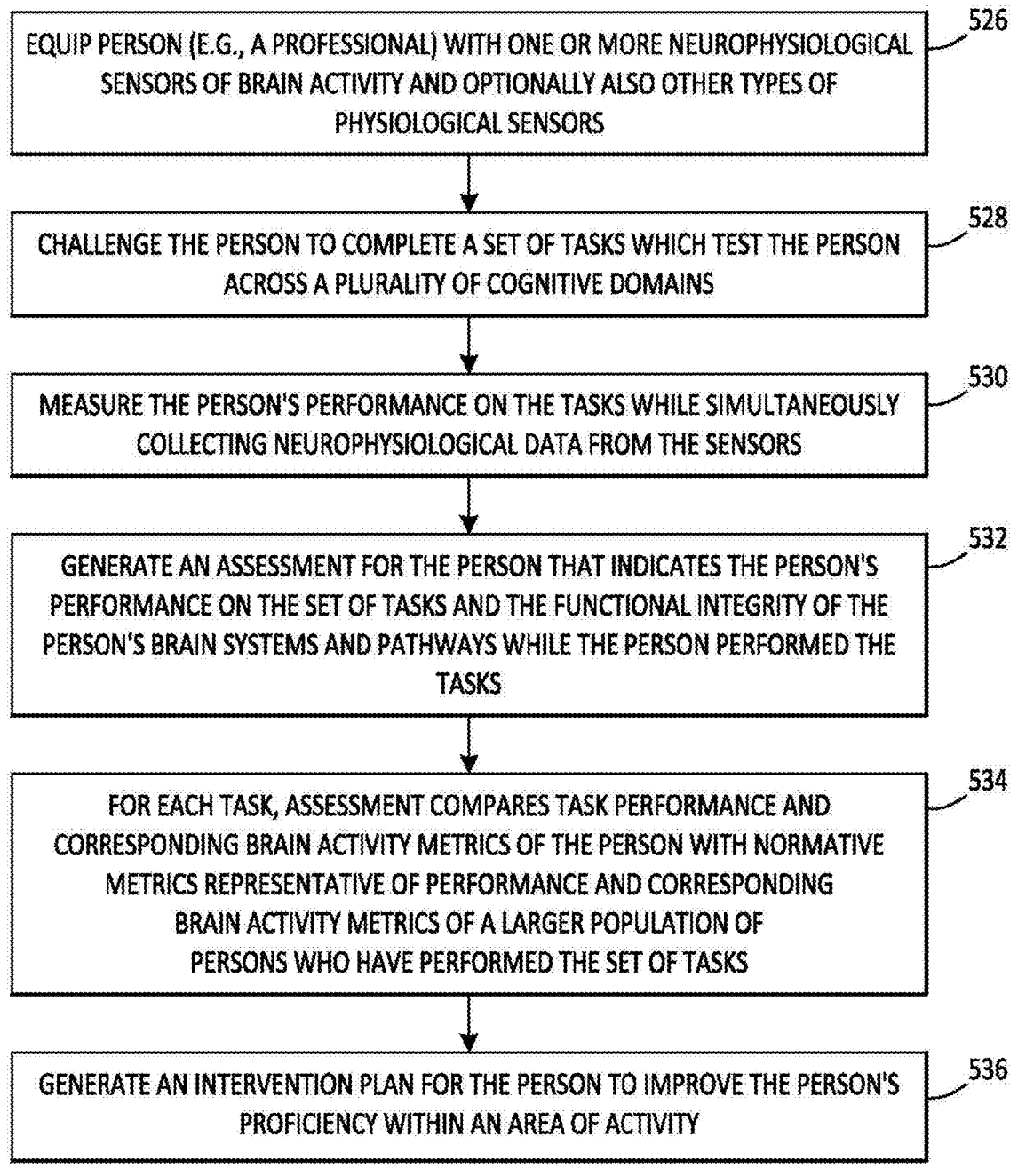
FIG. 13 illustrates one embodiment of a method of revealing functional systems of the brain.

FIG. 13 illustrates one embodiment of a method 525 of revealing functional systems of the brain. In block 526, equip a subject—for example, an athlete or professional—with one or more neurophysiological sensors of brain activity and optionally also other types of physiological sensors. In block 528, challenge the subject to complete a set of tasks which test the subject across a plurality of cognitive domains. In block 530, measure the subject's performance on the tasks while simultaneously collecting neurophysiological signal data from the sensors. In block 532, generate an assessment for the subject that indicates the subject's performance on the set of tasks and the functional integrity of the subject's brain systems and pathways while the subject performed the tasks. The assessment on the functional integrity is produced, in one implementation, by decomposing and bandpassing the signal data into multiple components across multiple frequency bands and then finding correlations between characteristics of the multiple components. The correlations are a useful approximation of the subject's functional connectivity. An example of this type of analysis is described in the discussion of the Portfolio Manager Case Study, discussed later in the specification.

In block 534, for each task, include in the assessment a comparison of task performance and corresponding brain activity metrics of the subject with normative metrics (e.g., a group performance metric and a corresponding group brain activity metric) that are representative of performance and corresponding brain activity metrics of a larger population of subjects—such as of athletes in the same sport or sport position or professionals in the same profession—who have performed the set of tasks.

In block 536, generate an intervention plan for the subject to improve the subject's proficiency within an area of activity. The plan includes exercises that preferentially activate selected systems and pathways of the subject's brain. The plan can also include the administration of a neurotropic or oral or intravenous supplement and/or coaching or training suggestions.

Figure 14:
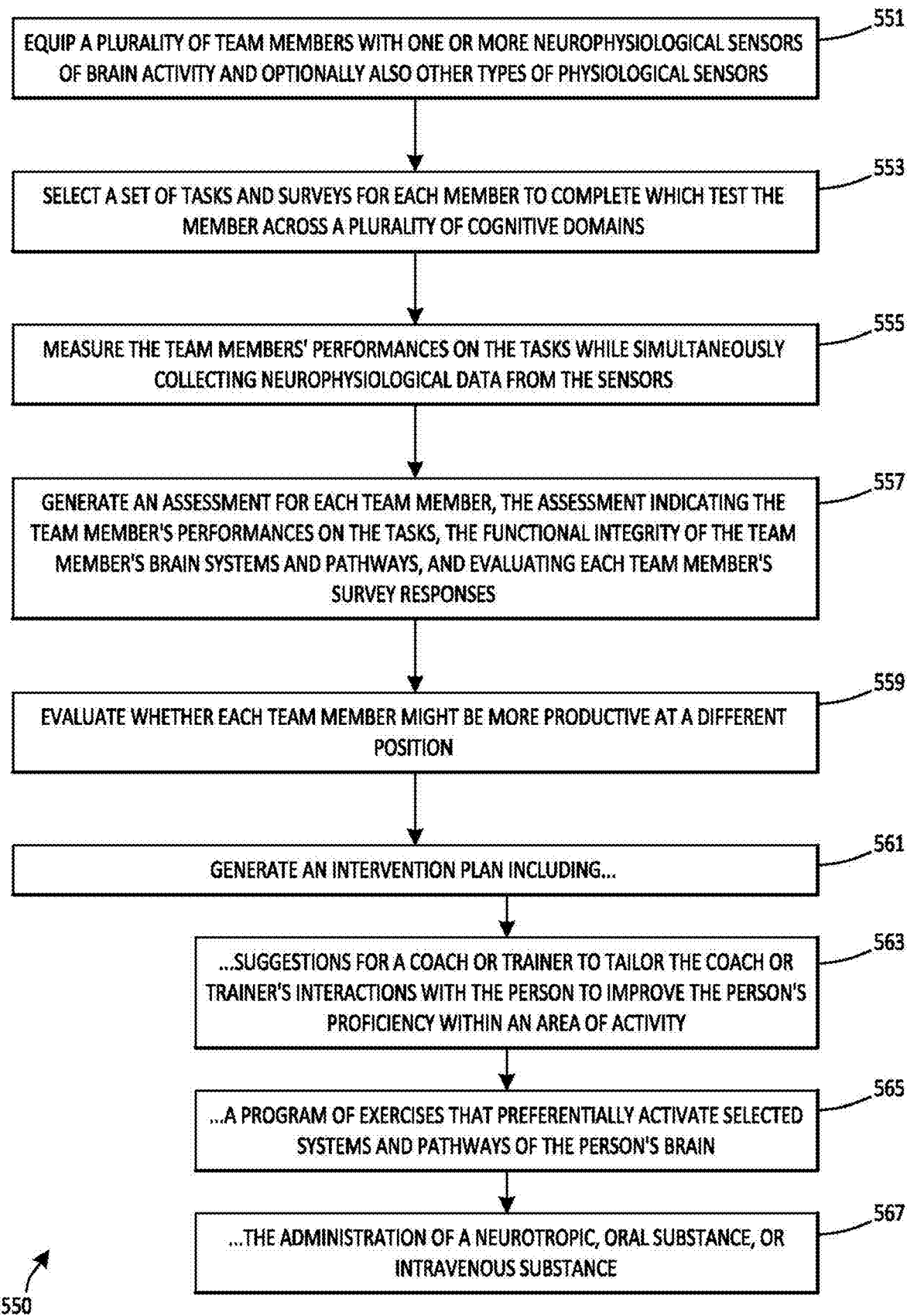
FIG. 14 illustrates one embodiment of a method of enhancing team preparation and coaching.

FIG. 14 illustrates one embodiment of a method 550 of enhancing team preparation and coaching. For example, goals in improving an athlete's/team-member's performance can include improved reaction time, increased motor speed, faster decision making, better performance under pressure, and shortened recovery time. Suitable metrics include brain activity and neural pathways, measuring baseline performance and improvements over time, comparing how players compare to each other, and comparing how the team compares to other elite teams. Desirable coaching insights would include a deeper understanding of each athlete's/team-member's brain strengths and weaknesses, greater insight into how each athlete/team-member learns, and information to help coaches/managers/trainers work with each athlete/team-member and for each athlete/team-member to stay in the zone.

In block 551, equip a plurality of team members with one or more neurophysiological sensors of brain activity and optionally also other types of physiological sensors. In block 553, select a set of tasks and surveys for each member to complete which test the team member across a plurality of cognitive domains. In block 555, measure the team members' performances on the tasks while simultaneously collecting neurophysiological data from the sensors. In block 557, generate an assessment for each team member, the assessment indicating the team member's performances on the tasks, the functional integrity of the team member's brain systems and pathways, and evaluating each team member's survey responses. In one implementation, the assessment also includes one or more of the following predictions: the player's/team-member's capacity to achieve a predefined level of proficiency through practicing and interventions; the amount of time and/or training and intervention needed to achieve the predefined level of proficiency; how well the team would play or operate if team positions/roles were reassigned amongst the players/team-members; and how well the team would play or operate if team positions/roles or more team players underwent targeted training. For example, the assessment may show that the team would perform 25% better if player/team-members A and B or B and C underwent training; but that targeted training on player/team-members A and C would provide less of a benefit.

In block 559, evaluate whether each team member might be more productive at a different position. This evaluation is based on predictive heuristics (see FIG. 17), which identifies an optimal assignment of players to team positions that provide the greatest odds of making the team successful. In one implementation, this evaluation is based on comparisons of statistical predictions of how proficient each team member would be in each of several positions, both with and without training and interventions.

In block 561, generate an intervention plan. As illustrated in block 563, the intervention plan can include suggestions for a coach, trainer or manager to tailor the coach's, trainer's, or manager's interactions with the subject to improve the subject's proficiency within an area of activity. As illustrated in block 565, the intervention plan can include a program of exercises that preferentially activate selected systems and pathways of the subject's brain. As illustrated in block 567, the intervention plan can include the administration of a neurotropic, oral substance, or intravenous substance.

Figure 15:
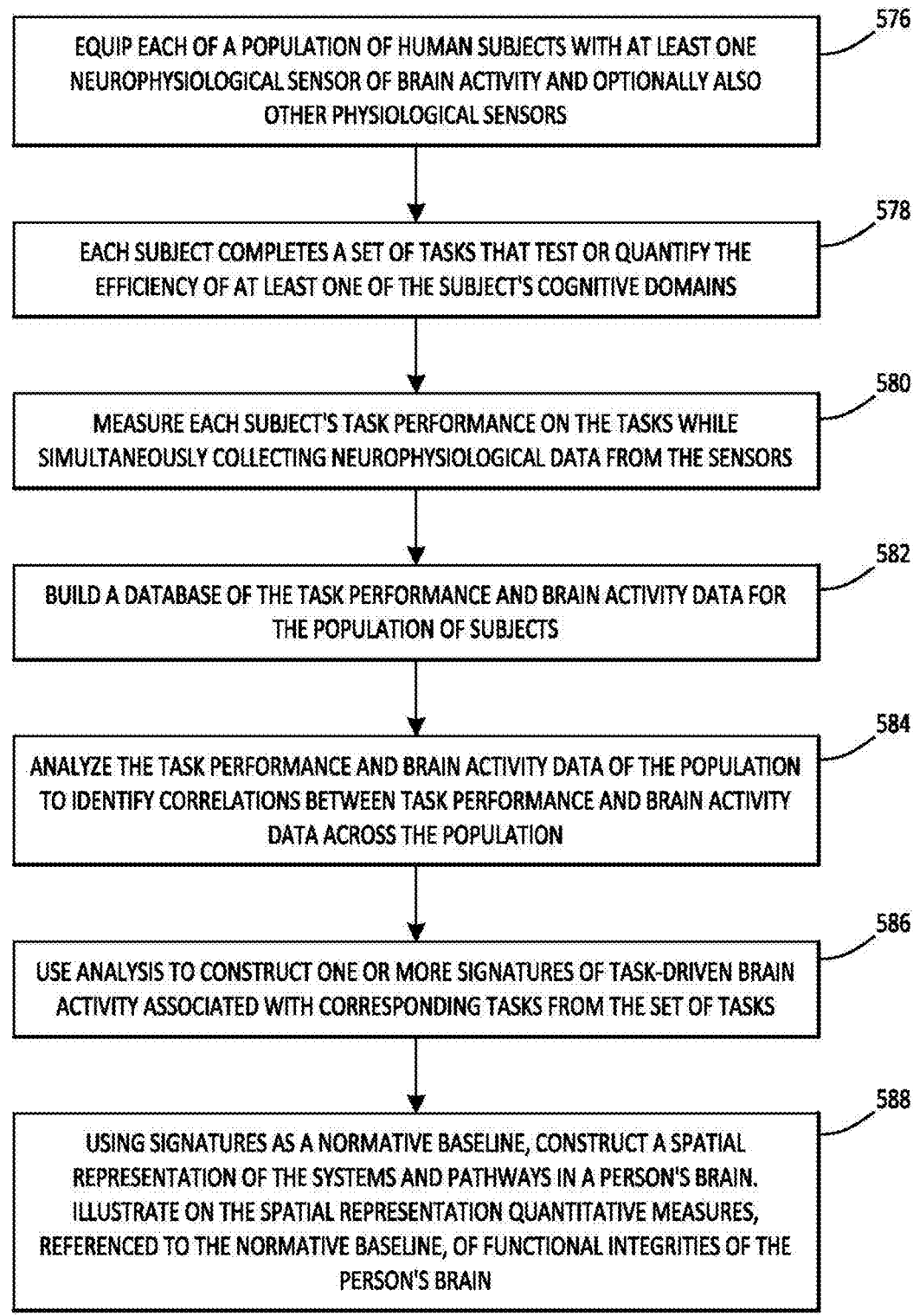
FIG. 15 illustrates one embodiment of a method of identifying signatures of task-driven brain activity.

FIG. 15 illustrates one embodiment of a method 575 of identifying signatures of task-driven brain activity. In block 576, equip each of a population of human subjects with at least one neurophysiological sensor of brain activity (e.g., at least 4 EEG sensors and in one embodiment, between 18 and 36 EEG sensors) and optionally also other types of physiological sensors. In block 578, each subject completes a set of tasks that test or quantify the efficiency of at least one of the subject's cognitive domains. In block 580, measure each subject's task performance on the tasks while simultaneously collecting neurophysiological data from the sensors. In block 582, build a database of the task performance and brain activity data for the population of subjects.

In block 584, analyze the task performance and brain activity data of the population to identify correlations between task performance and brain activity data across the population. In one embodiment, PCA and/or ICA is performed to identify such patterns. In block 586, use the analysis to construct one or more signatures of task-driven brain activity associated with corresponding tasks from the set of tasks. Each signature is a representation of characteristic levels of brain activity in one or more brain systems and/or pathways between the brain systems that are differentially activated by the task. Preferably, each signature quantifies levels of brain activity across a distribution of task performance levels, wherein the levels indicate a range of times, difficulty levels, and/or accuracy levels with which the task is performed.

In one implementation, signatures are built by inputting the database of task performance and brain activity data into a machine learning apparatus that identifies brain systems and/or pathways between the brain systems that are activated by each of the tasks and that further identifies degrees to which activity in said brain systems and/or pathways are correlated with task performance. Signatures are further refined by inputting data relating to several subjects' performances on tasks or in practical, real-world activities into the machine learning apparatus. The machine learning apparatus produces a matrix correlating a plurality of variables, including performance in tasks and performance in practical, real-world activities, with brain activity or quantitative representations of the brain systems' functional integrities. The machine learning apparatus also creates a prediction heuristic based on the correlation matrix which generates a prediction of a person's performance in a selected one of the practical, real-world activities as a function of the person's brain activity and performance of a task.

In block 588, using the signatures as a normative baseline, construct a spatial, spatio-temporal, and/or frequency-band-passed representation of the systems and pathways in a subject's brain. Illustrate on the representation quantitative measures, referenced to the normative baseline, of functional integrities of the subject's brain.

In one implementation of the process of FIG. 15, different numbers and arrangements of sensors are experimented with to find a minimal number of neurophysiological sensors, a minimally intrusive set of sensors, and/or a minimally expensive set of sensors necessary to detect and distinguish different levels of brain activity in different brain networks.

Figure 16:
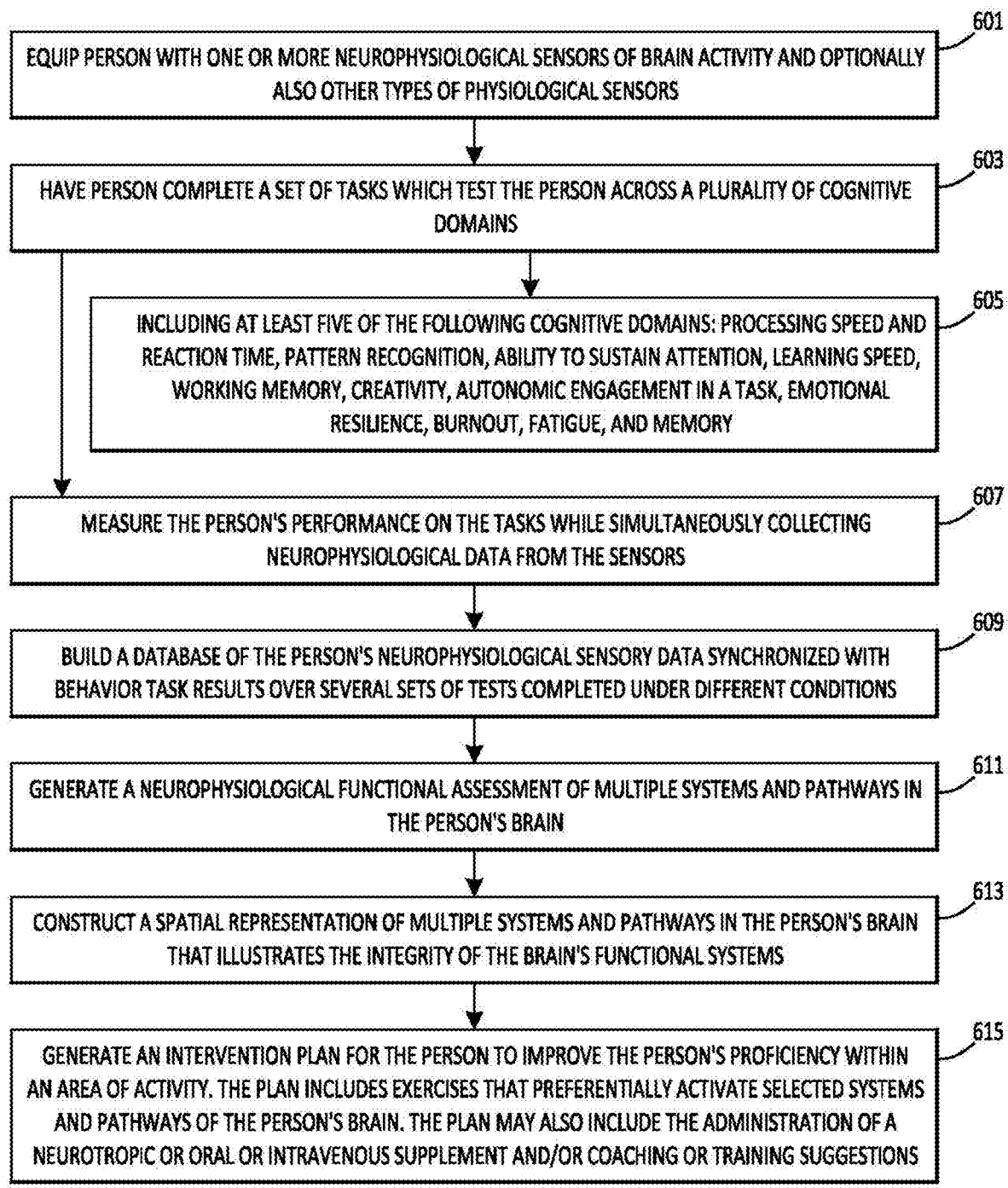
FIG. 16 illustrates one embodiment of a method of constructing an integrity map of the brain's functional systems.

FIG. 16 illustrates one embodiment of a method 600 of constructing an integrity map of the brain's functional systems. In block 601, equip a subject with one or more neurophysiological sensors of brain activity and optionally also other types of physiological sensors. In block 603, have the subject complete a set of tasks which test the subject across a plurality of cognitive domains. As illustrated in block 605, the plurality of cognitive domains can include at least five of the following: processing speed and reaction time, pattern recognition, ability to sustain attention, learning speed, working memory, creativity, autonomic engagement in a task, emotional resilience, burnout, fatigue, and memory. In block 607, measure the subject's performance on the tasks while simultaneously collecting neurophysiological data from the sensors. In block 609, build a database of the subject's neurophysiological sensory data synchronized with behavior task results over several sets of tests completed under different conditions. In block 611, generate a neurophysiological functional assessment of multiple systems and pathways in the subject's brain. In block 613, construct a spatial representation of multiple systems and pathways in the brain's brain that illustrates the integrity of the brain's functional systems. In block 615, generate an intervention plan for the subject to improve the subject's proficiency within an area of activity. The plan includes exercises that preferentially activate selected systems and pathways of the subject's brain. The plan can also include the administration of a neurotropic or oral or intravenous supplement and/or coaching or training suggestions.

Figure 17:
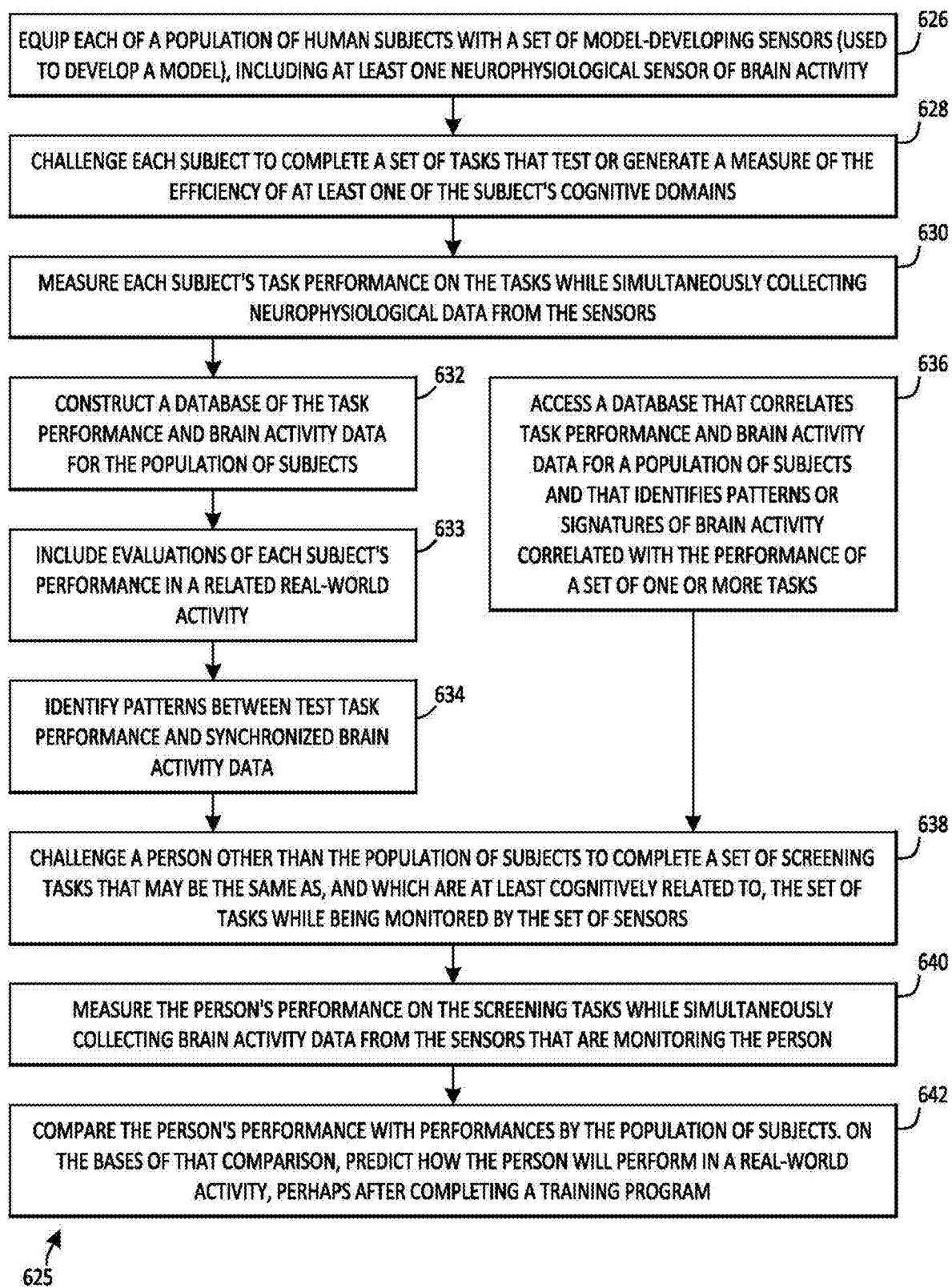
FIG. 17 illustrates one embodiment of a neurometric-based predictive model of performance.

FIG. 17 illustrates one embodiment of a neurometric-based performance predicting method 625. The method illustrates two paths, one starting with block 626 and including the construction of a database, and the other starting with block 636 and merely requiring access to such a database, to generating a prediction.

Starting with the first task, in block 626, equip each of a population of human subjects with a set of model-developing sensors (used to develop a brain model), including at least one neurophysiological sensor of brain activity. In block 628, challenge each subject to complete a set of tasks that test or generate a measure of the efficiency of at least one of the subject's cognitive domains. In block 630, measure each subject's task performance on the tasks while simultaneously collecting neurophysiological data from the sensors. In block 632, construct a database of the task performance and brain activity data for the population of subjects. In block 633, include evaluations of the subject's performances on real-world tasks are also included in the database.

In block 634, identify patterns between test task performance and synchronized brain activity data.

Flow proceeds to block 636. Block 636 is also the starting position for the second path, where a database 141 is already provided with the information generated in blocks 626-634. In block 636, access a database (e.g., the database of block 632) that correlates task performance and brain activity data for a population of subjects. The database includes data about performance and brain activity and brain activity signatures for a population of subjects that have performed a training program on a set of tasks, wherein the brain activity data includes chronologies of brain activity of one or more brain networks that are characterized by stronger connections when subjects repeatedly perform the set of tasks over a period of several days, weeks, or months.

In block 638, challenge or prompt or persuade an individual other than the population of subjects to complete a set of screening tasks that can be the same as, and which are at least cognitively related to, the set of tasks presented in block 628 while being monitored by the set of sensors. In block 640, measure the individual's performance on the screening tasks while simultaneously collecting brain activity data from the sensors that are monitoring the person.

In block 642, compare the individual's performance with performances by the population of subjects. On the basis of that comparison, predict how the individual will perform in a real-world activity, for example, playing in a professional sport or meeting or exceeding expectations as a financial professional, either with or without completing a training program. In one implementation, the prediction relates to how well the person will most likely perform the tasks that he/she trained upon after completing a training program. Also or alternatively, predict an amount of time that the individual will need to train to improve their performance to a predefined level of performance on the basis of the individual's performance on, and brain activity during performance on, the set of screening tasks, in relation to the data about performance and brain activity for the population of subjects.

In one embodiment, the method described above is extended to constructing a second predictive heuristic model. A sub-population of subjects undergoes a training program after completing the screening tasks a first time, and before completing the screening tasks a second time, while collecting brain activity data from the sub-population both the first and second times. A second predictive heuristic model is constructed that predicts the expected efficacy of a training regimen, based upon a comparison of the first-time and second-time performances on the screening task, along with corresponding brain activity data. Then, this second predictive heuristic model is used to predict how much the person's performance will improve upon completion of a training regimen.

In another embodiment, the method described in FIG. 17 is recharacterized as a method of predicting a person's fitness at performing one or more roles in a team effort. The person is prompted to complete a set of screening tasks while equipped with a set of brain activity sensors. Data is accessed that identifies brain networks that are most active in proficient performance of each of several different roles in the team effort. The person's performances on the set of screening tasks are measured and data simultaneously collected about activity in brain networks that are characterized by and known to have increased activity when performing the set of screening tasks. Then, a prediction is made about the person's fitness at performing the one or more roles in the team effort. The prediction is statistically- and algorithmically based rather than subjective. The prediction is generated as a function of the individual's performance, brain activity data, and data identifying brain networks most important in proficient performance of different roles in the team effort. The prediction can also be a function of the person's predicted emotional commitment to raise their fitness, wherein the emotional-commitment prediction is based on brain activity data of brain networks of the person that are associated with arousal and commitment.

In one implementation, the method also generates a prediction of how much training would be needed by the person to raise their fitness to perform the one or more roles in the team effort to a predefined level. The how-much-training prediction is also statistically based and a function of the individual's performance on, and brain activity during performance on, the set of screening tasks. This how-much-training prediction is furthermore a function of data about performance and brain activity for a previous population of subjects, demographics, surveys and/or other individual factors.

The method above can be extended to several members of a team. This involves performing the foregoing steps on a plurality of persons, including said person, that are contributing or available to contributing the team, and predicting a distribution of team roles among the plurality of persons that would make an optimally productive use of the plurality of person's relative talents as identified by their performance and brain activity data.

Alternatively, the method can be applied to candidates for positions on the team. This involves performing the foregoing steps on candidates for the one or more roles on the team, comparing the statistically-based predictions of the candidate's fitness as performing the one or more roles on the team effort, and selecting one of the candidates over another of the candidates to perform the one or more roles on the team on the basis of the comparison.

Figure 18:
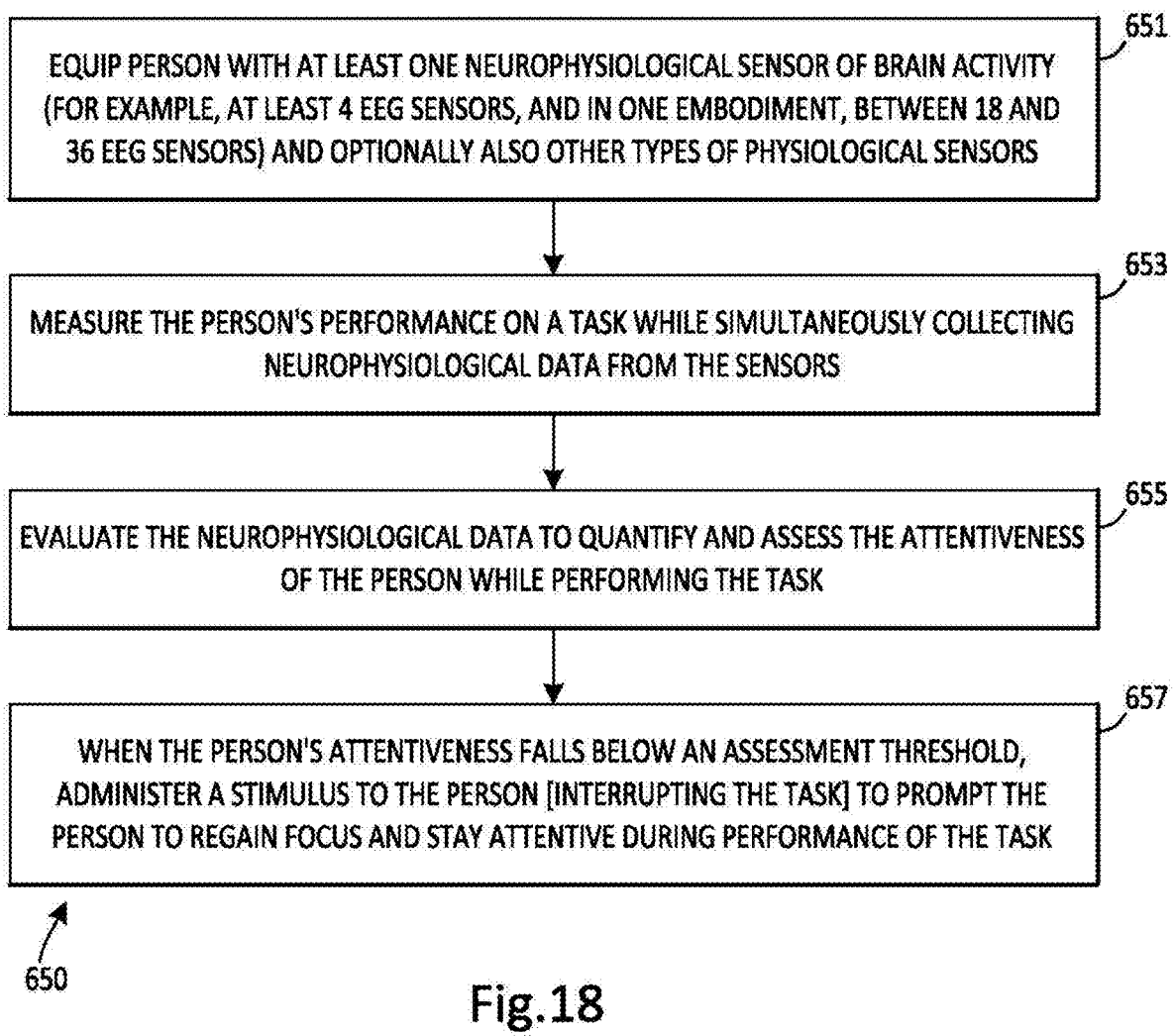
FIG. 18 illustrates one embodiment of a method of attention-monitoring system to improve cognitive efficiency.

FIG. 18 illustrates one embodiment of a method 650 of attention-monitoring to improve cognitive efficiency. In block 651, equip a person with at least one neurophysiological sensor of brain activity and optionally also other types of physiological sensors. In block 653, measure the person's performance on a task while simultaneously collecting neurophysiological data about the activity of the dorsal and/or ventral attention networks from the sensors. In block 655, evaluate the neurophysiological data to quantify and assess the attentiveness of the person while performing the task and to determine when the person's attention is waning.

If the person's attentiveness falls below an assessment threshold, in block 657 administer a stimulus to the person and/or interrupt the task to prompt, help, and/or remind the person to regain focus and stay attentive during performance of the task.

An attention-stimulating apparatus for performing the method of FIG. 18 comprises the following: one or more neurophysiological sensors 120 including one or more fittings to hold them, such as a helmet, headset, wristband, etc., to hold them; a processor (as embodied in the statistical engine 150); and a controller 165. The one or more neurophysiological sensors 120 are configured to monitor and generate data of brain activity of an attentional network of the person's brain (such as the dorsal or ventral attentional system or both) as well as of what is generally characterized as the default network of the person's brain. The processor is configured to analyze the brain activity data of the default network to assess whether the person is performing a cognitive task. The processor is further configured to analyze the brain activity data of the attentional network to assess whether the person is paying sufficient attention to performing the task. Sufficiency of attention is a function of a degree of brain activity in the attentional network. The controller 165 a controller is a chip, an expansion card, or a stand-alone device that interfaces with a peripheral device. The controller 165 operates a sensory output device that provides a sensory output such as haptic feedback, light, and/or sound.

The processor causes the controller 165 to activate the sensory output device when the analysis indicates that the person is not paying sufficient attention to performing the task. More particularly, the processor quantifies the attentiveness of the person while performing the task on the basis of the brain activity of the person's attentional network; and when the person's attentiveness falls below a threshold, triggers the sensory stimulus output to the person.

As an alternative to the sensory output device, the controller 165 can operate a different type of stimulus device (e.g., electrical stimulator to the brain, a device for delivering a neurotropic substance to the person that affects the brain, an IV, etc.). Electrical stimulation would be provided at a frequency associated with maximum or near-maximum attention.

Figure 19:
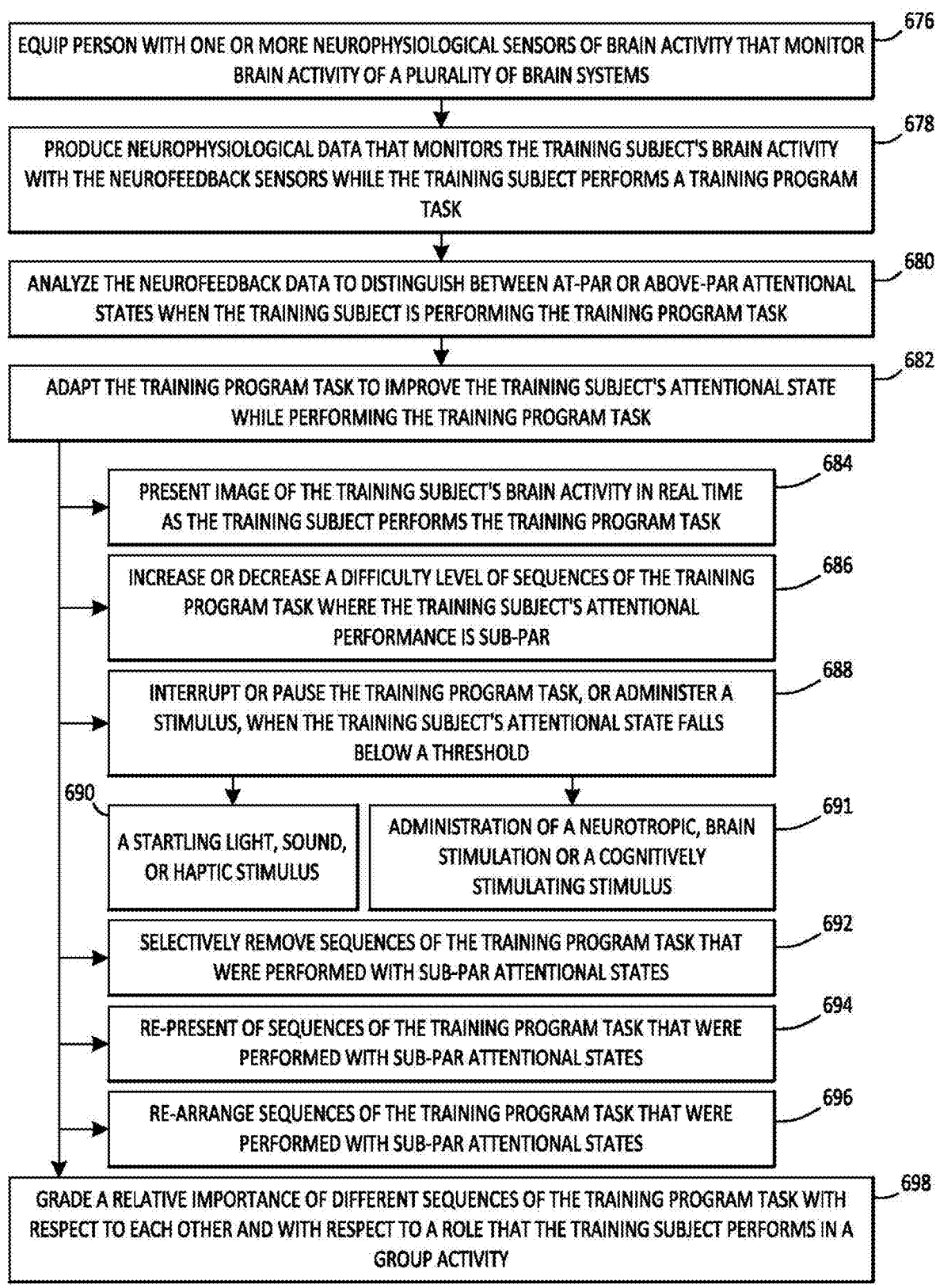
FIG. 19 illustrates one embodiment of a method of closed-loop adaptive training system using neurofeedback.

FIG. 19 illustrates one embodiment of a method 675 of closed-loop adaptive training using neurofeedback. In block 676, equip a training subject with one or more neurophysiological sensors of brain activity that monitor and produce data of brain activity of a plurality of brain systems/networks. In block 678, produce neurophysiological data that monitors the training subject's brain activity with the neurofeedback sensors while the training subject performs a training task. In block 680, quantify and rank attentional states of a previous population of people while performing the task. Define a targeted attentional state on the basis of the quantified and ranked data about the attentional states of the previous population of people. Also, analyze the training subject's neurofeedback data to determine whether the training subject is performing at the targeted attentional state and to distinguish between at-par or above-par attentional states when the training subject is performing the training task. In one embodiment, data transforms such as but not limited to PCA and/or ICA is performed to identify such patterns.

Different implementations or embodiments of FIG. 19 involve changes or additions to one or more of the above actions. In one implementation, the targeted attentional state is defined as a function of previously measured peak attentional states of the training subject. In another implementation, the neurophysiological data is analyzed to detect negative changes in the training subject's attentional state when the training subject is performing the training task. In yet another implementation, the training task is adapted to interrupt or pause the training task while the training subject performs the training task, in response to significant negative changes and/or drops below a threshold in attention. And in a further implementation, the neurophysiological data is also evaluated to determine the training subject's brain workload.

Blocks 682-696 present non-exhaustive implementations of feedback that transform the training regimen into a closed loop system. Block 682 broadly represents any adaptation and/or enhancement of the training task to improve/enhance the training subject's attentional state while performing the training task. Blocks 684-696 are more specific.

In block 684, present images or video of the training subject's brain activity in real time as the training subject performs the training task. In block 686, increase or decrease a difficulty level of sequences of the training task where the training subject's attentional performance is sub-par.

In block 688, interrupt or pause the training task, or administer a stimulus, when the training subject's attentional or neurocognitive state falls below a threshold and/or if the training subject's brain workload goes above a different threshold. As illustrated in block 690, the interruption or stimulus can be provided in the form of a startling light, sound, or haptic stimulus to refocus or encourage the training subject. As illustrated in block 691, the interruption or stimulus can be provided in the form of administration of a neurotropic, electrical or magnetic brain stimulation, or a cognitively stimulating stimulus. In block 692, selectively remove sequences of the training program task that were performed with sub-par attentional states. In block 694, re-present sequences of the training program task that were performed with sub-par attentional states. In block 696, Re-arrange sequences of the training program task that were performed with sub-par attentional states. In block 698, indicate the trainee's performance relative to a baseline. The baseline can be the trainee or another individual, an "elite" model, a team, a role in a group activity, the general public, or relevant demographic baselines.

The method of FIG. 19 is useful to the monotonous "task" or "activity" of studying game film of athletes playing a sport on a court or playing field, which taxes attentiveness and for which a training program of the present invention would be useful. As applied to the game-film-studying task, the function of adapting the game-film-studying task is, in one implementation, the selective removal of future film sequences that resemble sequences of the film where watching was performed with sub-par attentional states. This adaptation could dramatically reduce the amount of time a player needs to film watch. The function of adapting the game-film-studying task is, in another implementation, re-presentation of sequences of the film that were watched with sub-par attentional states. In yet another implementation, the adaptation of the game-film-studying is re-arrangement of sequences of the film that were watched with sub-par attentional states. Another implementation selectively removes sequences in which (a) the training subject's attentional state was below-par, and (b) the selectively removed sequences have a relatively low-importance grade.

In a more sophisticated implementation, adaptation of the game-film-studying task involves grading a relative importance of different sequences of the film with respect to each other and presenting only important sequences of the film. Grading is done at least in part by identifying particular sequences of the game-film-studying task that differentially activate particular brain systems or that cause neurometric markers of attentiveness to decline (such as boring sequences). This grading, in combination with logic programmed to identify similar sequences in other films of the same sort, enables these sequences to be culled out or re-emphasized, as needed.

In block 692, selectively remove sequences of the training task that were performed with sub-par attentional states. In alternative block 694, have the training subject repeat sequences of the training task that were performed with sub-par attentional states. In alternative block 696, re-arrange sequences of the training task that were performed with sub-par attentional states. In alternative block 698, grade a relative importance of different sequences of the training task with respect to each other and with respect to a role that the training subject performs in a group activity.

Figure 20:
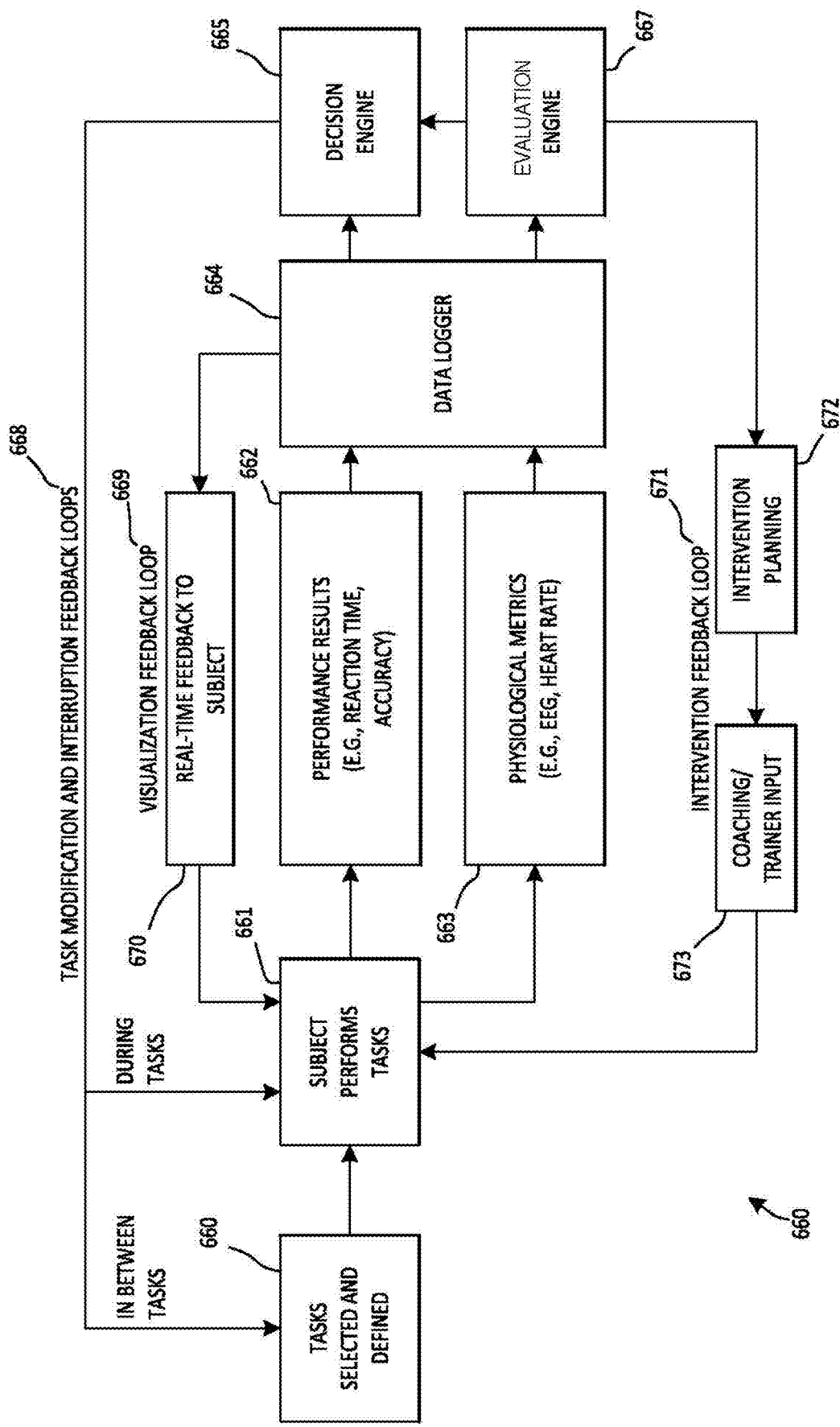
FIG. 20 is a block diagram illustrating several closed feedback loops in one embodiment of a neurometric-enhanced performance assessment system.

FIG. 20 is a block diagram illustrating several closed feedback loops in one embodiment of a neurometric-enhanced performance assessment system 660. In block 660, tasks are selected, and task parameters are defined. In block 661, a subject performs the tasks. While the subject performs the tasks, performance related-data—which include both the subject's performance (e.g., reaction time, accuracy) and comparative data (e.g., market data, industry standards)—and physiological metrics 663 (e.g., EEG, heart rate)—which can also include comparative data—are collected by a data logger 664. A decision engine 665 analyzes the collected data and decides whether and how to modify the tasks or interrupt the tasks (e.g., because of a detected distraction or lack of attentiveness). FIG. 20 depicts two task modification and interruption feedback loops 668. One feedback loop 668 involves modifying and redefining the tasks in between tasks, on the basis of the performance results 662 and physiological metrics 663. Another feedback loop 668 involves modifying or interrupting the tasks in real-time, as they are performed, as discussed in the description of FIG. 19.

The provision of real-time feedback 670 to the subject (e.g., brain imagery, charts, graphs, maps) produces a visualization feedback loop 669 when the subject, seeking to improve his/her performance, adjusts his/her focus and attention in response to the visualization. Also, the generation of an intervention plan 672 followed up by coaching or trainer input 673 forms an intervention feedback loop 671.

Figure 21:
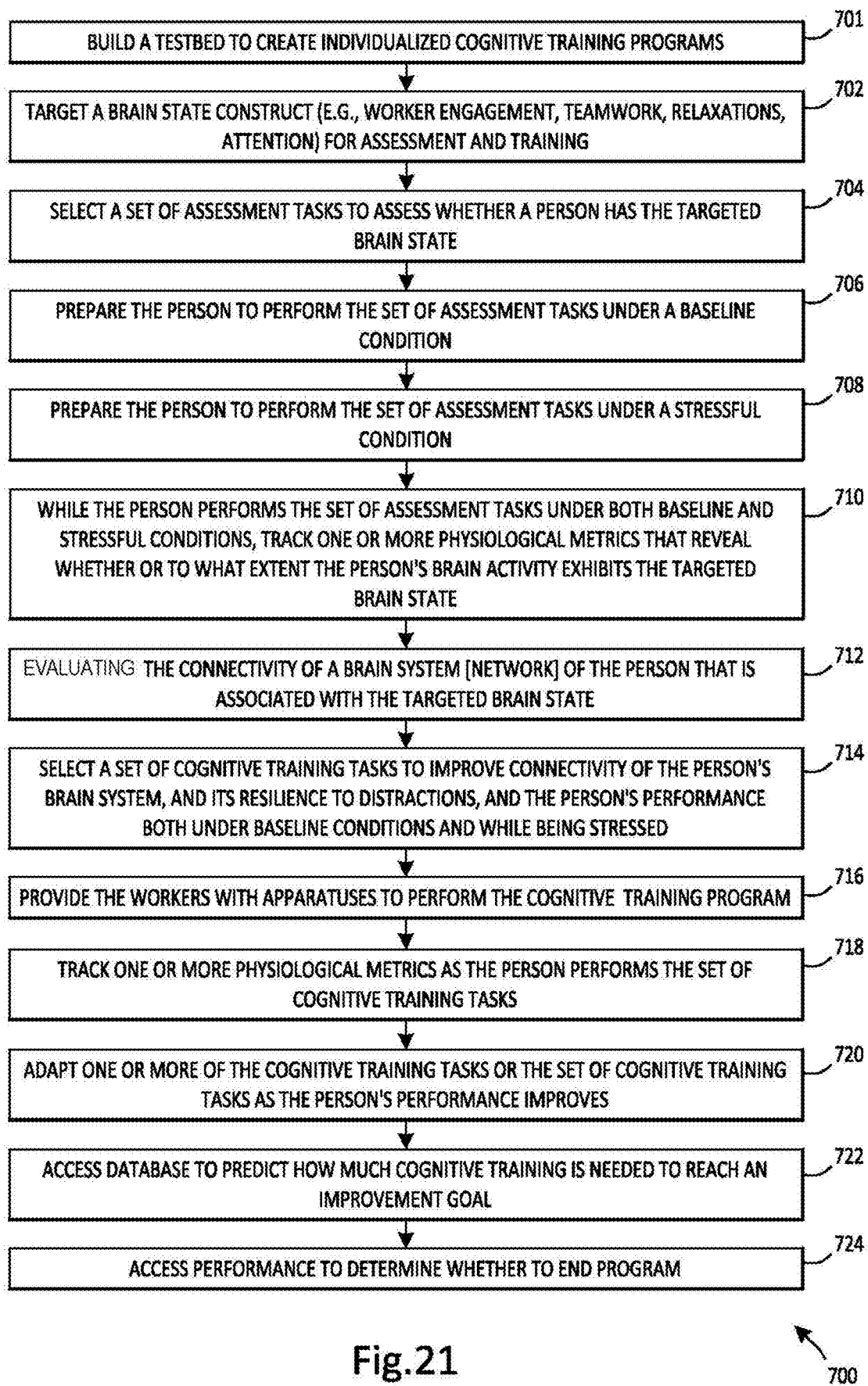
FIG. 21 is a chart illustrating a method of constructing an individualized cognitive training program for a person.

FIG. 21 illustrates a method 700 of constructing an individualized cognitive training program for a person. The components of FIG. 1 are described as "blocks" rather than "steps" because they need not be carried out in the exact order presented.

In block 701, assemble equipment into a testbed to use to create individualized cognitive training programs. In one implementation, the equipment set forth in Table 2 is contemplated.

TABLE 2

Exemplary set of testbed components

| Equipment | Provider | Description |
|---|---|---|
| Quick 20 EEG Headset | Cognionics (San Diego, CA) | Mobile EEG hardware that includes 20 EEG sensors |
| M4 EEG Headset | Platypus Institute (New York, NY) | Focus signal |
| E4 Wristband | Empatica (Cambridge, MA) | PPG (measures blood volume pulse), GSR sensor (skin electrical properties), 3-axis accelerometer, infrared thermopile (skin temperature) |
| Zephyr BioModule | Vandrico Solutions Inc. (North Vancouver, BC) | HR, HRV, Respiration Rate, Appx core temp. |
| NeuroTracker | CogniSens Inc. (Montreal, QB) | 3D visual perceptual training |
| Tobii | Tobii Inc. (Sweden) | Eye Tracking, Pupillometry |
| Unity | Unity3d (San Francisco, CA) | Game development platform |
| DANA Brain Modular | Platypus Institute | Software |
| Gaming Laptop | ASUS (Taipei, TW) | IT hardware |
| HTC Vive-Pro | HTC (New Taipei City, TW) | VR headset |
| Stylistic M532 | Fujitsu (Tokyo, JP) | Tablet |
| Video Camera/Tripod | Sony (Tokyo, JP) | — |

In block 702, one or more "brain state" constructs are targeted. A brain state construct (simply "brain state" for brevity) can be negative (e.g., irritable) or positive (e.g., creative, engaged). It includes both brain states that are widely accepted within the scientific community (e.g., attention, memory retrieval) and informally characterized (e.g., working well with the team). Previously presented Table 1 lists several exemplary brain state constructs ("brain states," for simplicity) along with psychophysiological metrics that can be obtained to characterize and detect those brain states.

In block 704, select or create a set of assessment tasks to assess whether a person has the one or more targeted brain states. In one implementation, one assessment task is a biological motion perception test that assesses the person's visual systems' capacity to recognize complex patterns and human movements that are presented as a pattern of a few moving dots. Another assessment task is a 3D multiple-object-tracking speed threshold task that distributes the person's attention among a number of moving targets among distractors presented on a large visual field, and that involves speed thresholds and binocular 3D cues (i.e., stereoscopic vision). In general, assessment tasks are selected or created that match the targeted brain state construct.

The assessment can also include survey questions, such as about the person's caffeine intake or hours slept.

In block 706, prepare the person to perform the set of assessment tasks under a baseline condition. A baseline condition is one that involves a relatively low workload and demands a relatively lower amount of engagement, compared to a training condition.

In block 708, prepare the person to perform the set of assessment tasks under a stressful condition, preferably at a different time of day. "Preparation" can be, for example, providing the person with a set of test implements (e.g., computing device and software) and/or challenging the person to take the assessment (e.g., reminders, coaching, counseling) at a given time.

In one implementation, a first assessment is taken in the morning, when the person is in a baseline (e.g., relaxed) condition. After the person has encountered several hours of various challenges (whether pre-planned, anticipated, or spontaneous), a second assessment is taken when the person is under stressful conditions.

Stressful conditions can be divided into the following categories: environmental stressors, increased task difficulty, and internal stressors. An environmental stressor could be background noise, uncomfortable working conditions, and other distractions imposed upon the person. Increased task difficulty could refer to any controllable parameter (e.g., required attention, speed, precision, and agility) that makes performance of a task more difficult. An internal stressor could be feeling group pressure, knowing that you are not performing to expectations, knowing that others are performing much better than you, or knowing that money is at stake. Other internal stressors include stress, fatigue or distraction that the person still feels over the challenges encountered earlier in the day.

In block 710, while the person performs the set of assessment tasks under both baseline and stressful conditions, track one or more physiological metrics that reveal whether or to what extent the person's brain activity exhibits the one or more targeted brain states. Table 2 above lists several examples of physiological sensors and equipment that can be used to track the one or more physiological metrics. For example, theta brain waves (4-7 Hz) are indicative of attention. Also, observations of eye position, dwell time and fatigue can contribute to detection of engagement, arousal and attentional state of the person.

One example of an assessment or training task is reading a text while a person's eye movements are tracked. By detecting the position of the person's pupil, one implementation of the NEPAS 100 determines, approximately, what portion of the text the person is reading or dwelling upon at any given moment. The NEPAS 100 also tags the text with shading or shapes that show approximate areas that were skimmed over too quickly or that the person dwelt upon. The sizes of the shaded areas or shaped can be used to indicate the amount of time taken to read them. Scores are assigned to the shaded areas or shapes that indicate the level of interest, engagement, and comprehension. NEPAS 100 then directs the person to review at least a portion of the shaded areas or shapes again.

In block 712, use the physiological data generated by the tracking to infer the connectivity of a brain system (i.e., a brain network) of the person that is associated with the targeted brain state. In block 714, select a set of cognitive training tasks to improve connectivity of the person's brain system, and its resilience to distractions, and the person's performance both under baseline conditions and while being stressed, wherein the cognitive training program comprises the set of cognitive training tasks. In one implementation, the cognitive training tasks are the same as the assessment tasks. In another implementation, the cognitive training tasks are more varied than the assessment tasks and include normal daily tasks or work tasks. The cognitive training tasks are designed with ample positive reinforcement to portray the challenges as opportunities rather than burdens, and to increase the person's motivation and emotional engagement with the training. In block 716, provide the person with an apparatus (such as software, EEG equipment, and/or an exercise or test facility) to perform the cognitive training program.

Blocks 718 and 720 illustrate further optional actions associated with operating the cognitive training program. In block 718, one or more physiological metrics are tracked as the person performs the set of cognitive training tasks. This is in addition to the physiological metrics tracked during assessments, as illustrated in block 710. It is not necessary that the same metrics used in the assessment also be used during performance of the cognitive training tasks. For example, an EEG utilizing a large number of sensors can be applied during the assessments, while a simpler EEG headset encompassing only a few sensors (i.e., as few as three) is worn by the person throughout the day between morning and evening assessments. In optional block 720, optionally adapt one or more of the cognitive training tasks or modify the set of cognitive training tasks as the person's performance improves. Examples of task adaptations are set forth in FIG. 19, blocks 682-696. Further adaptations can be in the form of stressors imposed upon the person while performing the tasks. Such task adaptations would be in addition to adaptions the person makes on his/her own to improve performance.

In block 722, access the database 141 (FIG. 1) to predict how much cognitive training is needed to reach a cognitive improvement goal. The prediction is based in part upon a correlation performed on data correlating a populations' brain activity metrics with that population's performance on baseline and training task assessments. The prediction is also based in part upon the person's own neurometric data and task performance. For example, detection of theta brain waves can be used to predict (i.e., assign a probability to) whether something encountered today will be remembered tomorrow. Such predictions can aid persons in becoming better managers of their time.

The actions illustrated in blocks 710 and 718 are optionally further enhanced by providing real-time feedback to the person regarding the person's brain activity while the person performs the cognitive training tasks. This real-time feedback could be, for example, in the form of a graphical representation of a brain and connections within a relevant brain network of the person, highlighting or otherwise providing an indication of the strength of those connections. The actions illustrated in blocks 710 and 718 can also be optionally enhanced by providing visual feedback to the person regarding a relationship between the person's brain activity and the person's performance on the cognitive training tasks. This visual feedback could be, for example, in the form of a graph or a motion video showing a metric quantifying the strength of the network's connections and the corresponding performance of the person versus or over time.

In block 724, the cognitive training program is ended, according to one implementation, when (1) the person's performance or rate of performance improvement under baseline conditions exceeds a first threshold; or (2) the person's performance or rate of performance improvement under stress exceeds a second threshold. Another implementation is the same, except that the "or" is replaced with an "and." A third implementation ends the cognitive training program when the physiological data indicates that the connectivity within the system of the person's brain exceeds a targeted threshold or percentile. Many other implementations are contemplated.

The method 700 of FIG. 21 can be readily applied to improve workplace productivity. In one embodiment, one or more of the following brain states are targeted: attentiveness, memory, worker engagement, creativity, and teamwork. Under both baseline and stressful conditions, workplace workers perform a set of assessment tasks that assess the quality of brain networks involved in attention, memory, worker engagement, creativity, and/or teamwork. Physiological sensors such as EEG sensors track the workers while they perform the tasks in order to reveal whether or to what extent each worker's brain activity exhibits the targeted brain state. An individualized cognitive training program is prepared for each worker, comprising a set of training tasks selected to improve connectivity of the worker's relevant brain networks and their resilience to distractions, under both baseline and stressful conditions.

Employee Case Study

One embodiment of the invention was applied to an employee case study. A description of the case study is found in the recently published paper, Miller, S. L., Chelian, S. E., McBurnett, W., Tsou, W., Kruse, A. A. "An investigation of computer-based brain training on the cognitive and EEG performance of employees," *In Proceedings of the 41st IEEE International Engineering in Medicine and Biology Conference* (2019), which is herein incorporated by reference. A description is also provided below.

Twenty-one employees of a multinational information technology and equipment services company underwent a neurocognitive training program that consisted of an initial assessment, a six week "boost" or intervention period, and then a re-assessment to track the progress of each individual participant. The employees were split into two training groups: six females and four males in a long-training group that averaged 30 hours of total training during the boost period; and five females and six males in a short-training group that averaged 7 hours of training. A pre-training assessment of neurocognitive performance revealed no statistically significant group differences in performance. After the training, the participants were re-assessed.

The post-training assessment revealed that training participants experienced three measurable positive impacts from the program: higher standardized behavioral metrics, reductions in brain workload required to perform the tasks, and positive self-reported data. Cognitive efficiency increased by 12% in the high-training group and 5% in the low-training group. Study participants also reported improvements in their productivity and mental performance post-study.

The brain-training program targeted four areas: brain speed, attention, people skills and intelligence. It lasted for 6 weeks and was made available on-line via computer, cellphone, etc. Participants worked on specified programs at least 3 times per week. Over the course of the training, participants in the long-training and short-training groups completed, on average, 824 and 201 levels of training, respectively.

The following assessments, both pre- and post-training, were performed with behavioral and electrophysiological data recording: Baseline Task of Eyes Open/Eyes Closed, the Eriksen flanker task, the DANA standard neurocognitive assessment (Table 1), and surveys on sleep, stress and emotional resilience:

EEG data was collected with Cognionics™ Q20 headsets that included 20 dry electrodes with a sampling rate of 500 Hz. EEG was recorded during all assessments except the surveys. Assessments took about 90 minutes.

Analysis of the pre- and post-test electrophysiological and behavioral test scores were performed using multivariate analysis of variances procedures. FIG. 27 illustrates some of the steps by which the EEG data was pre-processed and spectrally analyzed in order to produce measures of brain workload.

In preprocessing step 871, the data was filtered with low pass filtering to remove automated artifacts, such as eye and muscle motion. In step 872, the data was filtered with high pass filtering to remove bad channels and interpolate. In step 873, common average referencing was applied to the data to remove bad time windows.

In spectral analysis step 874, a power spectral density estimation was performed on the data to compute the employees' brain bandpower during tasks. In spectral analysis step 875, a relative spectral density estimation was obtained by computing bandpower ratios between active states and at-rest states.

Robust mean and robust standard error of the mean (SEM) values for the amount of time it took each training group to perform a task, both pre-training and post-training, were also calculated.

It was found that the ratio between beta and the sum of theta and alpha correlated with higher workloads. Also, the ratio between higher theta and beta correlated with better memory, whereas the ratio between lower theta and beta correlated with more attention.

Table 2 sets forth start (Time=1) and end (Time=2) cognitive efficiency data for the long-training and short-training groups, showing mean time to complete the tasks and standard errors (S.E.M.). Cognitive efficiency scores were generated as a function of both speed and accuracy. After brain training, significant ($p<0.05$) effects of time (Time 1 vs Time 2) were observed for all tasks, except for a memory search task (MS) and the final task, Simple Reaction Time 2 (SRT2). The long-training group showed significantly ($p<0.5$) larger training effects for the Procedural Reaction Time (PRT) and Go/NoGo Task (GNG).

TABLE 2

Pre- and Post-Training Performance by Group and Task
Cognitive Efficiency Results (pre-training = 1; post-training = 2)

| Task | Group | Time | Mean | S.E.M. |
|---|---|---|---|---|
| SRT1 | Long Training Group | 1 | 154.823 | 7.398 |
|  |  | 2 | 171.665 | 5.951 |
|  | Short Training Group | 1 | 152.527 | 6.940 |
|  |  | 2 | 164.847 | 5.582 |
| CSL | Long Training Group | 1 | 42.548 | 3.237 |
|  |  | 2 | 51.277 | 3.234 |
|  | Short Training Group | 1 | 44.245 | 3.036 |
|  |  | 2 | 49.963 | 3.034 |
| PRT | Long Training Group | 1 | 102.120 | 4.225 |
|  |  | 2 | 114.085 | 3.855 |
|  | Short Training Group | 1 | 104.855 | 3.964 |
|  |  | 2 | 108.720 | 3.616 |
| SP | Long Training Group | 1 | 32.883 | 2.835 |
|  |  | 2 | 39.220 | 3.010 |
|  | Short Training Group | 1 | 32.683 | 2.660 |
|  |  | 2 | 36.239 | 2.824 |
| GNG | Long Training Group | 1 | 128.512 | 6.907 |
|  |  | 2 | 140.725 | 4.239 |
|  | Short Training Group | 1 | 127.235 | 6.480 |
|  |  | 2 | 127.254 | 3.976 |
| M2S | Long Training Group | 1 | 39.623 | 3.969 |
|  |  | 2 | 38.648 | 3.423 |
|  | Short Training Group | 1 | 39.684 | 3.723 |
|  |  | 2 | 39.448 | 3.211 |
| MS | Long Training Group | 1 | 54.973 | 4.286 |
|  |  | 2 | 76.083 | 5.346 |
|  | Short Training Group | 1 | 54.838 | 4.021 |
|  |  | 2 | 65.805 | 5.015 |
| SRT2 | Long Training Group | 1 | 160.709 | 6.065 |
|  |  | 2 | 169.560 | 6.491 |
|  | Short Training Group | 1 | 159.848 | 5.690 |
|  |  | 2 | 160.329 | 6.089 |

The sum of the cognitive efficiency scores for the long- and short-training groups was 716.2 and 715.9, respectively. After brain training, those scores improved 12% and 5%, respectively, to 801.3 and 752.6, respectively. Differences were more profound for the long-training group on the Procedural Reaction Time Task and the Go/No-Go. Both tasks require more cognitive control (rapid response selection) than a simple reaction time task.

Figure 28:
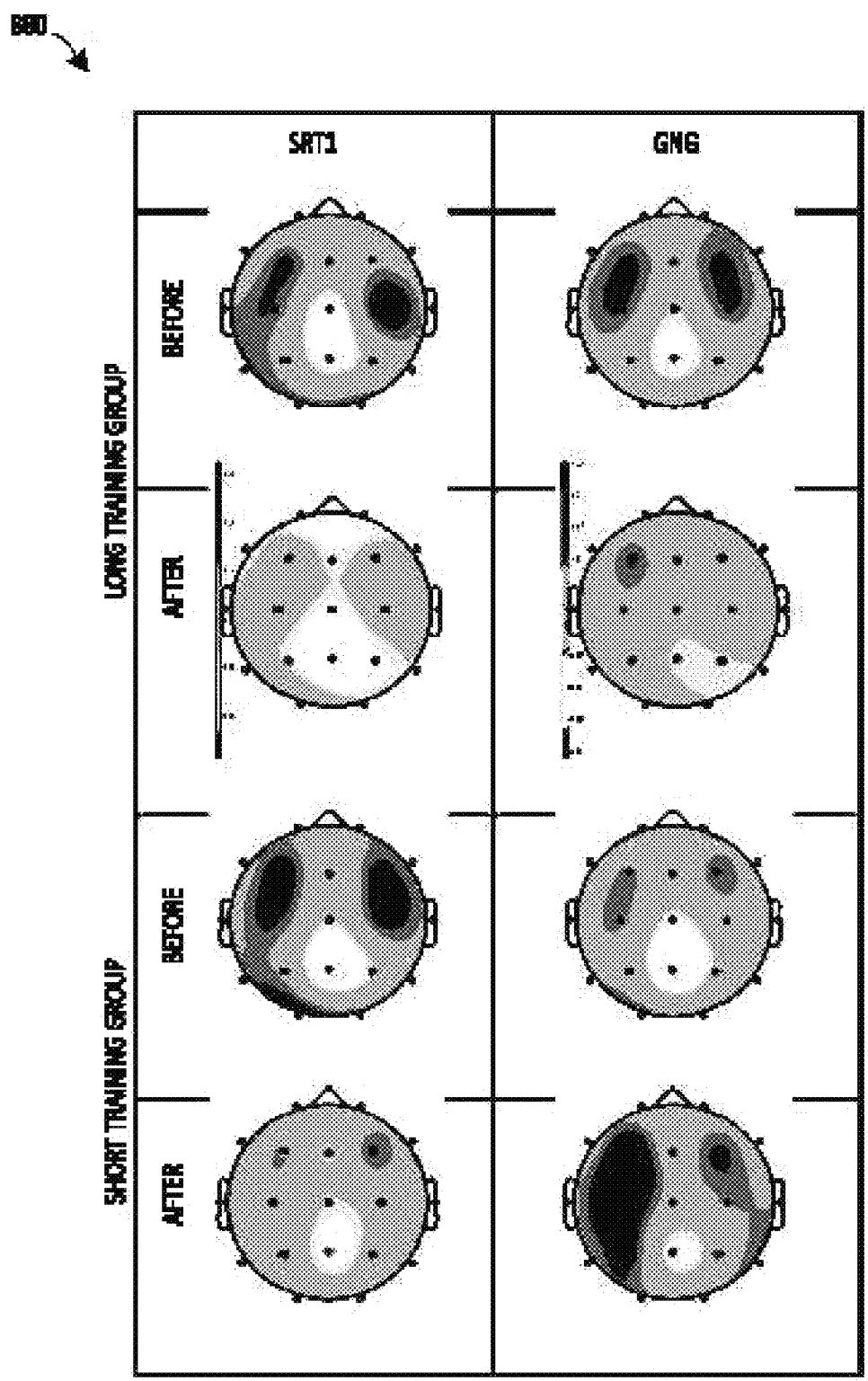
FIG. 28 illustrates major steps in the processing of electrophysical data.
Figure 29:
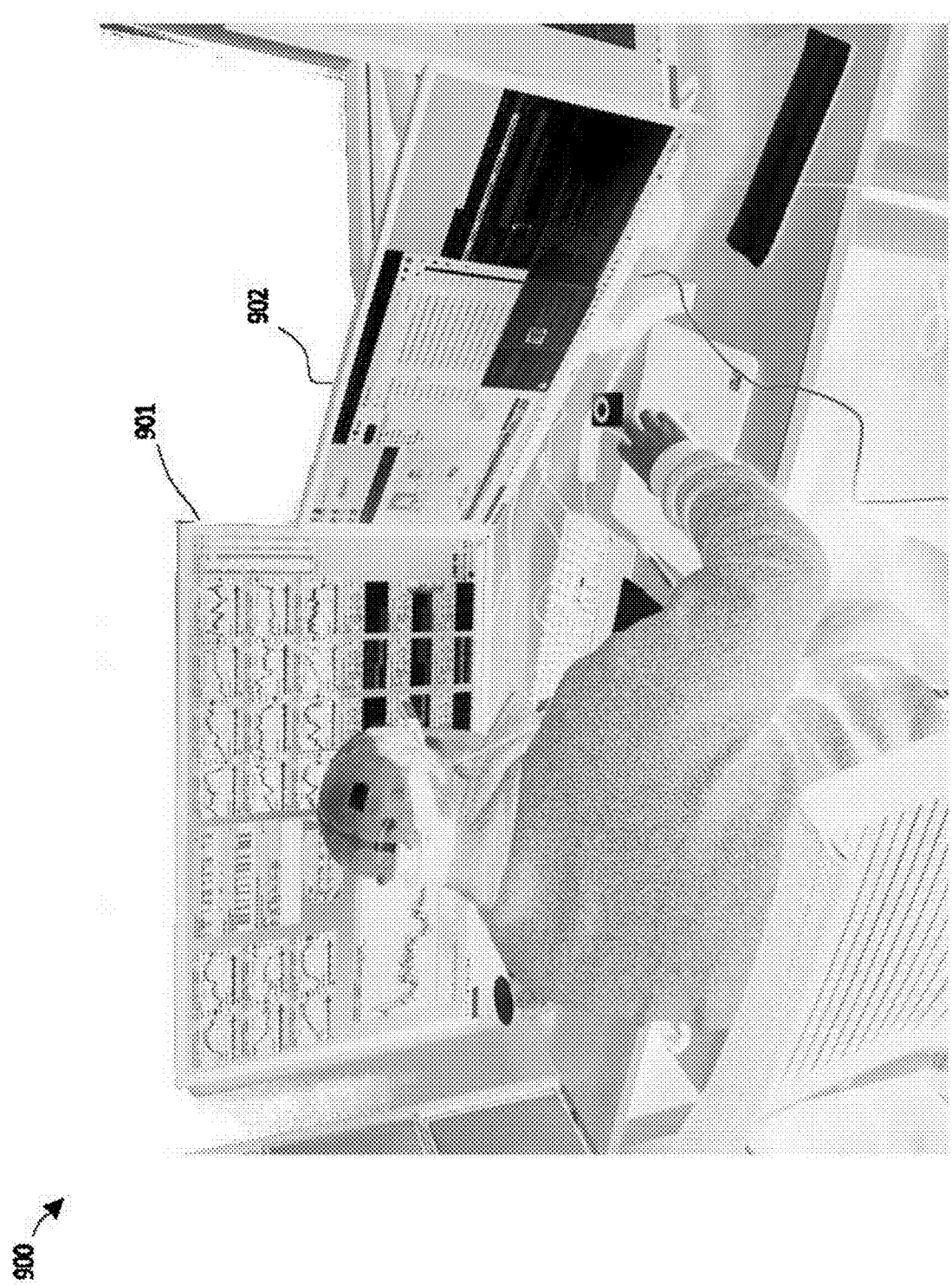
FIG. 29 illustrates a portfolio manager (PM) at a workstation in the PM case study.

FIG. 28 illustrates average workload EEG measures that were generated from the EEG data during the SRT1 and GNG tasks. Black and dark gray illustrate areas with high levels of activation. Mid-tones represent areas with moderate levels of activation. Light gray and white represent areas with low levels of activation.

Before training, both groups showed moderate bilateral prefrontal activation and low central/parietal activation. After training, for SRT1, both groups show smaller workload measurements across the head. For example, both groups show less bilateral prefrontal activation. This parallels the behavioral data—both groups performed the SRT1 task with greater efficiency after training. For the GNG task, however, the changes for each group were different. The long-training group showed decreases in the frontal regions while the short-training group showed increases in the same region. It appears that the long-training group was able to handle the task with less workload. The behavioral data showed that the long-training group performed the task better after training while the opposite for true for the short-training group. Thus changes in behavioral data had corresponding changes in neural data.

Executive functions (information processing, sequencing, decision making, planning) are associated with employee performance. This case study demonstrated that independent computer-based brain assessment and training provide a scalable solution to evaluate and develop executive functions, functions that are malleable throughout the lifespan. Brain training increased brain processing speed on a variety of neurobehavioral tasks. The further elaboration of the neuroplastic mechanisms that can underly these behavioral changes appear to be clarified by an electrophysiological measure of workload, indicating that the use of a cognitive state measure like engagement or workload would be useful as a classifier for providing neural feedback for further optimizing brain training and neuroplasticity.

Overall, the corporate study demonstrated positive benefits for the group of participants in several areas of neurocognitive performance. Further, significantly higher gains were recorded in the long-training group with moderate gains in the short-training group. It is very clear that several mechanisms of neuroplasticity occurred as a direct result of the program. More importantly, this study demonstrated that a cognitive state (e.g., workload performance) can support the further extension of real-time brain performance evaluations in the corporate environment. The loop of "measure-boost-track" was shown to be effective both qualitatively and quantitatively—and worthwhile results were seen with modest training, gains in attention, executive control and decision-making systems were present.

Portfolio Manager Case Study

A. Background and Setup

It has long been recognized, but little understood, that professional financial risk-takers go in and out of different mental "states" during their workdays, and that certain mental states are associated with more profitable decision-making than others. For example, many professional risk-takers are familiar with a feeling commonly described as "being in the zone." Qualitatively, when one is in the zone, time feels as if it slows down, and the risk-taker often has the sense that they can intuitively "feel" where the market is headed. Scientific evidence suggests this zone is not only a real phenomenon, but also tends to be associated with significantly better decision-making, and thus, superior financial performance to what is typically experienced in other mental states.

There are several well-described problematic mental states that risk-takers can also experience—including cognitive overload, the "fight or flight" response, and cognitive fatigue—each of which is associated with below-average market performance. However, it has been hard to measure risk-takers' mental states with any precision, making these states difficult to optimize.

In late 2018, Applicant conducted a research study to understand and characterize the impact that neurophysiological factors have on the financial performance of portfolio managers, who must make rapid, complex decisions under high-stress conditions. The specific intent was to identify measurable neurophysiological "states" that are reliably correlated with performance.

Four professional traders (also referred to as "portfolio managers" or "PMs") were provided with a minimum of $50,000 each to conduct transactions with and allocate to no more than ~10 positions. Each of the PMs had extensive prior professional experience and were screened and recruited from a pool of more than one hundred applicants based on a variety of factors including their experience and track record. For their work, the traders were compensated solely on the basis of their performance—a percentage of the profits they generated—except for one trader, who was additionally compensated $5000/month for performing managerial activities.

In order to simplify the analysis, participants' trading activities were limited to liquid US equities and exchange-traded funds. Their PMs' activities generated over 9500 transactions—such as buy, sell, short sell, execute, cancel, and cancel/replace—over nearly 40 days of trading between mid-October 2018 and mid-December 2018, which incidentally happened to coincide with a highly volatile near-bear-market correction. Over 4000 of these transactions were executed and graded to measure the traders' performance. Table 3 lists the number of executions, average number of daily executions, and average number of securities traded daily for each of the traders.

TABLE 3

Transaction Summary

| PM | Executions | Avg/Day | # Securities Traded | Dates |
|---|---|---|---|---|
| Subject 1 | 781 | 24 | 15 | Oct. 19, 2018-Dec. 14, 2018 |
| Subject 2 | 714 | 24 | 12 | Oct. 22, 2018-Dec. 14, 2018 |
| Subject 3 | 826 | 27 | 7 | Oct. 26, 2018-Dec. 14, 2018 |
| Subject 4 | 1683 | 89 | 12 | Nov. 14, 2018-Dec. 14, 2018 |
| Total | 4004 | 164 | 46 | Oct. 19, 2018-Dec. 14, 2018 |

The PMs were provided with a room in which to perform the trades, so that they could communicate with each other to better resemble typical trading conditions. Each PM had a dual-monitor trading platform 900 (FIG. 29), wherein one monitor 901 presented a professional trading platform—the Lightspeed Sterling Trading Platform™—with charts, numbers, execution windows, etc., and the other monitor 902 enabled the trader to monitor financial news about the market and specific companies. The PMs were encouraged to begin trading with the opening bell and continue trading through most or all of the day. Typically, the PMs decided to close out their positions by the end of the day.

The study transpired against a backdrop of what is widely acknowledged to be one of the more difficult investment cycles of the last decade. To be specific, it took place in the midst of a broad market selloff that took the S&P 500 index from a late September high of 2930 to a Christmas Eve low of 2351. This approximate 20% correction was the largest such downward move for broad-based indices since the market collapse of 2008/2009. Over this same time period, the Chicago Board Options Exchange's Volatility Index (VIX), widely acknowledged as the benchmark barometer for the level of risk perceived to be present in the markets, rose by roughly 200%—from its September low of approximately 12 to its Christmas Eve apex of 36.

B. Data Collection

To collect physiological and transactional data, the PMs were instrumented with electroencephalography (EEG) headsets, head worn wireless eye tracking glasses (with pupillometry), and galvanic skin sensors as they traded this real money and engaged in various types of transactions. A channel on the EEG headset provided heart rate (HR) and HR variability (HRV) data, which was considered preferable to using wrist/hand worn sensors to perform that function. The EEG caps had twenty-four channels for continuous monitoring of brain activity, sufficient to track brain states that are represented in both space (functional anatomy) and spectra (frequency of brain activity). Eye tracking and monitoring sensors also collected data that was useful not only for filtering out artifacts in the EEG data but also tracking what the PM was looking at in the prelude to making a transaction.

Using the above-described equipment, continuous neurophysiological data was collected from the PMs from the moment the markets opened until the conclusion of each day's session. Study personnel were on site continuously during the study to help with equipment set-up and cleanup. The data from these neurometric and physiological sensors were collected by a laptop computer, automatically time stamped, and combined through Lab Streaming Layer™, an open source piece of software that facilitates synchronization of physiological and neurophysiological signals with one another. Due to limitations in the initial investigation set-up, hand coding to synchronize the physiological data with the transaction data was performed, but it is feasible to align the physiological data with the transaction data automatically.

Collected transactional data included the time of the order and execution (if any), the record ID, order ID, execution ID, type, price, quantity, status and Sterling log of the transaction, and the name of the trader and identity of the bond, stock, security, or fund that was the subject of the transaction, were collected through the professional trading platform. Data about the profitability of the trades, market values (including volume weighted average price or VWAP), trading volumes, and market conditions were also collected. VWAP is a measure of the average price at which a transaction is executed over a specified time period as compared with a market-based average. It is routinely used in the financial industry as a measure of the efficiency and effectiveness of transaction executions. While 30-minute intervals were used for the study, other intervals, and even multiple intervals, could be selected for VWAP.

In addition, a team of general risk advisors monitored all positions and timing associated with transactions and provided daily summary reports for each trader. Furthermore, each trader maintained a daily log of their experiences, including the trader's feelings, impressions, and observations of their own behavior during the course of the day.

C. Data Analysis and Findings

The initial focus of the data analysis was on the EEG data, and in particular, brain states modeled in the functional connectivity (FC) of the EEG space. The data analysis used the data-conditioning pipeline 850 shown in FIG. 31 began with preprocessing 851 (i.e., "cleaning") the raw electroencephalogram (EEG) data 852 that was collected. Next, a functional connectivity state estimation 860 (FCSE) was applied to the data. After the brain states that the PMs occupied during their trading day were identified and characterized, subsequent analysis incorporated physiological sensor data and financial data (e.g., the PM's transactions in comparison with VWAP statistics) as well. This created a cohesive data set. A description of the methodology employed to process the data and characterize the PMs' brain states is provided below.

The input data 852 comprised the raw data sampled by twenty sensors that the PMs were equipped with. As such, the input data 852 comprised twenty dimensions, one dimension per sensor. The preprocessing 851 of the input data 852 involved several independent filtering steps (with respect to some of which steps, the order is not important). The raw data was filtered (854) through low-pass (<1 Hz), high-pass (<32 Hz) and Notch (60 Hz) filters to remove slow-drift, high-frequency and AC-voltage-induced line-noise artifacts. This was followed by standardization (856), which removed the effects of reference electrode placement. Electrodes close to the reference electrode tend to have low voltages and electrodes far from the reference electrode tend to have higher voltages. Standardization (856) made the range of measurements across the twenty electrodes more uniform.

A blind, unsupervised robust PCA (857) (of which the standardization (856) can be considered a part, depending on how one defines PCA) was also performed. The PCA (857) imposed a smoothness condition on the data, which removed, for example, anything in the data that was punctuated at just one single electrode. The preprocessing PCA 857 refined the data into a data set that removed the big artifacts and approximated the multivariate data with a low-rank approximation that interpolated over deviations from smoothness. But most of the dimensions remained.

It should be noted that the PCA 857 performed as part of the preprocessing 851 was distinct from the PCA 861 performed as part of the FCSE 860. In general, PCA 861 is a process for finding a dimension-reducing orthogonal linear transformation of a multi-dimensional data set whose components maximally contribute to the variance of the data. This process involves a number of steps: (1) multivariate signal data is arranged into a matrix of observed signals; (2) the mean and variance are computed of the data collected by each sampler over time; (3) the data is standardized so that it has a mean of 0 and a variance of 1; (4) the covariance between each of the variables is determined and used to construct a covariance matrix; (5) the eigenvectors and eigenvalues of the covariance matrix are found in order to identify the principal components of the data; (6) a selected number of components are chosen to represent the data in a PCA-transformed space; and (7) the signal data is mapped onto the PCA-transformed space.

In this implementation, the preprocessing PCA 857 was not used for the primary purpose of reducing the dimensionality of the data. Rather, it decomposed the data into signal and noise. The preprocessing PCA 857 removed sparse noise components. It did a good job of removing high amplitude transient artifacts.

PCA is often used to transform data from one coordinate space (e.g., the sensor space) to another (i.e., the PCA space). Here, the noise was removed in the PCA space, and the data thereafter transformed back into the sensor space.

Next, bad channels—defined as channels whose power exceeds four standard deviations of the average channel—were rejected (858). Similarly, bad samples—defined as channels whose power exceeded four standard deviations of the average power within the sample's channel—were also rejected (859).

After the data was preprocessed 851, the process of FCSE 860—to identify and characterize the brain states that the PMs occupied—began with a machine learning program that, once again, was blind and unsupervised. In this particular case study, PCA 861 was once again used. In the alternative, ICA could be used. The data input into the study consisted of twenty dimensions of denoised time-domain sensor data.

Oftentimes, when PCA is done, an a priori selection of the n-most principal components is made in which to further resolve the data. Alternatively, n is left open, dimensions are removed one dimension at a time, and a determination is made for when to stop. However, this alternative is computationally expensive. Early in this case study, a set of data was resolved into three, six, and nine principal components. The "knee point" in the PCA scree plot—which shows the cumulative explanatory power of the components, arranged in descending order—was consistently located between six and nine principal components. (A "knee point" in a curve is a point where the curvature has a local maximum. The components accumulated up to this point explain most of the variability of the data). Any accumulation above nine principal components simply introduced noise. The use of anything less than three components did not yield enough information. Accordingly, it was decided, for reasons of computational efficiency, to use six principal components for the FCSE PCA 861.

As an unsupervised process, the PCA 861 transformed the PMs' neurophysiological data into a space that efficiently represented their brain activity as a set of nodes. In block 862, each component of PCA-transformed data was filtered, via a band-pass filter, into four physiologically relevant frequency bands—namely, beta, alpha, theta and delta—in order to discover if any patterns emerged from the data. This band-pass filter step 862 transformed the data set from six dimensions (yielded by the six components) into twenty-four dimensions (i.e., the product of the six components and the four frequency bands), each dimension being represented by a sequence of data.

In block 863, each of the twenty-four data sequences was Hilbert transformed to calculate the "envelope" of each channel. It will be noted that each of the twenty-four time-domain data sequences represented an oscillating signal. The "envelope" of an oscillating signal is a smooth, typically modulating curve outlining the amplitude of the signal. The envelope corresponds to the power within each of those bands and each of the principal components. Each of those envelopes is processed temporally. For each of the brain sources, it provides access to the temporal signals being generated by those sources.

In block 864, the functional connectivity was estimated as the correlations of these frequency-specific and component-specific envelopes. 24×24 correlation matrices regarding the neural activity were computed using a sliding time window, which quantified the co-fluctuations (co-modulations) in the envelopes. It will be noted that correlations between the envelopes does not equate to correlations between the underlying signal frequencies themselves, but rather to correlations in the slow-moving modulations of the amplitude or power of those signals. As such, correlations are representative of the connectivity between the nodes, and the generation of these correlation matrices yield distinct functional connectivity patterns. Block 864 made it possible to differentiate the traders' brain states based on whether or not they were exhibiting functional connectivity among specified brain regions.

Next, in block 865, cluster analysis was used to group the data of the correlation matrices into clusters, each of which can be characterized as representing a "brain state." While it is possible to rely on heuristics to define the clusters, in this implementation the well-known "k-means" algorithm was employed because it is particularly well-adapted to large data sets. There are many other common algorithms and various permutations thereof that can alternatively be employed in cluster analysis, including hierarchical, centroid-based, distribution-based, and density-based algorithms.

A decision was made to characterize each of the clusters as "brain states." These brain states were not defined in advance. Like the clusters themselves, they emerged from the PCA-transformed data. As it turned out, these brain states ranged from highly connected to loosely connected.

Figure 38:
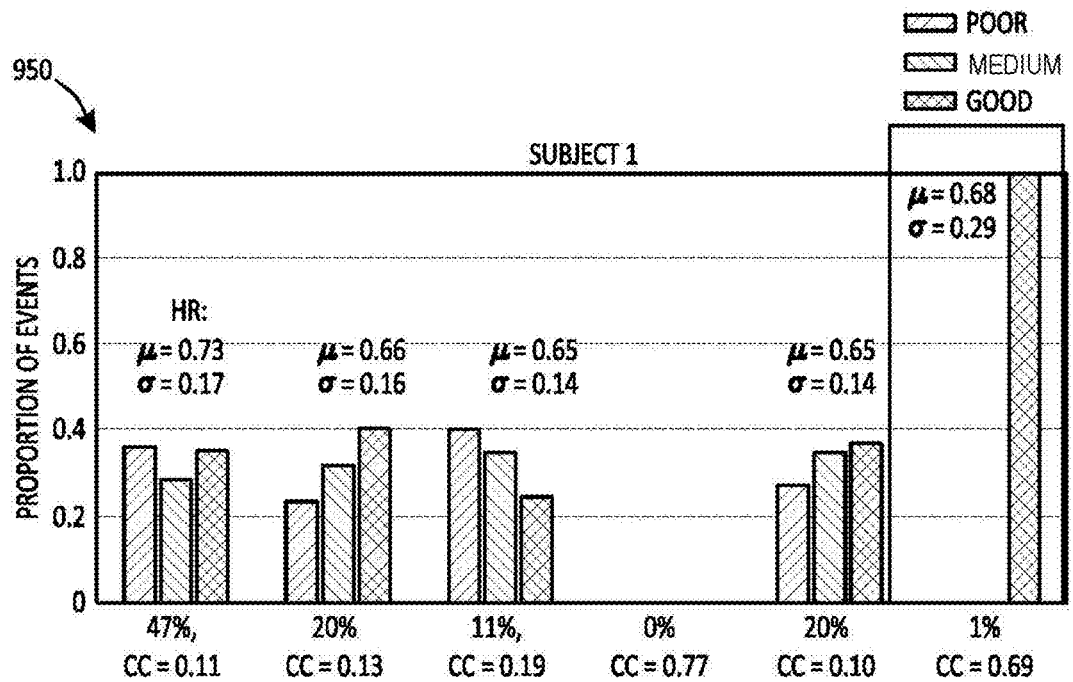
FIG. 38 is a clustered bar chart showing a first PM's proportions of "poor," "medium," and "good" trades as a function of the first PM's brain states.
Figure 39:
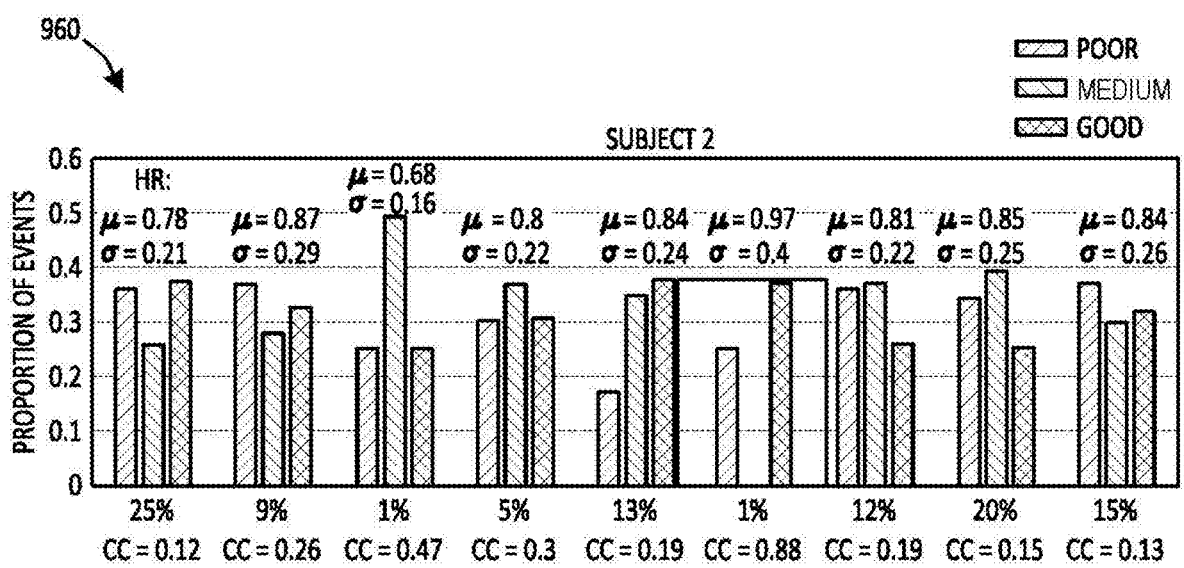
FIG. 39 is a clustered bar chart showing a second PM's proportions of "poor," "medium," and "good" trades as a function of the first PM's brain states.
Figure 40:
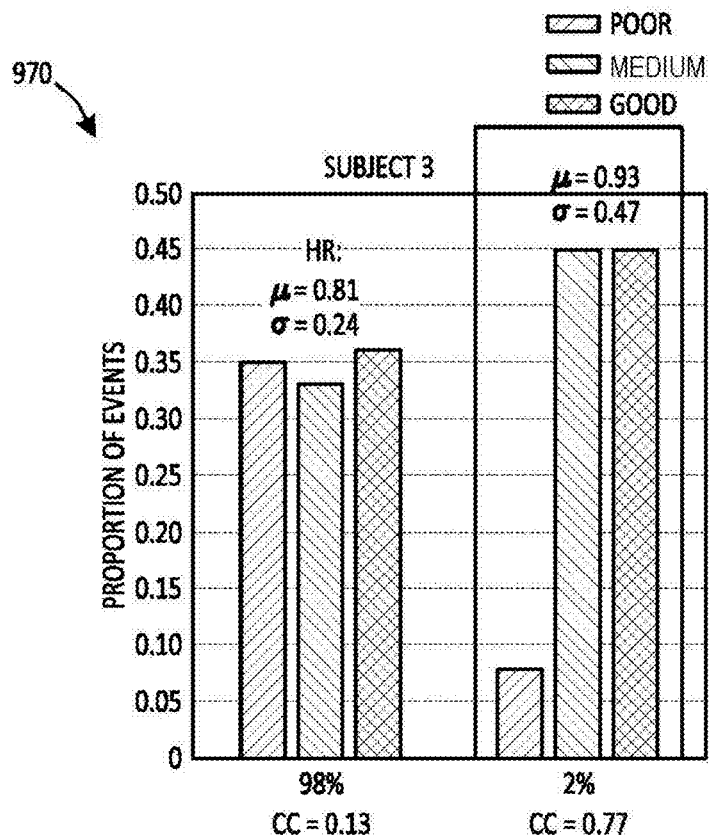
FIG. 40 is a clustered bar chart showing a third PM's proportions of "poor," "medium," and "good" trades as a function of the first PM's brain states.
Figure 41:
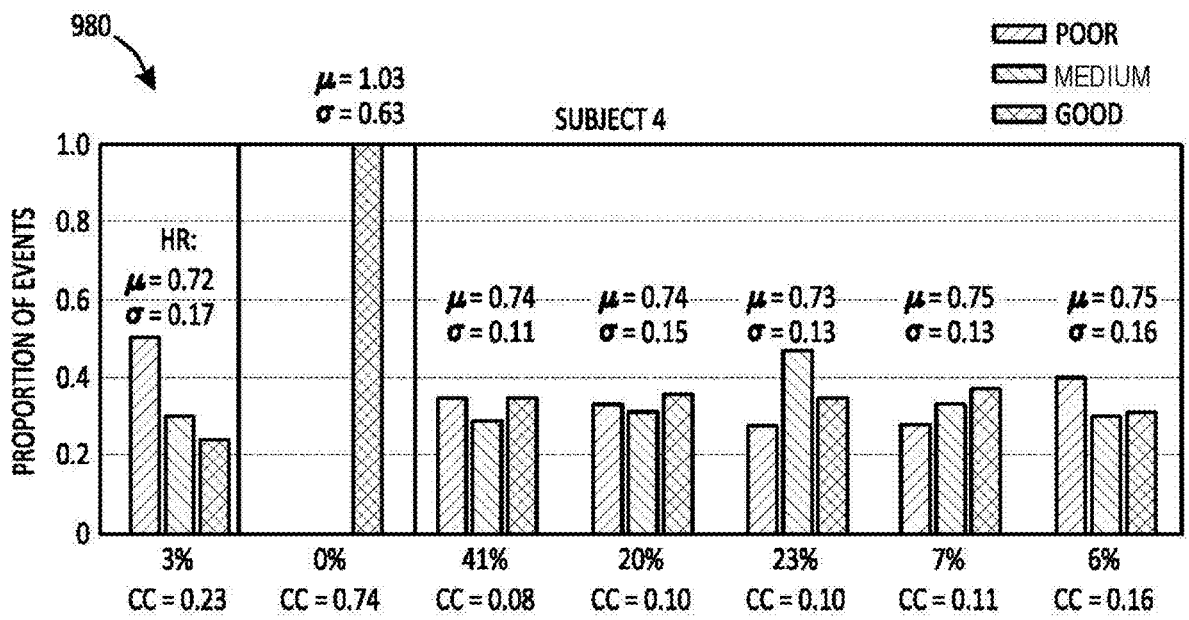
FIG. 41 is a clustered bar chart showing a fourth PM's proportions of "poor," "medium," and "good" trades as a function of the first PM's brain states.

The number of clusters is a function of both the data set (and whatever clusters emerge from the PCA transformation) and the heuristic or cluster algorithm and related constraints chosen to group the data. Here, the number of clusters identified was not determined a priori. Indeed, different numbers of clusters were identified for each of the PMs. FIG. 38, for example, shows six sets of clustered bars, each set of which corresponds to an identified cluster in the data. FIGS. 39, 40, and 41, by contrast, show 9, 7, and 2 sets of clustered bars, respectively.

In this case study, initially only the EEG data was analyzed in the preprocessing PCA 857 and FCSE PCA 861. In an alternative embodiment, the input data 852 would be expanded to include data from other sensors, such as the heart rate. However, applying PCA or ICA to data from such disparate groups of sensors would cause the sensor data exhibiting the greatest variability to drive the PCA analysis. Therefore, analyzing data from just one set of sensors at a time makes it easier to identify brain states and other physiological states useful in predicting performance.

Figure 31:
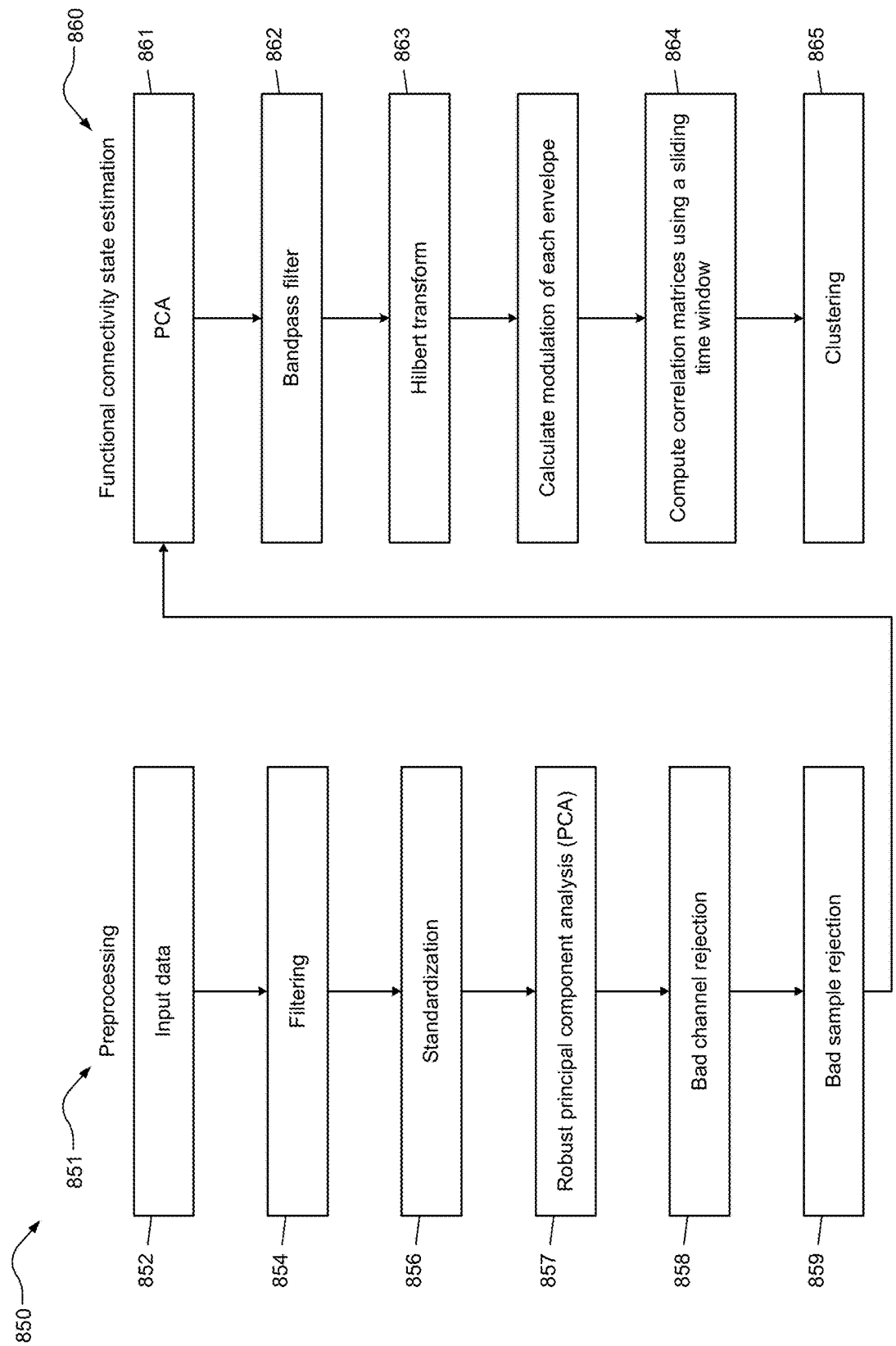
FIG. 31 is a flowchart illustrating steps of an EEG preprocessing and functional connectivity analysis.

Some of the steps performed in the data-conditioning pipeline 850 shown in FIG. 31 could be performed in a different order. Except for a claim, if any, that states otherwise, the invention is not limited to this particular data-conditioning pipeline 850, the particular order of the steps shown in the data-conditioning pipeline 850, and the invention does not require every step of the data-conditioning pipeline 850. Also, the invention encompasses adaptations of the data-conditioning pipeline 850 to other data sets, activities, and occupations.

In summary, the data-conditioning pipeline 850 comprises filtering signal data taken from an electrode space, transforming it into a principal-component space, identifying a temporal evolution of those spatial components, and finding the correlation between them.

Figure 36:
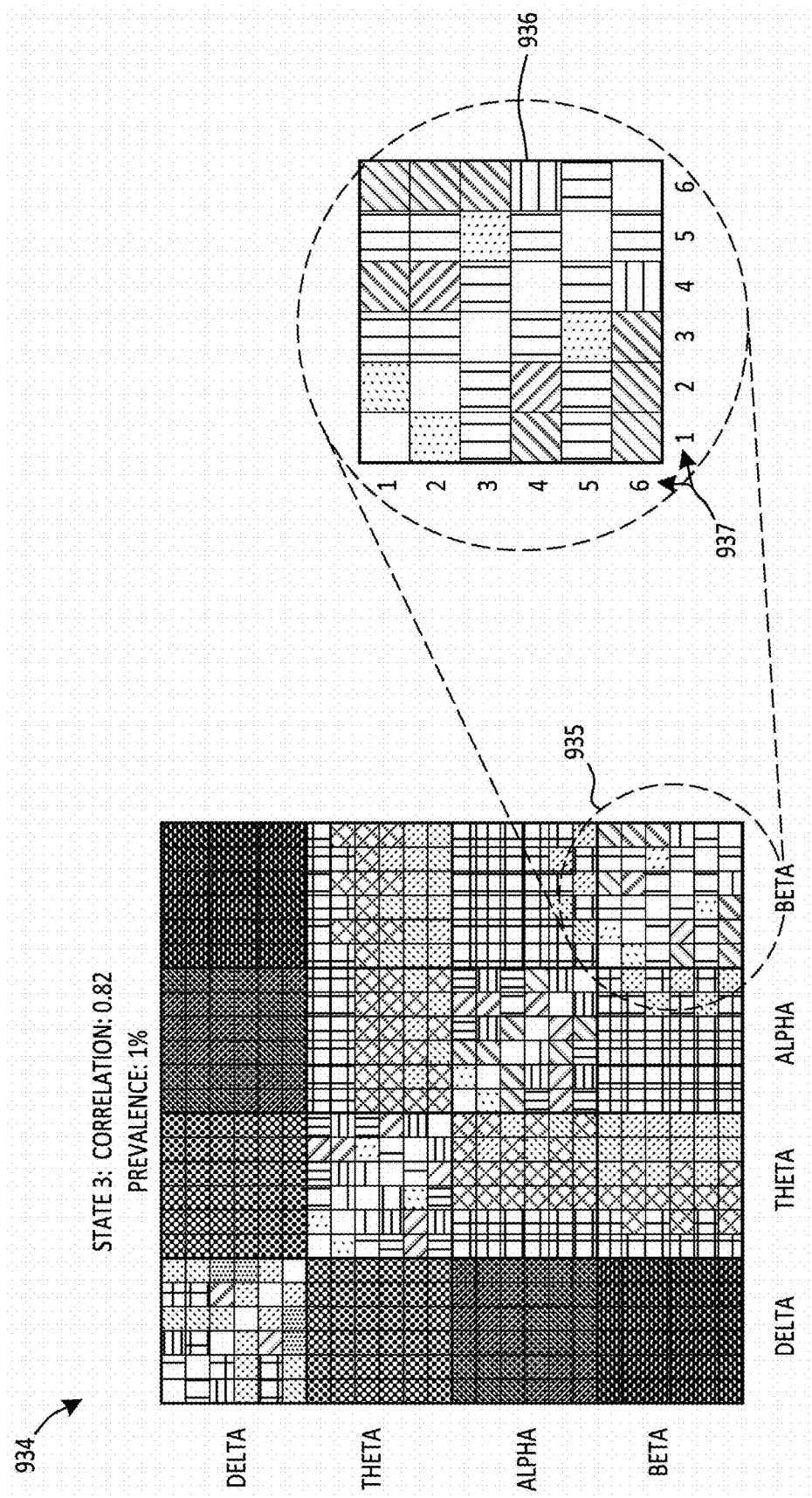
FIG. 36 is a plot like that of FIG. 34, but for a third brain state.

FIGS. 34-36 illustrates three functional correlation (FC) "heat" maps for three data-driven brain states that were not defined a priori but rather emerged from the unsupervised PCA analysis using n=6 components. Each of the brain maps correspond to visually recognizable and algorithmically identifiable "clusters" of data in the PCA-transformed coordinate space. FIG. 34 illustrates a first state 930—representing a relatively unfocused and disengaged state—that was prevalent 64% of the time. There was only a low correlation (0.13) between brain waves. FIG. 35 illustrates a second state 932—representing a slightly more organized and engaged state—that was prevalent 35% of the time. Here, there was also a low correlation (0.22) between brain waves. FIG. 36, by contrast, illustrates a third state 934—representing the most organized and engaged and connected state— which exhibited a high correlation (0.82) between the alpha (8 to 12 Hz), beta/low gamma (12 to 38 Hz) and theta (4 to 8 Hz) brain waves. Delta waves—the lowest frequency (0.5 to 4 Hz)—were relatively uncorrelated with the other three brain waves. This third state was present only 1% of the time.

In each of the FC heat maps 930, 932, 934, different intensities of connections between various frequencies (beta, alpha, theta, delta) and the components (illustrated in little boxes in each set of larger boxes) are represented by the relative darkness (meaning relatively uncorrelated) and relative lightness (meaning relatively correlated) of the large boxes 935 at the intersection of two different brain waves. The intersections between two of the same brain waves define an n×n set of smaller boxes 936, each of which illustrates the correlations between the six components 937 identified by the PCA. While in U.S. Provisional Patent App. No. 62/831,134, color was used to represent the different intensities—i.e., heat map with "hotter" colors (e.g., red) showed that the brain was exhibiting a higher degree of functional connectivity—here Visio®-generated patterns are used to represent relative levels of correlation, rather than shading, because for purposes of uniformity and form, colored and shaded drawings are discouraged within the Patent and Trademark Office. Patterns were selected based upon what appeared to be the ratio between white and black within the pattern. The darker the pattern, the less the correlation and functional connectivity. The lighter the pattern, the greater the functional connectivity. It is evident that the brain state represented by FC heat map 934 exhibited a great deal more functional connectivity than the brain states represented by FC heat maps 930 and 932.

Analysis of the PMs individually produced similar graphs. In particular, the analysis identified one state for each PM in which the brain waves were highly correlated relative to the other states. A significant finding of the case study was that the functional connectivity (FC) pattern identified in the unsupervised analysis was remarkably consistent among the PMs. This indicates that a signature could be derived from the patterns, representing a distribution of correlations that fall within bands (e.g., p=0.45 to 0.55)

Also, applying the PCA using fewer components (e.g., n=3) resulted in significantly less correlation than when six or nine components were evaluated, but there was comparatively little difference between using 6 and 9 components. While for simplicity, only a single set of graphs are illustrated in these drawings, additional patterns are illustrated in U.S. Provisional Patent App. No. 62/831,134, which is incorporated by reference.

The analysis next proceeded to evaluating the extent to which the brain states predicted the quality of the PMs' transactions using VWAP as a metric. Since no information about the PMs' VWAP scores was used to estimate the FC patterns (i.e., the method was unsupervised), transaction-level VWAP scores were grouped together as a function of the FC pattern the PMs were experiencing when transactions were made. Time envelopes—e.g., 6 seconds—were selected around each transaction with which to associate the neurophysiological and VWAP performance data.

Figure 37:
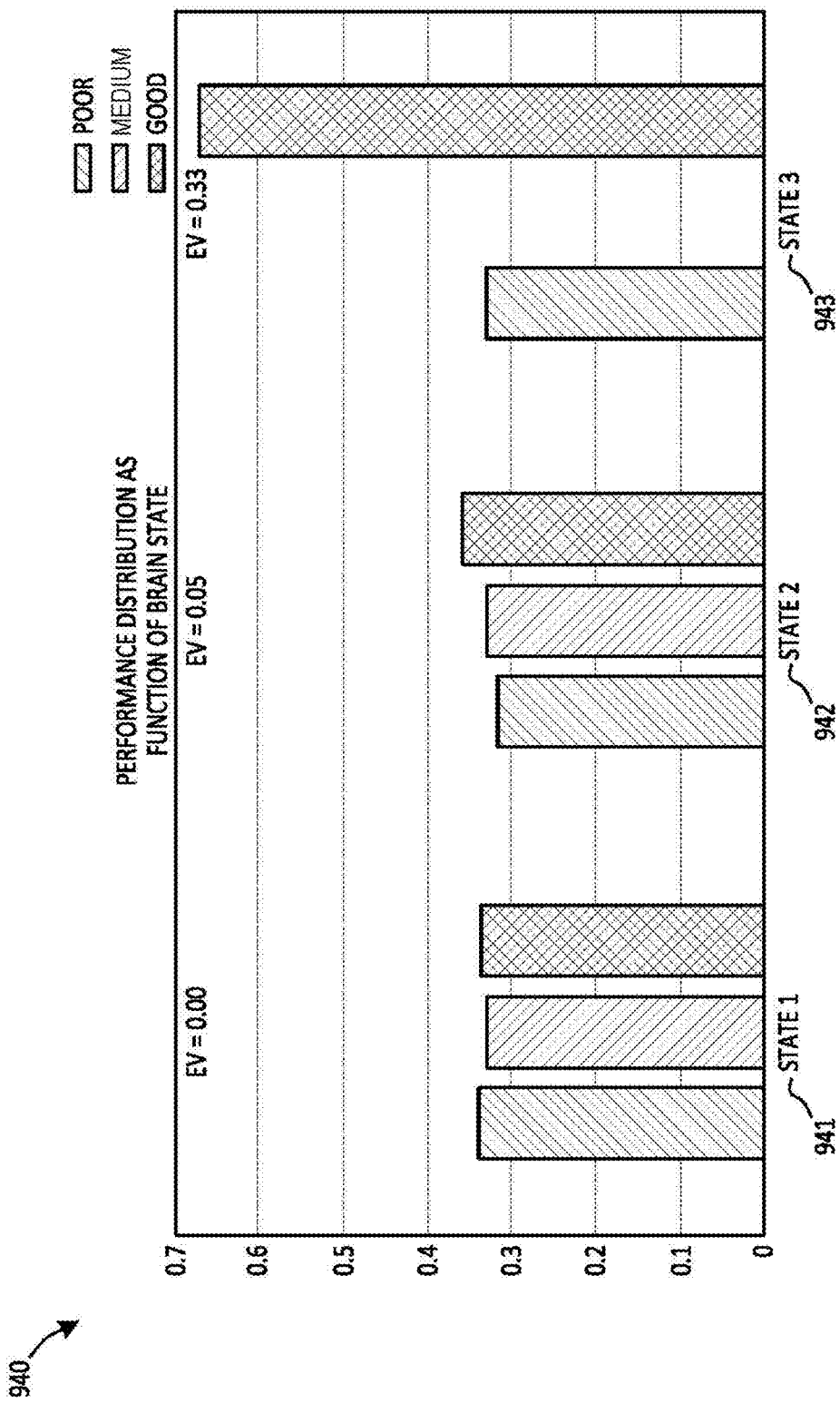
FIG. 37 is a clustered bar chart illustrating the proportions of "poor," "medium," and "good" trades as a function of brain state, for three brain states, along with the average or expected quality of trades for each of the three states.

FIG. 37 is a clustered bar chart 940 paralleling FIGS. 34-36 that illustrates how well the PMs performed in each of the three identified states. Performance was graded as a function of the trader's trades in relation to the VWAP. Purchases and sales of securities whose prices were in a VWAP-centered band in FIG. 37 categorized as "medium," meaning that they fell into a middle-range—here, a middle tertile.

Sales whose prices were above that band and purchases whose prices were below that band were categorized as "good." Contrariwise, sales whose prices were below that band and purchases whose prices that were above that band were categorized as "poor."

The first state 941—representing transactions conducted while in a relatively unfocused and disengaged state—was statistically uniform across three grades, meaning that PM's trades were evenly distributed across "poor," "medium" and "good." Note that other gradations are possible and fall within the scope of the invention. State 1 exhibited no statistical effect on the PM's performance. The second state 942—representing transactions conducted while the trader's brain was in a slightly more organized and engaged state— was also fairly uniform across the three grades, exhibiting just a small positive effect on the PM's performance. The third state 943—which represented the high-connectivity state in FIG. 36—also exhibited a more significant positive effect on the PM's performance. However, only three transactions—two "good" and one "poor"—occurred while in state 3.

As reflected in FIGS. 38-41, the analysis was expanded to each of the PMs, i.e., Subjects 1-4, individually. The data was clustered into 6 states, 9 states, 7 states, and 2 states, respectively, for Subjects 1-4. Each clustered set of bars represents an identified brain state, and the label below each clustered set of bars indicates the prevalence of the brain state and the correlation coefficient between the brain wave patterns of that state. Above each clustered bar is data (mean and variance) about the PM's heart rate (HR) for each brain state, computed in seconds as the mean time between R-R intervals. In each figure, an elongated box is drawn around the cluster/brain state that exhibited the most positive performance. It should be noted that while the clustering of brain connectivity data into different states differed with each PM, the states could be rearranged in an order that progressively represent greater levels of brain connectivity.

The analysis found that high heart-rate variability (HRV)—the variance of the heart rate—was generally correlated with more highly connected brain states. For example, in FIG. 38, the HRV during the highest-FC brain state was 0.29, considerably higher than the values measured for the other states. In FIG. 39, the HRV during the highest-FC brain state was 0.4, once again larger than the HRVs measured for the other eight brain states. In FIGS. 40 and 41, the HRV during the highest-FC brain states (0.47, 0.63) were also larger than the HRVs (0.24, 0.17, 0.11, 0.15, 0.13, 0.13, 0.16) for the other states.

HRV—measured as the variance or standard deviation of the heart rate—is commonly associated with increased activity of the parasympathetic nervous system along with decreased sympathetic nervous system activity. Accordingly, high HRV data can be interpreted as a sign of decreasing arousal or stress. In Subject 1, the highest HRV (i.e., $\sigma=0.29$) was associated with the subject's best overall performing brain state. Likewise, for Subject 2, the highest HRV (i.e., $\sigma=0.4$) was associated with the subject's best performing brain state. Subjects 3 and 4 had highest HRVs (i.e., $\sigma=0.47$ and $\sigma=0.63$, respectively) that were also associated with the subjects' best performing brain states. This demonstrates that HRV, quite apart from EEG, provides a useful way of predicting a PM's performance, and can even be substituted for EEG.

In summary, each subject exhibited at least one state strongly correlated with good or superior trading performance. The PCA involving six principal components provided better results than the PCA involving three or nine principal components. The inventors found that "good" brain states were generally associated with brain states having high mean absolute correlation and low prevalence. Moreover, high HRVs were also associated with better performance.

Applicant also analyzed the data using with max-kurtosis independent component analysis (ICA), which is fast and can handle large data arrays. However, there was so much noise in the data, in this particular case study, that it overly influenced what the components looked like. PCA tries to collapse things into components and essentially compress the data; ICA by contrast, provides maximal separation between components. Different case studies could very well produce better results using ICA.

For simplicity, these components can be categorized into two generalized brain states that each of the PMs went in and out of during their trading day. After all, a "state" can represent any detectable and characteristic pattern or collection of data. Because differences between different detected unfocused states is not likely to be meaningful, it is useful to characterize the states other than the focused state as a single generalized unfocused state, thereby yielding just two brain states.

Figure 32:
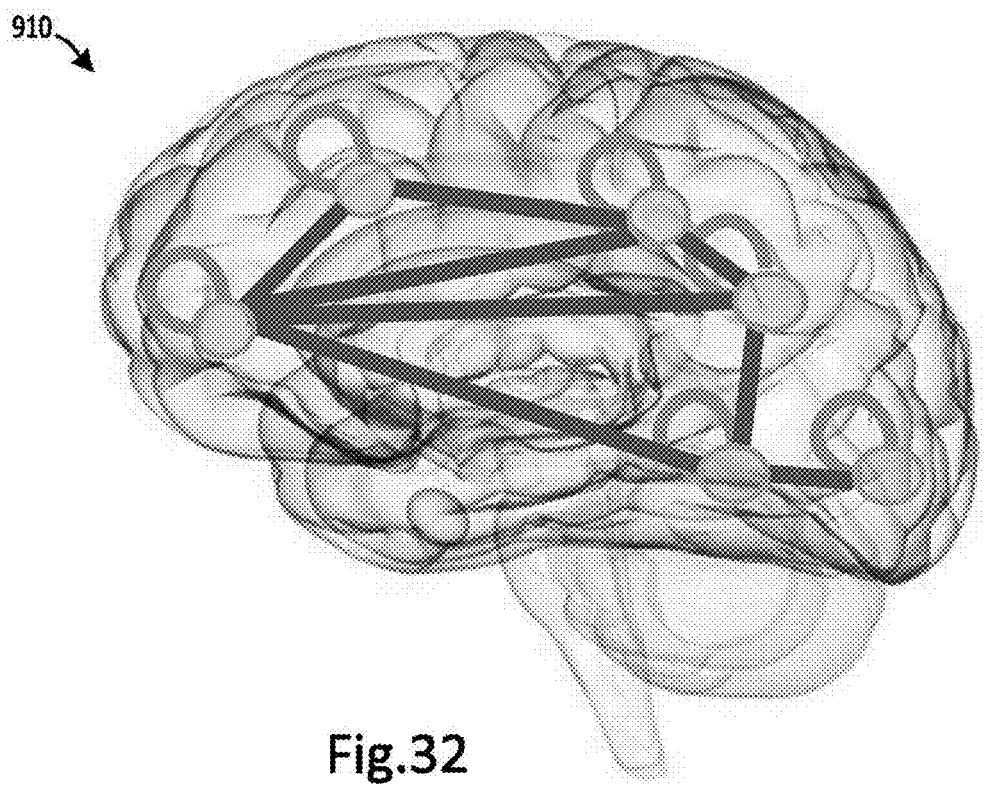
FIG. 32 illustrates a functional connectivity pattern that was associated with positive alpha.

In one of these states, the PMs' brains demonstrated a high degree of "functional connectivity," meaning that several distinct regions within their brains were functionally interconnected and operating in synchrony with one another. In the other state, this type of functional connectivity was not present. A comparison of these states with transaction scores led to the discovery of a correlation between functional connectivity and profoundly differing levels of performance. In the highly connected state, each of the PMs generated significant alpha, whereas in the other state, they tended to underperform the market. This is illustrated in FIG. 32, which shows alpha as a function of these two generalized states.

The high-connectivity state—which was in evidence less than 10% of the time—was highly correlated with profitable transactions for all four of the PMs as measured by VWAP. The low-connectivity brain state was associated with below-average performance. Statistical analysis showed a high degree of significance to these conclusions.

To test the statistical validity of the study findings, a Wilcoxon rank sum test was used for two unequal pooled measures where one pool consisted of the alpha values from all subjects during high connectivity states and the other was the pooled alphas from the subjects during low connectivity states. This analysis yielded a p value<0.05 and confirmed the statistical validity of the study's conclusions.

To access charts and execute transactions, PMs used the Lightspeed/Sterling™ platform—a professional trading platform geared toward experienced professional PMs. A risk advisor team monitored all positions and timing associated with transactions and provided daily summary reports for each PM. In addition, each participant maintained a daily log of their experience(s), specifically designed to record their feelings, impressions and observations of their own behavior during the course of the day.

The study benefitted in meaningful ways by taking place during a period of high volatility and general duress, as it allowed for the monitoring of both neurophysiological states and performance in scenarios that featured and often demanded cognitive attention at the upper ranges of what a typical risk-taker routinely experiences.

In the face of these market conditions, it was also clear that when measuring a PM's performance in association with individual transactions, it was important to factor out potentially confounding influences that the volatile market conditions might create. It was for this reason that trading performance was measured in comparison with the VWAP—a well-established trading metric that has broad validity even in highly volatile market conditions, making it an ideal baseline metric.

Figure 33:
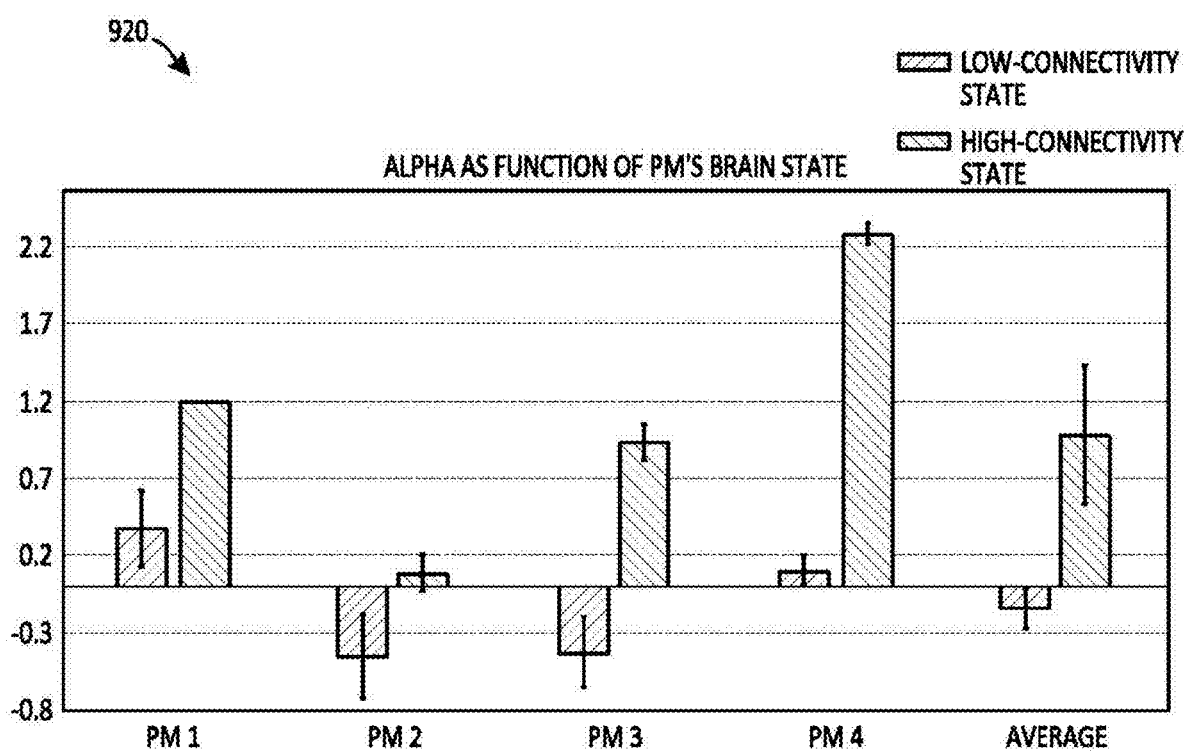
FIG. 33 illustrates the alpha of the PMs' trades as a function of whether they had a high-connectivity or low-connectivity brain state.

To summarize, the study identified two distinct and measurable brain "states" that each of the PMs went in and out of during their workdays. One of them was associated with high-alpha transactions (here, "alpha" refers to the performance in relation to VWAP scores, and is not to be confused with "alpha" brain waves) and the other was not (as illustrated in FIG. 33). The transactions that were associated with the high-connectivity state, while representing less than 10% of the total number of transactions, represented more than 100% of the total alpha generated in the study. This is a very significant finding. Table 4 below illustrates how good, medium, and poor transactions were distributed for the two brain states.

TABLE 4

Prevalence of good, medium and poor transactions for different brain states

| Transaction quality | Low connectivity | High connectivity |
|---|---|---|
| Good | 35% | 65% |
| Medium | 30% | 25% |
| Poor | 34% | 10% |

As also described earlier, the brain state that was associated with high-alpha transactions was characterized neurologically by a strong degree of connection and electrical synchronization between a number of brain regions that are commonly involved with complex decision-making. This functional connectivity pattern is illustrated in FIG. 31.

As illustrated by this study, it is possible to accurately measure and monitor, in real time, the brain states associated with both optimal and sub-optimal trading performance in a real-world setting.

D. Real-World Application

This information can be translated into real economic value. The research validates development of a finance-specific technological toolkit that reliably and materially enhances the profitability of—and offers a profound competitive advantage to—selected risk-taking organizations. The toolkit incorporates many elements of the experimental setup.

These inevitable neuroscience-based advances in the finance world are part of a broader evolutionary pattern. Since the advent of professional trading in the US under a buttonwood tree in lower Manhattan, a nonstop stream of technological breakthroughs—ranging from the invention of the tickertape, to the development of high-speed trading, to big data analytics—have steadily advanced the profession while offering those who take early advantage of them profound competitive advantages. Neuroscience represents a natural and critical next step in this evolutionary process and it, too, will offer early users a powerful competitive advantage.

In summary, the research study identified at least two distinct brain states that the traders went in and out of as they were working. One of these brain states—which was in evidence less than 10% of the time—was highly correlated with profitable transactions for all four of the traders as measured by an industry-standard metric commonly referred to as "Volume Weighted Average Price" (VWAP). The other brain state was associated with below-average performance. Statistical analysis showed a high degree of significance to these conclusions.

As a result of this study, the inventors claim as part of their invention the use of artificial intelligence, neural networks and machine learning to identify patterns and correlations between brain and/or other physiological state data and both optimal and sub-optimal/prime trading performance (or other high-risk decision-making), the use of neurometric feedback to predict such trading performance, the use by traders of neurometric feedback to enhance and motivate better brain states, and the use of neurometric data by risk managers and automated systems to determine whether a trader is having a bad day, whether to allow or block a transaction, and whether give the trader an intervention, etc.

Figure 30:
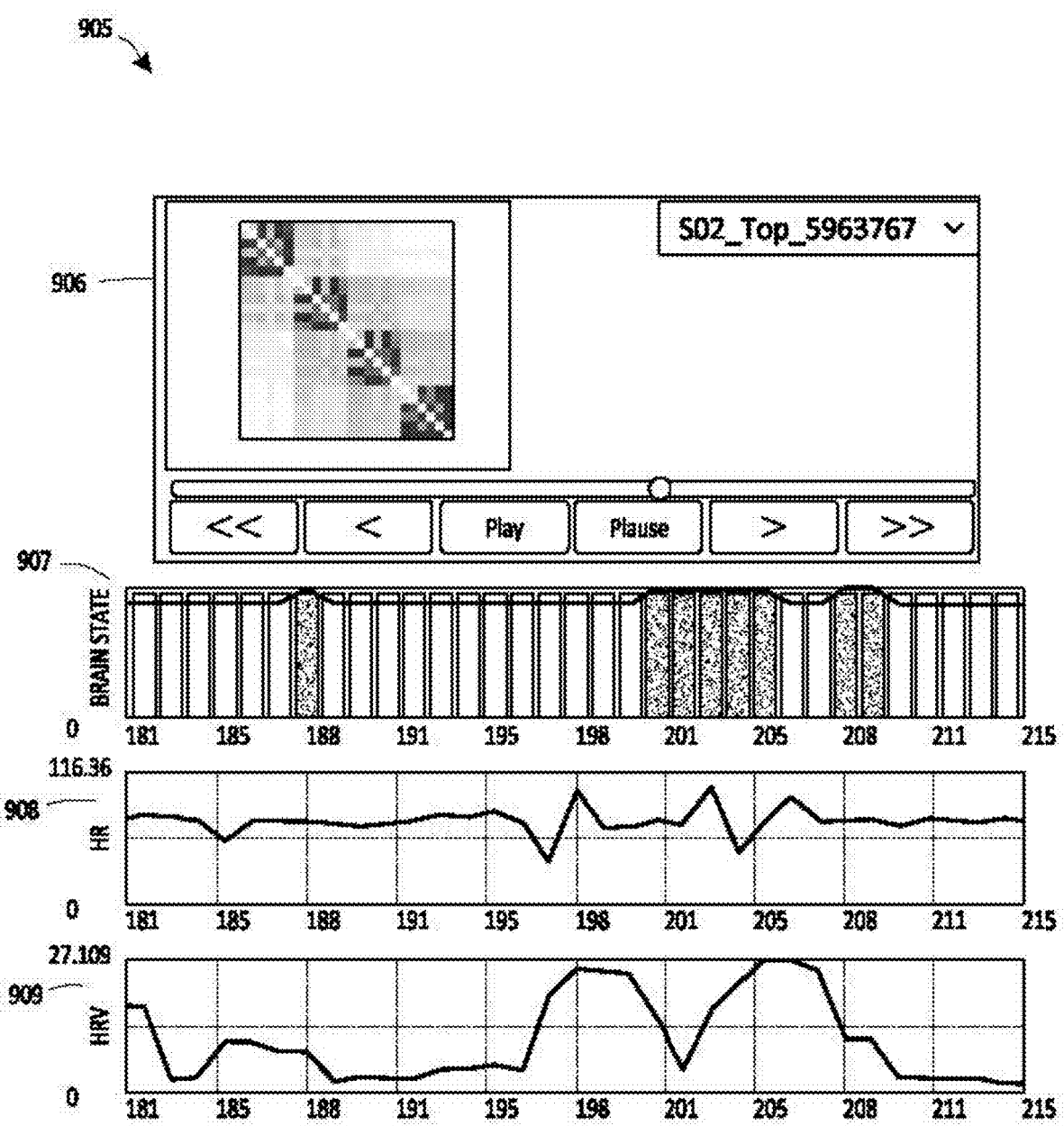
FIG. 30 illustrates a dashboard provided to the PMs.

FIG. 30 depicts an early version of a cognitive capture dashboard 905, which is an example of an interface that the trader can use in real-time to stay aware of their own brain states, pulse rates, pulse rate variability, and/or other physiological metrics. This embodiment of the cognitive capture dashboard 905 provides a moment-by-moment real-time "picture" of a brain state that the trader is in. This cognitive capture dashboard 905 provides a visual through a PCA matrix 906 (showing colored blocks) and/or a bar chart 907 that provides a moment-by-moment categorization of the state that the trader is in (via colors and bar heights). This cognitive capture dashboard 905 can also provide a running graphic 908 of the trader's heart rate and another running graphic 909 of the trader's heart rate variability. Advantageously, these live elements are time-synchronized or "aligned" with each other.

Furthermore, the cognitive capture dashboard 905 can provide a box or circle surrounding or a running eye gaze video displaying a focused view of the things (e.g., screen graphics, numbers, and text) that the trader is intensely focusing upon. The eye gaze feedback provides a focused visual reminder of what text, numbers, graphics, and/or surrounding elements the trader was looking at while contemplating a trade. It helps a trader assess what kinds of information triggered beneficial brain states, and what kinds of information tended to distract the trader.

It will be appreciated that when viewed in real time, the eye gaze feedback can not be necessary. But in another implementation, the trader can use the dashboard 905 to view a recording of clips of their transactions, much like a football or basketball team reviewing and studying footage of previous games. Such a dashboard could include one or more elements like those depicted in Illustration II (including the eye gaze feedback) as well as post-transaction feedback indicative of the goodness of the transaction.

Another embodiment of the dashboard 905 provides less detailed information, for example, a dial or red/green/yellow indicator regarding the trader's brain state. Yet another embodiment aligns the goodness of the transaction with the brain state and physiology in some dashboard-type form. In a managerial or supervisory embodiment of the dashboard, brain state and/or physiological signals and/or video feeds and/or goodness indicators of the trader or of several traders simultaneously are received and displayed to a manager or supervisor.

Many other refinements to the data analysis are contemplated. While the experimental data analysis focused on "states," finer-grained analysis is contemplated that focuses more on moment-by-moment or transaction-by-transaction physiological or neurophysiological signature. Also, while the "goodness" of a transaction was determined by its relation to VWAP, other measures of goodness—like profitability—are contemplated. Analysis is also contemplated to determine which kinds of information produce the best and worst reactions in a trader, and whether a trader tends to underreact or overreact to (or be overstimulated by) certain kinds of information, in order to better filter the data and dampen inputs that a trader receives and train the trader to react more optimally to information. Analysis is also contemplated to correlate brain states and physiological states (such as testosterone, adrenaline and cortisol levels and other arousal data) with trading performance data, informed by behavioral finance research such as described in John Coates *The Hour Between Dog and Wolf: How Risk Taking Transforms Us, Body and Mind* (2013), which is herein incorporated by reference. For example, it has been shown that periods of over-arousal correlate with bad decision making. Adrenaline comes on line first. Then stress hormones (e.g., cortisol) come on line, mobilizing internal resources, etc. Decision making in high risk situations involves a combination of two of those. Applicant ultimately plans to combine the brain and the physiology data down to the transaction level.

Advantageously, the dimensionality-reduction of PCA can be used to identify sensors that can be removed because the data they collect is determined to be relatively less relevant to the determination of a trader's brain state, and a smaller subset of sensors is adequate to determine brain states relevant to contemplating and executing financial transactions.

As used in the specification, the term "brain" sometimes expediently refers to the entire central nervous system, including both the anatomical brain and the spinal cord. Unless the context dictates otherwise (e.g., by claims that recite both a brain and a spinal cord as if they were distinct entities), the term "brain" should be understood as including the spinal cord.

As used in the specification, a brain "system" "area" or "region" can either refer to an anatomical part of the brain or a functional network or system of the brain, unless the context dictates otherwise. Machine learning may in the future identify novel or different systems and pathways independent of those currently defined by the neuroscientific discipline.

Recapitulation

The methods and systems disclosed in this application have many applications. Accordingly, the invention can be characterized in many different ways and realized in many different embodiments.

A first embodiment is a neurometric-enhanced performance assessment system comprises a neurometric interface, a behavioral task interface, a recorder, a statistical engine, a reporting engine, and a reporting engine. The neurometric interface that collects' neurometric data about a subject while the subject is performing a task and transmits the neurometric data to a computer for recording and analysis. The behavioral task interface collects performance data about a subject while the subject is performing the task. The recorder receives and records the neurometric data from the neurometric interface and performance data from the behavioral task interface. The statistical engine is configured to analyze both the neurometric data and the performance data of the subject and identify correlations between the performance data and the neurometric data. The reporting engine is configured to generate an assessment of the subject's performance and physiological characteristics from the performance data and the neurometric data.

In one implementation, the neurometric interface comprises a plurality of neurophysiological sensors arranged on a base, wherein the base is configured to be worn on the subject's head and to place the neurophysiological sensors in contact with the head.

Also, the base comprises a headband or a virtual reality headset. Furthermore, the neurometric interface further comprises a power supply and a transmitter that transmits neurometric data to the recorder.

In another implementation, the system comprises a synchronizer that synchronizes the neurometric data with the performance data, the synchronizer being communicatively coupled to both the neurometric interface and the behavioral task interface, and the synchronizer ensuring that neurometric signals are coordinated in time with corresponding performance data.

In another implementation, the system further comprises a mapper and a feedback display interface. The mapper maps a representation of the neurometric data onto a 3D-image of the brain. The feedback display interface, which is configured within viewing range of the subject, receives from the mapper map data representative of the 3D-image of the brain and is configured to display the 3D-image of the brain to the subject while the subject is performing the task. The feedback display interface also comprises a video headset worn by the subject.

In another implementation, the system further comprises a task controller that modifies, in real time, the task as a function of the performance data and the neurometric data.

In yet another implementation, the system further comprises a database interface to interface the apparatus to a database that collects physiological state and performance data from a plurality of subjects to identify patterns that statistically correlate performance data and sensed physiological characteristics across the plurality of subjects.

In a further implementation, the system further comprises a neurofeedback interface that provides at least one of the following stimuli or substances to the subject if the system detects that brain activity in a selected brain system has fallen below a threshold: (1) electrical stimulation administered to the subject's head; (2) a neurotropic administered orally or intravenously to the subject; (3) a tactile stimulation administered to the subject's body; (4) a transient sound; and (5) a transient light.

A second embodiment of the invention is method of enhancing performance. The method comprises equipping a subject with one or more neurophysiological sensors of brain activity, selecting tasks for the subject to perform, and for at least one of the tasks, collecting neurometric data about a subject while the subject is performing the task and transmitting the neurometric data to a recorder. The method further comprises collecting performance data about a subject while the subject is performing the task and transmitting the performance data to the recorder, building a database of synchronized neurometric and performance data, and defining an expert performance level for the task. The method also comprises accessing the database to construct brain signatures associated with expert performance; identifying correlations between the performance data and the neurometric data; and generating an assessment of a physiological state of the subject based on the subject's performance and neurometric data.

In one implementation, the method further comprises mapping the neurometric data onto a 3D-image of the brain; and displaying the 3D-image of the brain to the subject while the subject is performing the tasks.

In another implementation, the method further comprises evaluating the neurophysiological data to assess the integrity of specific pathways of the brain. In a further implementation, the method further comprises evaluating the person's default mode network during a period for which person is asked to do nothing. In another implementation, the method further comprises building a predictive model of an individual's possible performance utilizing heuristics derived from time-correlated streams of sensor data and task results.

In another implementation, the method further comprises generating an intervention plan to help the person improve his/her performance on the tasks. The intervention plan can include one or more of the following: an assessment, insights for a coach or trainer, suggestions on diet and neurotropics, brain stimulation, and cognitive stimulation. In yet another implementation, the method further comprises detecting when the person's attention is waning and modifying or interrupting the task to regain the person's focus and engagement.

In another implementation, the method further comprises building and maintaining a database of data for a population of subjects; identifying experts from the population; and identifying brain signatures associated with expert performance across one or more cognitive domains. The signature can include a map that illustrates areas and/or pathways of the brain that are activated by a given task A third embodiment of the invention is a system for enhancing a person's performance. The system comprises a behavioral task interface, a neurometric interface, a mapper, and a display. The behavioral task interface facilitates the person's performance of the task. The neurometric interface collects neurometric data while the person is performing a task. The mapper maps a representation of the neurophysiological data onto a spatial representation of a brain. The display reveals the mapped representation to the person while the person performs the task. The mapped representation assists the person in achieving a targeted brain state while the person is performing the task. In one implementation, the system further comprises a behavioral task interface, such as an exercise machine, simulator or computer exercise that facilitates the person's performance of the task.

A fourth embodiment is a method of enhancing a person's performance. The method comprises equipping a person with one or more neurophysiological sensors of brain activity; the person repeatedly performing a task to enhance the person's performance in a cognitively-related activity; measuring the person's performance on the task while simultaneously collecting neurophysiological data from the sensors; and while the person performs the one or more task, showing the person a visualization of the person's brain activity.

In one implementation, the one or more tasks are performed to prepare for the activity. Also, the one or more tasks and the activity are distinguishable in that they are: performed in simulation and not performed in simulation, respectively; machine-mediated and non-machine mediated, respectively; stationary and mobile, respectively; individual and team-based, respectively; non-competitive and competitive, respectfully, with respect to other persons; and/or indoor and outdoor, respectively.

In another implementation, the task preferentially activates one or more systems of the person's brain in a manner that is greater than and detectably distinguishable from other systems of the person's brain.

In another implementation, the visualization is a 3D representation of a model brain or of the person's brain superimposed with a representation of the person's brain activity, wherein the representation of the person's brain activity is derived from the neurophysiological data. In a fourth embodiment, the method further comprises showing the person an image of a normal, expert, or ideal brain's activity during the performance of the same task. In a further implementation, the method also comprises providing the person a predictive or aspirational 3D representation of the person's brain after the person completes a program of training. In another further implementation, the method also comprises providing the person 3D brain images contrasting an integrity of at least one of the brain's systems before and after performing the tasks over N repetitions, where N is greater than or equal to 1.

A fifth embodiment of the invention is a method of enhancing a person's performance in an activity. The method comprises equipping a person with one or more neurophysiological sensors of brain activity; the person repeatedly performing one or more tasks in preparation for performing an activity, wherein the one or more tasks are different but cognitively-related to the activity, wherein both the tasks and the activity generate detectable electrical activity to an especial extent from a common portion or portions of the brain that are associated with a common cognitive domain; measuring the person's performance on the tasks while simultaneously collecting neurophysiological data from the one or more sensors; and while the person performs the one or more tasks, showing the person a visualization of the person's brain activity.

In one implementation, the method further comprises evaluating the person's default mode network during a period for which person is asked to do nothing and utilizing a representation of the person's brain activity when the default mode network is activated as a baseline against which the person's brain activity while performing the one or more tasks is measured.

In another implementation, the visualization is a 3D image of the person's brain superimposed with a representation of the person's brain activity that changes in real time. In yet another implementation, the visualization includes a comparative 3D image of a normal, ideal, or expert brain's activity during performance of an identical task. In a further implementation, the method comprises providing the person a predictive or aspirational 3D representation of the person's brain after the person completes a program of training. In another further implementation, the method further comprises contrasting a 3D representation of the person's brain activity before the person performs the task or a program of training with a 3D representation of the person's brain activity after the measuring the resulting brain changes and illustrating the resulting brain changes.

A sixth embodiment of the invention is a method of enhancing a person's performance, the method comprising equipping the person with a neurometric monitor; collecting performance data about the person's performance on a baseline task while the person performs the task; and identifying systems of the person's brain that had a sub-optimal level of brain activity while the person performed the task. The method also comprises selecting a set of one or more training tasks that target said identified systems of the brain; collecting neurometric data about the person while the person performs the one or more training tasks; and providing the person with real-time feedback about the person's neurometric data and performance as the person performs the training task.

In one implementation, the method also comprises modifying the task for the person in real-time based on both the person's performance and physiological data/brain signatures. In another implementation, the method also includes producing speech to motivate and exhort the person in real time as the person performs the training task.

The seventh, eighth and ninth embodiments relate to methods of and systems for enhancing team preparation and coaching. The seventh embodiment is a method of enhancing a team's performance by equipping a plurality of team members with sets of one or more sensors, wherein each set includes at least one neurophysiological sensor of brain activity; selecting a set of tasks for each team member to complete which test the team member across a plurality of cognitive domains; and measuring the team members' performances on the tasks while simultaneously collecting neurophysiological data from the sensors. The method further involves, for each team member, synchronizing data from or derived from the sensors with behavioral task performance data and generating an assessment for each team member, the assessment indicating the team member's performances on the tasks and relating the team member's brain activity to those performances.

In one implementation, the method further comprises evaluating whether each team member might be more productive at a different position.

In another implementation, the method further comprises generating an intervention plan for a coach or trainer that provides suggestions on coaching or training adjustments for each team member. The intervention plan includes a program of exercises that preferentially activate selected systems and pathways of the brain and comprises suggestions for a coach or trainer to tailor the coach or trainer's interactions with the team member to improve that member's proficiency within an area of activity. The intervention plan can also include the administration of a neurotropic, oral substance, or intravenous substance.

In yet another implementation, the method further comprises building a predictive model of each team member's potential, wherein the predictive model predicts an improvement goal for each cognitive domain that is a function of both the team member's data and collective data indicating levels of improvement that other persons have achieved.

In a further implementation, the assessment also compares the team member's task performance to baselines for expert performance and/or the team's average performance across said plurality of cognitive domains.

In yet another implementation, at least one of the set of tasks differentially activate one or more parts of the brain. In a further implementation, at least one of the set of tasks is selected to produce a desired brain change in the team member in a targeted performance domain.

In another implementation, at least one of the set of tasks include a set of surveys that measure a team member's resilience to stress. In yet another implementation, the method further comprises evaluating the team member's default mode network during period for which the team member is asked to do nothing.

In another implementation, the set of tasks indicate the integrity of specific parts and/or pathways of the brain. In a further implementation, for at least one of the set of tasks, the visualization is a 3D image of the team member's brain in real time using the sensors. In another implementation, during at least one of the set of tasks, the method includes showing the team member a 3D image of an ideal or expert brain active during the performance of the same tasks. In yet another implementation, the method further comprises providing the team member a graphic of what the team member's brains' 3D images should look like after the training.

In a further implementation, the method further comprises measuring the resulting brain changes and illustrating the resulting brain changes. In another implementation, the method further comprises detecting through evaluation of the team member's brain activity when the team member's attention is waning; and modifying or interrupting the task to remind and/or help the team member to regain focus and engagement.

In yet another implementation, the plurality of cognitive domains includes five or more of the following: processing speed and reaction time, pattern recognition, ability to sustain attention, learning speed, working memory, creativity, autonomic engagement in a task, emotional resilience, burnout, fatigue, and memory.

The eighth embodiment is a method of optimally utilizing a team's players. The method comprises equipping a plurality of players with sets of one or more sensors, wherein each set includes at least one neurophysiological sensor of brain activity and selecting a set of tasks cognitively related to team activities for each player to complete which test the player across a plurality of cognitive domains. A task is cognitively related to a team activity if it preferentially activates a common brain network. The method also comprises measuring the players' performances on the tasks while simultaneously collecting neurophysiological data from the sensors and, for each player, synchronizing data from or derived from the sensors with behavioral task performance data. The method further comprises generating an assessment for each player. The assessment indicates the player's performances on the tasks and explaining the team activities to which the tasks are cognitively related. The method also comprises generating a prediction of each player's capacity to achieve a predefined level of proficiency through practicing, including a predicted amount of time and/or training needed to achieve the predefined level of proficiency; and comparing the predictions generated for each player and identifying team roles on which the player could most contribute to the team.

The ninth embodiment is a method of optimally utilizing a team's players. The method comprises equipping a plurality of players with sets of one or more sensors, including at least one neurophysiological sensor of brain activity, and selecting a set of tasks cognitively related to team activities for each player to complete which test the player across a plurality of cognitive domains. A task is cognitively related to a team activity if it preferentially activates a common brain network. The method also comprises measuring the players' performances on the tasks while simultaneously collecting neurophysiological data from the sensors and, for each player, synchronizing data from or derived from the sensors with behavioral task performance data. The method further comprises generating an assessment for each player, the assessment indicating the player's performances on the tasks and explaining the team activities to which the tasks are cognitively related. The method includes predicting how the team would play if team positions were reassigned amongst the players. The prediction is based on the assessments and utilizes a predictive model. The further includes identifying an assignment of players to team positions that provide the greatest odds of making the team successful. This identification is done on the basis of the predictions, The tenth, eleventh, and twelfth embodiments are directed to construction of an integrity map of the brain's functional systems. The tenth embodiment is a method of constructing a functional system integrity map of a person's brain. The method comprises equipping the person with one or more neurophysiological sensors of brain activity; the person completing a set of tasks that test the person across a plurality of cognitive domains; and measuring the person's performance on the tasks while simultaneously collecting neurophysiological data from the sensors. The method also comprises generating a neurophysiological functional assessment of multiple systems and pathways in the person's brain; and constructing a spatial representation of the person's brain that illustrates the integrity of the brain's functional networks.

In one implementation, the one or more sensors includes EEG sensors distributed about both the right and left hemispheres of the brain. In another implementation, the one or more sensors produce data for determining frequencies associated with brain activity. In a yet another implementation, the method further comprises using data about the person's task performance results to assess the integrity of specific systems and/or pathways of the brain.

In another implementation, the set of tasks include both motor-behavioral and cognitively/neuropsychologically important tasks. In yet another implementation, at least one of the tasks is an experiential task that is performed in a real-world or virtual-reality setting. In a further implementation, at least one of the tasks activate one or more parts of the brain in a manner detectably distinguishable from other parts of the brain.

In one implementation, the plurality of domains includes five or more of the following: processing speed and reaction time, pattern recognition, ability to sustain attention, learning speed, working memory, creativity, autonomic engagement in a task, emotional resilience, burnout, fatigue, and memory.

In one implementation, the method uses a neural network, machine learning, artificial intelligence, PCA, ICA, sparse matrix decompositions, low-rank matrix decompositions, and/or t-Distributed Stochastic Neighbor Embedding (tSNE) to identify patterns of brain activity associated with specific tasks.

In another implementation, the method further comprises presenting a survey to the person and recording survey responses while simultaneously collecting neurophysiological data from the sensors, wherein the act of building a database also incorporates the person's survey results synchronized with the person's survey responses.

The eleventh embodiment is a system for constructing a functional system integrity map of a person's brain. The system comprises a set of neurophysiological sensors of brain activity configured to sense human brain activity; a set of assessment tasks to test the person's cognitive efficiency across a plurality of cognitive domains; and a data collector that stores data about the person's performance on the assessment tasks and neurophysiological data from the sensors. The system also includes a statistical engine that analyzes the performance data and neurophysiological data to identify correlations between the person's performance on the assessment tasks with the person's brain activity while performing the task. The system also includes a database of performance data and neurophysiological data from a population and an evaluation engine that compares the person's performance and brain activity on the assessment tasks with the performance data and neurophysiological data from the population to generate a neurophysiological functional assessment of multiple systems and pathways in the person's brain. Furthermore, the system includes a reporting engine that constructs a spatial representation of the systems and pathways in the person's brain that illustrates the integrity of the brain's functional systems.

In one implementation, the set of neurophysiological sensors comprise EEG sensors arranged to be distributed about both the right and left hemispheres of the brain. In another implementation, the set of neurophysiological sensors produce data for determining frequencies associated with brain activity.

In a further implementation, the data collector is an interface between the sensors and the database that passes sensor signals from the sensors to the database. In another implementation, at least one of the tasks is an experiential task that is performed in a real-world or virtual-reality setting.

In one implementation, the set of tasks are configured to activate one or more parts of a human brain in a manner detectably distinguishable from other parts of the human brain. In a further implementation, the system includes a neural network configured to identify patterns of brain activity associated with specific tasks.

The twelfth embodiment is a method of training one self's brain activity while performing tasks. The method comprises availing oneself of neurometric equipment, including one or more neurophysiological sensors, that is configured to measure one's performance on the tasks while simultaneously collecting neurophysiological data from the sensors, to generate a neurophysiological functional assessment of one self's brain networks, and to construct a spatial representation of one self's brain networks. The method further includes equipping oneself with the one or more neurophysiological sensors and completing a set of tasks that test oneself across a plurality of cognitive domains while the neurometric equipment measures and generates data of one's brain activity and collects and analyzes the brain activity data. The method also includes receiving the spatial representation of one self's brain networks from the neurometric equipment, wherein the spatial representation is derived from the brain activity data.

In one implementation, the method further comprises reviewing real-time imagery (or other derivatives thereof, e.g., a mapping into sounds, tactile stimulation, text, etc.) of one self's brain activity while performing the tasks. In another implementation, the method comprises performing many repetitions of the set of tasks over a period of multiple days to train one self's brain to become more proficient at performing the set of tasks.

The thirteenth through fifteenth embodiments are directed to a system and method for identifying signatures of task-driven brain activity. The thirteenth embodiment is a method of identifying one or more signatures of task-driven brain activity. The method involves equipping each of a population of human subjects with one or more sensors, including at least one neurophysiological sensor of brain activity. Each subject completes a set of tasks that test or quantify the efficiency of at least one of the subject's cognitive domains. The method also involves measuring each subject's task performance while simultaneously collecting brain activity data correlated with the subject's task performance. The method also includes building a database of the task performance and brain activity data from the population of subjects; analyzing the task performance and brain activity data to identify correlations between task performance and brain activity across the population; and constructing one or more signatures of task-driven brain activity, derived from the analysis, wherein the one or more signatures comprise characteristic levels of brain activity in different brain networks for different performance levels.

In one implementation, the machine learning apparatus produces a matrix correlating a plurality of variables, including task performance, with quantitative representations of the brain systems' functional integrities.

In another implementation, each of the one or more signatures are associated with corresponding tasks from the set of tasks. In yet another implementation, each of the one or more signatures is a representation of one or more brain systems and/or pathways between the brain systems that are differentially activated by the task. In a further implementation, each of the one or more signatures quantifies levels of brain activity across a distribution of task performance levels, wherein the levels indicate a range of times and/or accuracy levels with which the task is performed.

In one implementation, the method further comprises inputting the database of task performance and brain activity data into a machine learning apparatus that identifies brain systems and/or pathways between the brain systems that are activated by each of the tasks and that further identifies degrees to which activity in said brain systems and/or pathways are correlated with task performance. The plurality of variables can include survey responses and/or metrics on performance of tasks in which the brain systems and/or pathways between the brain systems are differentially activated with respect to other brain systems and pathways.

In a related implementation, the method comprises inputting data relating to several subjects' performances in practical, real-world activities into the machine learning apparatus. The machine learning apparatus produces a matrix correlating a plurality of variables, including performance in tasks and performance in practical, real-world activities, with brain activity. The machine learning apparatus also generates a prediction heuristic from the correlation matrix for generating a prediction of a person's performance in a selected one of the practical, real-world activities as a function of the person's brain activity and performance of a task.

In another implementation, the method further comprises collecting task performance and brain activity from a subject, wherein the subject is or is not a part of the population of subjects; and comparing the subject's brain activity and task performance with the one or more signatures to construct a neurophysiological functional assessment of multiple functional systems and pathways in the subject's brain. Furthermore, a spatial representation of the systems and pathways in the person's brain is constructed that provides a functional integrity representation of the brain's functional systems.

In one implementation, the plurality of domains includes five or more of the following: processing speed and reaction time, pattern recognition, ability to sustain attention, learning speed, working memory, creativity, autonomic engagement in a task, emotional resilience, burnout, fatigue, and memory. In another implementation, the set of tasks include both motor-behavioral and neuropsychological tasks.

In an economizing implementation, the method further comprises identifying a minimal number of neurophysiological sensors necessary to detect and distinguish different levels of brain activity in different brain networks.

The fourteenth embodiment comprises a system for identifying relationships between physiological characteristics and performance of specific tasks. The system comprises a task-performance monitor that monitors a plurality of persons' performances at one or more tasks; a plurality of physiological sensors that sense one or more physiological characteristics of the plurality of persons while the persons are performing the one or more tasks; and a database that receives data about the one or more physiological characteristics from the plurality of physiological sensors for the plurality of persons and stores the data in a predefined format.

In one implementation, the system further comprises a reporting engine that issues queries to the database and produces graphical and textual reports about a selected person's performance of a task and correlated physiological data. In another implementation, the system further comprises a portal interfaced with the report generating engine, the portal enabling the one or more persons and/or an evaluator to view the selected person's graphical and textual reports. In yet another implementation, the plurality of sensors includes one or more of a fMRI, an EEG, a MEG, a PET, and a fNIR.

The fifteenth embodiment is a system for identifying relationships between physiological characteristics and performance of specific tasks. This system comprises a task-performance monitor that monitors a plurality of persons' performances at one or more tasks; a plurality of neurophysiological sensors that sense brain activity across multiple brain networks of the plurality of persons while the persons are performing the one or more tasks; and a database that receives data about persons' performances along with the persons' brain activity and stores the data in a predefined format. The database stores information about the activity of several brain networks of the persons, such as the dorsal and/or ventral attentional networks. The system also includes a statistical engine comparing brain activity information with performance data to generate models of brain activity associated with the specific tasks.

The sixteenth through eighteenth embodiments are directed to a predictive model of performance based on neurometrics and related methods. The sixteenth embodiment is a method of predicting an individual's performance. The method comprises, in one aspect, accessing a database that includes data about performance and brain activity for a population of subjects that have performed a training program on a first set of tasks, wherein the brain activity data includes chronologies of brain activity of one or more brain networks that are characterized by stronger connections when subjects repeatedly perform the first set of tasks over a period of several days, weeks, or months. In another aspect, the method comprises prompting an individual other than the population of subjects to complete a set of screening tasks while equipped with a set of brain activity sensors and measuring the individual's performance on the set of screening tasks while simultaneously collecting data about the individual's brain activity from the sensors. In yet another aspect, the method comprises predicting an amount of time that the individual will need to train to improve their performance to a predefined level of performance on the basis of the individual's performance on, and brain activity during performance on, the set of screening tasks, in relation to the data about performance and brain activity for the population of subjects.

In one implementation, the first set of tasks include the screening tasks. In another implementation, the method comprises selecting a set of practical tasks for the individual to perform as part of a training regimen, wherein the selection is made as a function of the individual's screening task performance, the individual's brain activity data, and the data about performance and brain activity for the population of subjects. In yet another implementation, the set of practical tasks are distinct from but cognitively related to the set of screening tasks.

In one implementation, the database includes data from the population that performed the training program regarding their completion of the first set of tasks the first time, their completion of a training program, and their completion of the first set of tasks a second time. The method further comprises comparing the population's first-time and second-time performances of the first set of tasks and corresponding brain activity data; and, on the basis of the comparison, predicting how much the individual's performance in the screening task will improve upon completion of a training regimen (demographics, surveys and other individual factors may also be used in the prediction).

The seventeenth embodiment is a method of predicting a person's fitness at performing one or more roles in a team effort. The method comprises prompting the person to complete a set of screening tasks while equipped with a set of brain activity sensors; accessing data that identifies brain networks that are most active in proficient performance of each of several different roles in the team effort; and measuring the person's performances on the set of screening tasks while simultaneously collecting data about activity in the identified brain networks of the person. The method also comprises predicting the person's fitness at performing the one or more roles in the team effort, wherein the prediction is statistically based and a function of the individual's performance, brain activity data, and data identifying brain networks most important in proficient performance of different roles in the team effort.

In one implementation, the method further comprises performing the foregoing steps on a plurality of persons, including said person, that are contributing or available to contributing the team; and predicting a distribution of team roles among the plurality of persons that would make an optimally productive use of the plurality of person's relative talents as identified by their performance and brain activity data.

In another implementation, the method further comprises performing the foregoing steps on candidates, including the person, for the one or more roles on the team; comparing the statistically-based predictions of the candidate's fitness as performing the one or more roles on the team effort; and selecting one of the candidates over another of the candidates to perform the one or more roles on the team on the basis of the comparison.

In yet another implementation, the method further comprises predicting how much and what types of training would be needed by the person to raise their fitness to perform the one or more roles in the team effort to a predefined level, wherein the how-much-training prediction is statistically-based and a function of the individual's performance on, and brain activity during performance on, the set of screening tasks, in relation to the data about performance and brain activity for a previous population of subjects. The prediction can also be a function of the person's predicted emotional commitment to raise their fitness, wherein the emotional-commitment prediction is based on brain activity data of brain networks of the person that are associated with arousal and commitment (demographics, surveys and other individual factors may also be used in the prediction).

The eighteenth embodiment is a method of predicting an individual's performance on the basis of performance result data and brain activity data of a previous population of subjects. The method comprises equipping the population of subjects with at least one neurophysiological sensor of brain activity; challenging each subject to complete a first set of tasks; and measuring each subject's performance on the first set of tasks while simultaneously collecting brain activity data from the sensors. The method further comprises constructing a database of data derived from the brain activity data synchronized with task performance results collected from the population of subjects and identifying patterns between task performance results and brain activity in one or more brain systems and pathways between those systems. The method also comprises challenging an individual to complete diagnostic tasks while equipped with the at least one neurophysiological sensor; measuring the individual's performance on the diagnostic tasks while simultaneously collecting brain activity data from the sensors; and constructing a predictive heuristic model of the individual's probable performance on a training set of tasks, based on the individual's screening task performance, the individual's synchronized brain activity data, and the patterns identified between performance on the first set of tasks and brain activity in the population of subjects.

In one implementation, the diagnostic tasks include at least one of the first set of tasks. In another implementation, the training set of tasks include at least one of the diagnostic tasks. In yet another implementation, the training set of tasks include at least one task that is distinct from all of the diagnostic tasks but cognitively related to at least one of the diagnostic tasks. In a further implementation, the first set of tasks test performance across a plurality of cognitive domains. The plurality of domains can include five or more of the following: processing speed and reaction time, pattern recognition, ability to sustain attention, learning speed, working memory, creativity, autonomic engagement in a task, emotional resilience, burnout, fatigue, and memory.

In another implementation, the one or more sensors includes EEG sensors distributed about both the right and left hemispheres of the brain. In yet another implementation, the method further comprises feeding data from the database into a statistical engine that uses an analysis technique, of which a neural network is a non-limiting example, to identify said patterns. The neural network identifies pathways in the brain, including their speed and an approximation of a number of links or bandwidth in the pathway. In yet another embodiment, the method further provides the individual with an achievement goal which includes an illustration of the individual's potential post-training activity level of various brain systems and pathways between those systems.

The nineteenth through twenty-first embodiments are directed to an attention-monitoring system and method to improve cognitive efficiency. The nineteenth embodiment is a method of helping a person to stay engaged during performance of a task. The method comprises equipping a person with one or more physiological sensors configured to monitor engagement as a function of brain activity in attentional and emotional networks of the person's brain; evaluating physiological data produced by the sensors to quantify and assess an engagement level of the person while performing the task; and modifying the task as a function of the person's engagement level in pursuit of maintaining the person's engagement level above a threshold value.

In one implementation, the method further comprises interrupting the task to prompt the person to regain focus and stay attentive during the rest of the task performance. In another implementation, the method further comprises the direct tracking of engagement per unit time during the task presentation; maintaining a database of low and high engagement epochs in the task for later re-viewing; and replaying the tasks at a speed conducive to higher task engagement. In yet another implementation, the method further comprises assessing the functional integrity of the neuroscience system of the person's brain based upon both the neurophysiological data and data about the performance of the person on the task. In a further implementation, the method further comprises evaluating the person's brain activity during a period for which person is asked to do nothing.

In one implementation, the task selectively activates a brain system in a manner detectably distinguishable from other brain systems. For example, the task can test one or more of the following: processing speed and reaction time, pattern recognition, ability to sustain attention, learning speed, working memory, creativity, autonomic engagement in a task, emotional resilience, burnout, fatigue, and memory.

In another implementation, the method further comprises showing the person a visualization of the person's brain activity while the person performs the task. The visualization can be a 3D image of the person's brain in real time using the sensors. In an enhanced implementation, the method further comprises showing the person a 3D image of an ideal or expert brain active during the performance of the task. In a further implementation, the method comprises providing the person a mockup of what the person's brains' 3D image should look like after completing a program of training. In a yet further implementation, the method also comprises measuring the brain changes resulting from the person's completion of a program of training and illustrating the resulting brain changes.

In another implementation, the method comprises directing a stimulus to the person if the engagement level falls below the threshold. The stimulus can comprise a modification or interruption of a video stream, or an audible, visible, or haptic feedback, or combination thereof, to the person. In yet another implementation, the method also comprises generating an intervention plan that includes one or more of the following: an assessment of the person's brain activity and task performance, a training program involving repetitive performance of a selected set of tasks, insights for a coach or trainer, suggestions on diet and neurotropics, brain stimulation, and cognitive stimulation.

The twentieth embodiment comprises attention-stimulating equipment for helping a person to stay attentive during performance of a task. The equipment comprises one or more neurophysiological sensors, a processor, and a controller. The one or more neurophysiological sensors are configured to monitor and generate data of brain activity of an attentional network of the person's brain (such as the dorsal attentional network or the ventral attentional network) as well as of what is generally characterized as the default network of the person's brain. The processor analyzes the brain activity data of the default network to assess whether the person is performing a cognitive task. The processor analyzes the brain activity data of the attentional network to assess whether the person is paying sufficient attention to performing the task, wherein sufficiency of attention is a function of a degree of brain activity in the attentional network. The controller alerts the person with a sensory stimulus—such as haptic feedback, a light, or a sound—when the assessment indicates that the person is not paying sufficient attention to performing the task.

In one implementation, the processor quantifies the attentiveness of the person while performing the task on the basis of the brain activity of the person's attentional network. When the person's attentiveness falls below a threshold, the processor triggers the sensory stimulus output to the person.

The twenty-first embodiment is attention-stimulating equipment for helping a person to stay attentive during performance of a task. The equipment comprises one or more neurophysiological sensors, a processor, and an electrical or neurotropic controller and connection to the person. The one or more neurophysiological sensors are configured to monitor and generate data of brain activity of an attentional network of the person's brain as well as of what is generally characterized as the default network of the person's brain. The processor analyzes the brain activity data of the brain activity data of the attentional network to assess whether the person is paying sufficient attention to performing the task, wherein sufficiency of attention is a function of a degree of brain activity in the attentional network. The electrical or neurotropic controller and connection to the person provides an electrical or neurotropic stimulus to the person's brain when the person's attention is insufficient.

The twenty-second through twenty-fourth embodiments are directed to a method of and apparatus for revealing functional systems of the brain. The twenty-first embodiment is a method of revealing targeted functional networks of the brain. The method comprises equipping a person with one or more neurophysiological sensors of brain activity; exposing the person to stimulus materials for a targeted functional brain network; collecting neurophysiological signal data about the person's brain activity from the sensors; decomposing and bandpassing the signal data into multiple components across multiple frequency bands, and finding correlations between characteristics of the components. The characteristic, in one implementation, refers to envelopes of the decomposed and bandpassed signal data so that the identified correlations are between the envelopes.

In one implementation, the method further comprises measuring a variability in a number of brain states recorded in the person's brain while the person is exposed to the stimulus materials and comparing the variability in the number of brain states recorded in the person's brain while the person is exposed to the stimulus materials to a variability in a number of brain states recorded in the person's brain while the person's functional brain network is at rest.

In another implementation, the method further comprises generating an assessment for the person that compares the person's brain activity with normative measures of brain activity collected from of a larger population of persons who have performed the set of tasks.

In yet another implementation, the method further comprises generating an intervention plan for the person to improve the person's proficiency within an area of activity that includes exercises that activate selected networks of the person's brain. The intervention plan can include electrical or magnetic brain stimulation or administration of a neurotropic or oral or intravenous supplement. The intervention plan can also include insights for a coach or trainer to tailor his/her coaching or training interactions with the person. The intervention plan can also include a program of training tasks tailored to improve the functional integrity of the brain networks of the person that are activated to perform activities cognitively related to the set of tasks.

In a further implementation, the method includes predicting how long the person will need to practice the training tasks to achieve a predefined level of proficiency with the training tasks. Types of training are also predicted. As the person performs the training tasks, updated predictions are generated of how much longer or what types of training the person will need to practice the training tasks to achieve the predefined level of proficiency.

The twenty-third embodiment is a method of evaluating functional systems of a brain of a professional in comparison with the functional systems of the brains of a professional population of persons, wherein both the professional and the professional population are engaged in a common skilled profession, and wherein both the professional and professional population complete a set of tasks while their brains are being monitored. The method comprises equipping the professional person with one or more neurophysiological sensors of brain activity; challenging the professional to complete the set of tasks, which test the professional across a plurality of cognitive domains; and measuring the professional's performances on the tasks while simultaneously collecting neurophysiological data from the sensors. The method further comprises synchronizing data from or derived from the sensors with behavioral task performance data; comparing task performance and corresponding brain activity metrics of the professional with a population-wide brain activity metric (e.g., a median or average value or a distribution) for other professionals who have performed at an approximately equal level as the professional; and, on the basis of the comparison, generating an assessment that grades the professional's brain networks. As non-limiting examples, the profession can be an athletic sport or a profession such as finance.

In one implementation, the method further comprises generating an intervention plan for the professional to improve the professional's proficiency within the skilled profession, the intervention plan including exercises that preferentially activate selected networks of the professional's brain.

In another implementation, the method further comprises predicting how long the person will need to practice the exercises to achieve a predefined level of proficiency with the training tasks. The method also optionally includes generating updated predictions, as the person performs the training tasks, of how much longer the person will need to practice the training tasks to achieve the predefined level of proficiency.

The twenty-fourth embodiment is a performance tracking apparatus for a subject. The performance tracking apparatus comprises a set of one or more transducers and sensors that track the subject's performance on an activity and generate performance data; a neurometric interface that collects neurometric data about the subject while the subject is performing the activity; and an analytical engine that analyzes both the neurometric data and the performance data of the subject, identifies correlations between the performance data and the neurometric data, and produces a real-time assessment of the subject's performance and that performance's relationship to a physiological state of the subject, wherein the physiological state is determined by the neurometric data.

In one implementation, the performance tracking apparatus has a form of a video headset, including a video display, and the performance tracking apparatus provides an image of a brain superimposed with a representation of the person's brain activity based on the neurometric data. In another implementation, the analytical engine supplies feedback based on the real-time assessment to the video headset. The transducers and sensors can be arranged on an item of apparel.

The twenty-fifth through twenty-eighth embodiments are directed to a closed-loop adaptive training system and method using neurofeedback. The twenty-fifth embodiment is a method of using neurofeedback to attain a specific brain state (such as "flow" or "being in the zone" for a particular task or behavioral skill). The method comprises equipping a subject with one or more neurometric sensors; monitoring and producing neurometric data of brain activity while the subject performs a targeted task or skill; and quantifying and ranking the neurometric data on a scale from a previous population of people performing the targeted task or skill.

In one implementation, the method further comprises defining a targeted attentional and/or neurocognitive state on the basis of the attentional and/or neurocognitive states of the previous population of people; selecting a training task for the person to perform while equipped with the neurometric sensors; analyzing data from the neurometric sensors to determine whether the subject is performing at the targeted attentional and/or neurocognitive state; and adapting the training task to steer the subject toward an enhanced attentional and/or neurocognitive state while performing the targeted task or skill. For example, the training task can be studying film of athletes playing a sport on a playing court or field. The targeted attentional and/or neurocognitive state can also be defined based on previously measured peak attentional and/or neurocognitive states of the training subject.

In various implementations, the adaptation to the training task is to: present an image of the training subject's brain activity in real time as the training subject performs the training task; increase or decrease a difficulty level of sequences of the training task where the training subject's attentional and/or neurocognitive performance is sub-par; and/or interrupt or pause the training task when the training subject's attentional and/or neurocognitive state crosses a threshold.

In another implementation, the adaptation is an interruption in the form of a startling light, sound, or haptic feedback. In yet another implementation, the adaptation of the training task is administration of a neurotropic, brain stimulation, or a cognitively stimulating alternative task. In a further implementation, the adaptation of the training task is selective removal of sequences of the film where watching was performed with sub-par attentional states. Alternatively, this technique is used to prune alphanumeric text streams (e.g., news articles, stock ticker information), audio, and other information (however conveyed).

In one implementation, the adaptation of the training task is re-presentation of sequences of the film that were watched with less than the targeted attentional and/or neurocognitive state. In a further implementation, the adaptation of the training task is re-arrangement of sequences of the film that were watched with less than the targeted attentional and/or neurocognitive state.

In another implementation, the method comprises grading a relative importance of different sequences of the training task with respect to each other and with respect to a role that the training subject performs in a group activity, by identifying particular sequences of the training task that preferentially activate particular brain systems that are also preferentially activated by the training subject's role in the group activity. The adaptation of the training task can be selective removal of sequences in which (a) the training subject's attentional state was inferior to the targeted attentional and/or neurocognitive state and (b) the selectively removed sequences have a relatively low-importance grade.

The twenty-sixth embodiment is a method of adapting a training system using neurofeedback. The method comprises equipping a training subject with one or more neurofeedback sensors that monitor and produce data of brain activity of a plurality of brain networks; producing neurophysiological data that monitors the training subject's brain activity with the neurofeedback sensors while the training subject performs a training task; analyzing the neurofeedback data to detect negative changes in attentional and/or neurocognitive states when the training subject is performing the training task; and responsively adapting the training task to improve the training subject's attentional state while performing the training task.

In one implementation, the adaptation of the training task is to interrupt or pause the training task when the training subject's attentional and/or neurocognitive state crosses a threshold.

In another implementation, the training task is studying film of athletes playing a sport on a playing court or field and the adaptation of the training task is selective removal of sequences of the film where watching was performed with sub-par attentional and/or neurocognitive states.

In yet another implementation, the training task is studying film of athletes playing a sport on a playing court or field, memorizing playbooks or positional sets on a tablet, or recognizing pitches. In the case of film-watching, the adaptation of the training task is representation of sequences of the film that were watched with sub-par attentional and/or neurocognitive states. In the case of memorizing playbooks or positional sets or pitch recognition, this technique is used to prune the information being conveyed (however conveyed).

The twenty-seventh embodiment is a neurometric apparatus for enhancing a subject's performance. The neurometric apparatus comprises a neurometric interface, a behavioral task interface, a statistical engine, and a task controller. The neurometric interface collects neurometric data about the subject while the subject is performing a task and transmits the neurometric data to a computer for recording and analysis. The behavioral task interface prompts the subject to perform one or more tasks and collect performance data about a subject while the subject is performing the task. The statistical engine analyzes both the neurometric data and the performance data of the subject, identifies correlations between the performance data and the neurometric data, and produces a real-time assessment of the subject's performance and that performance's relationship to a physiological state of the subject, wherein the physiological state is determined by the neurometric data. The task controller adaptively modifies aspects of the task in response to the real-time assessment.

In one implementation, the neurometric apparatus further comprises a decision engine that identifies changes in a running average of neurophysiological data that exceed a predetermined threshold, wherein the task controller responsively modifies the task that subject is performing.

The twenty-eighth embodiment is a system to enhance a person's performance. The system comprises a neurometric interface and a controller. The neurometric interface collects neurometric data about a subject while the subject is performing a task and transmits the neurometric and behavioral data to a computer for recording and analysis processing. The controller modifies the task as a function of the processed neurometric data to improve the neurometric model for enhanced task performance.

The twenty-ninth through thirty-third embodiments are directed to a neurocognitive testbed and related method. The twenty-ninth embodiment is a method of constructing a cognitive training program to attain a targeted cognitive state under both relaxed and stressful conditions. The method comprises exposing the person to neurocognitive stimulus materials including a task both when the person is experiencing a relaxed condition and when the person is experiencing a stressful condition; monitoring the person's brain activity while the person is exposed to the neurocognitive stimulus materials; and evaluating whether or to what extent the person's brain activity exhibits the targeted cognitive state.

In one implementation, the method further comprises selecting a set of cognitive training tasks to improve brain activity in a brain network associated with the targeted cognitive state under the relaxed and stressful conditions; and incorporating the set of cognitive training tasks into a cognitive training program. In a more detailed implementation, the method also comprises operating the cognitive training program by tracking one or more physiological metrics of the person while the person performs the set of cognitive training tasks and adapting one or more of the cognitive training tasks in the set of cognitive training tasks as the person's performance improves. In an alternative more detailed implementation, the method further comprises operating the cognitive training program by ending the cognitive training program when the person's performance or rate of performance improvement under baseline conditions exceeds a first threshold and the person's performance or rate of performance improvement under stress exceeds a second threshold. In a second alternative more detailed implementation, the method further comprises operating the cognitive training program by ending the cognitive training program when the physiological data indicates that a level of connectivity detected within the brain network exceeds a targeted threshold. In a third alternative more detailed implementation, the method further comprises providing real-time visual feedback to the person regarding the person's brain activity while the person performs the cognitive training tasks.

In various implementations, the cognitive state is one or more of the following: worker engagement, creativity, teamwork, emotional regulation, emotional valence, engagement, perception, attention, memory encoding and retrieval, narrative comprehension, positive emotions, relaxation, arousal, empathy, workload, visual imagery, and kinesthetic imagery.

In one implementation, the set of selected cognitive training tasks includes a plurality of the following: a biological motion perception test that assesses a capacity of a person's visual systems to recognize complex patterns that are presented as a pattern of moving dots; a visual perceptual task; and a 3D multiple-object-tracking speed threshold task that presents a number of moving targets with among distractors in a large visual field, thereby enabling neurometric identification of mental abilities including attention and memory skills when a person processes the scenes.

In another implementation, the method also comprises monitoring one or more of the following: heart rate variability, affective state classifier, midline theta, heart rate, mu suppression, prefrontal gamma, workload classification, left occipital alpha slow suppression, right occipital alpha slow suppression, left parietal alpha slow suppression, and right parietal alpha slow suppression.

The thirtieth embodiment is a method of evaluating a speed of an individual's brain in acquiring new information. The method comprises exposing the individual to stimulus materials that include new information, monitoring the subject's physiological responses while exposing the individual to the stimulus materials, collecting data from the physiological recording devices, and analyzing the data.

A thirty-first embodiment is a method of constructing an assessment system to predict an individual or team's performance under pressure. The method comprises selecting a set of behavioral tasks that differ in processing requirements, differ in decision-making requirements, and differ in perceived stress. The method further comprises exposing the individual or team to the selected set of behavioral tasks while monitoring the individual's or team's physiological responses and predicting an individual or team performance under pressure as a function of the individual's or team's physiological responses.

In one implementation, the method further comprises directly measuring brain activity in emotional and executive neural networks of the individual's brain or the team's brains, wherein the prediction is a function of said direct measurements.

A thirty-second embodiment is a method of constructing a cognitive training program for a person. The method comprises targeting a brain network for assessment and training, selecting a set of assessment tasks to assess the performance of the person's targeted brain network, and preparing the person to perform the set of assessment tasks under a baseline condition. The method also comprises, tracking one or more physiological metrics, while the person performs the set of assessment tasks under the baseline condition, that reveal an extent of a person's brain activity in the targeted network. The method further comprises preparing the person to perform the set of assessment tasks under a stressful conditions, and while the person performs the set of assessment tasks under the stressful condition, tracking one or more physiological metrics that reveal whether or to what extent the person's brain activity exhibits the targeted cognitive state. The method additionally comprises using physiological data generated by the tracking, assessing the connectivity of a brain network of the person that is associated with the targeted cognitive state and selecting a set of cognitive training tasks to improve connectivity of the person's brain network under baseline conditions and while being stressed, wherein the cognitive training program comprises the set of cognitive training tasks.

In various implementation, the step of preparing the person comprises providing the person with equipment that directs the tasks, providing the person with physiological sensors to wear while performing the tasks, and motivating the person with exhortation or motivational information. In various implementations, the equipment is at least one exercise machine and/or a computer with a program running on it that directs the assessment tasks.

A thirty-third embodiment is a method of improving workplace productivity. The method comprises targeting one or more brain networks for assessment and training of attentiveness, memory, worker engagement, creativity, and/or teamwork; selecting a set of assessment tasks to assess a quality of the targeted brain networks; and selecting workers to perform the set of assessment tasks. The method further comprises tracking, for each worker and while each worker performs the set of assessment tasks, one or more physiological metrics that reveal brain activity and connectivity in brain networks associated with attentiveness, memory, worker engagement, creativity and/or teamwork. The method additionally comprises selecting, for each worker, a set of cognitive training tasks to improve connectivity of the worker's targeted brain networks associated with attentiveness, memory, worker engagement, creativity and/or teamwork. The method also comprises incorporating, for each worker, the set of cognitive training tasks into a cognitive training program customized for that worker and providing equipment for each worker to perform the cognitive training program.

In one implementation, the method further comprises operating the cognitive training program by tracking, for each worker, one or more physiological metrics as the worker performs the set of cognitive training tasks and adapting, for each worker, one or more of the cognitive training tasks or the set of cognitive training tasks as the worker's performance improves.

In another implementation, the method further comprises operating each worker's cognitive training program by ending the cognitive training program when physiological data indicates that a level of connectivity detected within the worker's targeted one or more brain networks exceeds corresponding targeted thresholds for the brain networks.

In yet another implementation, the set of selected cognitive training tasks includes a biological motion perception test, a visual perceptual task, and a 3D multiple-object tracking threshold task. The biological motion perception test assesses a capacity of a person's visual systems to recognize complex patterns that are presented as a pattern of moving dots. The 3D multiple-object-tracking speed threshold task presents a number of moving targets with among distractors in a large visual field, thereby enabling neurometric identification of mental abilities including attention and memory skills when a person processes the scenes.

The thirty-fourth through the thirty-sixth embodiments are directed to increasing cognitive performance and brain health in company employees and executives. The thirty-fourth embodiment is a method of improving cognitive efficiency in company employees. The method comprises equipping the company employees with a plurality of neurocognitive sensors that measure electrical activity in the brain; administering a pre-training assessment comprising a plurality of assessment tasks to the company employees while the neurocognitive sensors collect data about electrical activity in the company employees' brains; and selecting training tasks for each of the employees to complete. The method also includes, after the employees complete their training tasks, again equipping the company employees with the plurality of neurocognitive sensors and administering a post-training assessment to the company employees after they complete the selected training tasks. Meanwhile, the neurocognitive sensors collect data about electrical activity in the company employees' brains. The post-training assessment comprises the plurality of assessment tasks administered during the pre-training assessment. After each administering step, the collected data is processed through a data conditioning pipeline to generate spatial maps of cognitive workload across the brain. A report is also generated that contrasts the cognitive workload maps generated from the pre-training assessment with the cognitive workload maps generated from the post-training assessment.

In one implementation, during both the pre-training and post-training assessments, the employees are directed to assume an inactive at-rest state. The neurocognitive sensors collect data about the electrical activity while the employees are in the inactive, at-rest state. In another implementation, the data-processing pipeline computes bandpower ratios between active states during which the employees executed assessment tasks and at-rest states.

In yet another implementation, the data conditioning pipeline comprises a preprocessing stage that filters anomalies from the data. The preprocessing stage can include low and high pass filtering to remove eye and muscle motion artifacts. The preprocessing stage can also remove bad channels and bad time windows.

In one implementation, the data conditioning pipeline comprises a pattern-identifying stage that analyzes the data to find patterns of brain activity. For example, the pattern-identifying stage can comprise a power spectral density estimation performed on the data to compute the employees' brain bandpower during tasks.

In another implementation, the data is decomposed into alpha, beta, theta, and delta frequency bands. Also, in one example, the ratio between beta and the sum of theta and alpha is used as a proxy for workload. In another example, a ratio between higher theta and beta is used as a proxy for memory engagement. In yet another example, a ratio between lower theta and beta is used as a proxy for attention.

In another implementation, the company employees are surveyed to self-assess their efficiency in performing employee-related tasks during both the pre-training assessment and post-training assessment. The report that is generated also contrasts the employees' self-assessments.

In a further implementation, the plurality of tasks assessment includes one or more work-related tasks that the employees routinely perform for the company in their employee occupation. For example, the work-related tasks can include at least one of the following: typing, data entry, filing, researching, performing a calculation, creating a summary, preparing a letter, assisting a customer, and resolving a technical problem.

The thirty-fifth embodiment is a method of improving cognitive efficiency in company employees. The method comprises equipping the company employees with a plurality of neurocognitive sensors that measure electrical activity in the brain; administering a pre-training assessment comprising a plurality of assessment tasks to the company employees while the neurocognitive sensors collect data about electrical activity in the company employees' brains; and selecting training tasks for each of the employees to complete. After the employees complete their training tasks, they are again equipped with the plurality of neurocognitive sensors so that they can be administered a post-training assessment. As the employees complete the post-training assessment, which includes the same plurality of assessment tasks administered during the pre-training assessment, the neurocognitive sensors collect data about electrical activity in the company employees' brains. After each administering step, processing the collected data through a data conditioning pipeline to generate spatial maps of cognitive workload across the brain. The data conditioning pipeline comprises a preprocessing step to filter the data and a pattern-identifying step that identifies brain states or signatures in the filtered data.

In one implementation, the pattern-identifying stage comprises a power spectral density estimation performed on the data to compute the employees' brain bandpower during tasks. In another implementation, the pattern-identifying step comprises decomposing the filtered data into frequency bands, for example, the alpha, beta, theta, and delta frequency bands. In a further implementation, the method comprises: using a ratio between beta and the sum of theta and alpha as a proxy for workload; using a ratio between higher theta and beta as a proxy for memory engagement; and/or using a ratio between lower theta and beta as a proxy for attention.

The thirty-sixth embodiment is a system for improving cognitive efficiency in company employees. The system comprises a data processor; a plurality of neurocognitive sensors, an assessment program, a program of training tasks, a data processing pipeline, and a reporting program. The plurality of neurocognitive sensors are configured to be applied to the company employees to measure electrical activity in their brains and to be communicatively coupled with the data processor. The assessment program is stored on a computer medium and configured for computer execution to visually, audibly and/or tactilely present a plurality of assessment tasks to the company employees and receive responses from the company employees while the neurocognitive sensors collect data about electrical activity in the company employees' brains. The program of training tasks stored on a computer medium and configured for computer execution to provide audibly, visually, and/or tactilely stimulation to employees to direct and aid their performance of the training tasks. The data processing pipeline processes the collected data to generate spatial maps of cognitive workload across the brain. The reporting program stored on a computer medium contrasts the cognitive workload maps generated from the pre-training assessment with the cognitive workload maps generated from the post-training assessment. As used herein, "program" can be a routine or subroutine of a larger program.

The thirty-seventh through the forty-third embodiments are directed to a neurological and biological feedback method and system of analysis, training and management of high-risk operations. The thirty-seventh embodiment is a method of tracking, training and/or management of a real or prospective investor's or trader's brain states while trading real or simulated securities. The method comprises collecting electroencephalography (EEG) data from the investor or trader as they engage in buy, sell, market and/or limit order transactions involving real or simulated financial instruments, including but not limited to securities, funds, and currencies; collecting transactional data regarding the buy, sell, market and/or limit order transactions; and grading the transactional data to generate an assessment of the investor or trader's trading performance over time. The method also comprises processing the EEG and transactional data to identify patterns between the investor or trader's brain states and trading performance, including any correlations between brain states and superior performance and between brain states and inferior performance.

In one implementation, after the correlations are found, the method further comprises continuing to collect EEG data from the investor or trader and generating an alert in real time when the prospective investor's or trader's brain state exhibits a brain state associated with either inferior performance, superior performance, or both.

In another implementation, the method further comprises collecting real or simulated market data regarding the securities and synchronizing over a time window the EEG and transactional data. The market data includes a measure of, or data supporting a measure of, the alpha of the transaction, which can be measured in relation to the volume-weighted average price data. The market data can also include a measure of profitability of the transactions, market conditions at the time the transactions were made, and trading volumes.

In another implementation, the method further comprises generating a summary of the investor's or trader's trading performance that also indicates any correlations between detected brain states of the investor or trader and their trading performance. The trading performance can, for example, be determined as a function of volume-weighted average price data. The method can also comprise providing the summary to a risk manager to help the risk manager (or other decision maker) assess whether to allow or reject a trade or to engage in an intervention with the investor or trader to help motivate them into a brain state more optimal for trading.

In one implementation, the method comprises preprocessing the EEG data to remove artifactual data such as eye blink and motion artifacts and slow-drift and 60 Hz artifacts. In another implementation, the step of processing the EEG data includes performing functional connectivity state estimation on the EEG data to identify brain states that are indicative of functional connectivity in particular areas of the brain. The step of processing the data can include principal component analysis (PCA) or max-kurtosis independent components analysis (ICA) of the EEG data.

In another implementation, the method comprises equipping the investor or trader with an EEG headset or cap that collects data over a sufficient number of channels to track brain states that are represented in both space and frequency spectra. In a further implementation, the method comprises collecting physiological data other than brain states as they engage in buy, sell, market and/or limit order transactions involving real or simulated securities. For example, in various implementations, the physiological data includes heart rate, pupillometry with eye tracking, data received from galvanic skin sensors.

In another implementation, the method further comprises collecting media information that comprises information presented to the trader or investor before the investor or trader submitted their subtractions. This can include categorizing the media information by type and analyzing which, if any, types of media information engender superior performance and which, if any, types of media information engender inferior performance. It can also include analyzing which, if any, types of media information engender a brain state associated with superior performance and which, if any, types of media information engender a brain state associated with inferior performance.

In yet another implementation, the method further comprises categorizing the media information by type and analyzing which, if any, types of media information engender a brain state associated with overstimulation in the trader or investor and which, if any, types of media information engender a brain state associated with under-stimulation of the trader or investor.

The thirty-eighth embodiment is a method of training and/or management of a real or prospective investor's or trader's physiological states while trading real or simulated securities. The method comprises collecting physiological data from the investor or trader as they engage in buy, sell, market and/or limit order transactions involving real or simulated securities; collecting transactional data regarding the buy, sell, market and/or limit order transactions; and grading the transactional data to generate an assessment of the investor or trader's trading performance over time. The method also comprises processing the physiological and transactional data to identify patterns between the investor or trader's physiological states and trading performance, including any correlations between physiological states and superior performance and between physiological states and inferior performance. In one implementation, the physiological data is electrocardiogram (ECG/EKG) data The thirty-ninth embodiment is a security trading apparatus comprising an electroencephalography (EEG) headset or cap, a computer or computers, and a transducer. The electroencephalography (EEG) headset or cap collects EEG data from an investor or trader as they engage in buy, sell, market and/or limit order transactions involving real or simulated securities. The computer or computers are configured to collect transactional data regarding the buy, sell, market and/or limit order transactions, grade the transactional data to generate an assessment of the investor or trader's trading performance over time, and process the EEG and transactional data to identify patterns between the investor or trader's brain states and trading performance, including any correlations between brain states and superior performance and between brain states (or physiological states) and inferior performance. The transducer is configured to generate real-time alerts, after patterns have been identified, when subsequently collected EEG data from the investor or trader indicates that their brain state (or physiological state) is associated with either inferior performance, superior performance, or both.

The fortieth embodiment is a security trading apparatus comprising a monitor (i.e., a physiological data-collecting accoutrement) that collects physiological data from an investor or trader as they engage in buy, sell, market and/or limit order transactions involving real or simulated securities, a computer or computers, and a transducer. The computer or computers are configured to collect transactional data regarding the buy, sell, market and/or limit order transactions, grade the transactional data to generate an assessment of the investor or trader's trading performance over time, and process the physiological and transactional data to identify patterns between the investor or trader's physiological states and trading performance, including any correlations between physiological states and superior performance and between physiological states and inferior performance. The transducer is configured to generate real-time alerts, after patterns have been identified, when subsequently collected physiological data from the investor or trader indicates that their physiological state is associated with either inferior performance, superior performance, or both.

The forty-first embodiment is a security trading apparatus comprising a neurometric interface or physiological data-collecting accoutrement, a data analysis program, and a transaction gatekeeper. The neurometric interface or physiological data-collecting accoutrement collects neurological functional activity data about a human transaction-maker as the transaction-maker takes actions or abstains from taking actions to implement transactions involving real or simulated financial instruments. The data analysis program processes the collected neurological functional activity data to identify one or more brain states of the transaction-maker and automatically generates, in near real-time, information about the transaction-maker's contemporaneous brain states (measured in terms of functional connectivity of the transaction-maker's brain) when the transaction-maker performs or abstains from performing actions to implement said transactions. The transaction gatekeeper comprises at least one of the following: (a) a program or a circuit that conditionally enables transactions to proceed on the basis of the transaction-maker's contemporaneous brain state; and (b) an annunciator configured to convey the information to a human authorized to stop the transaction from proceeding or authorized to manage the transaction-maker.

In one implementation, the annunciator is a user-customizable dashboard panel on a digital display. The security trading apparatus further comprises a user-interface that enables a person to select one or more items of informative stimuli to incorporate into a panel area of the digital display, which is configured to provide near real-time feedback. The near real-time feedback allows for delays of a period of no more than a few seconds in obtaining and computer-analyzing the data. The feedback is viewable by the transaction-maker while the transaction-maker is contemplating said transactions.

In another implementation, the security trading apparatus further comprises an optical display device in a form of a headset, goggles, or other human-wearable or human-mountable optical display platform. The security trading apparatus further comprises a processor programmed to perform principal component analysis (PCA), independent component analysis (ICA), sparse matrix decompositions, low-rank matrix decompositions, and/or t-Distributed Stochastic Neighbor Embedding (tSNE) on the neurological functional activity data to identify the transaction-maker's brain states.

In further implementations, the human who is authorized to stop the transaction is the transaction-maker, fund manager, or portfolio manager.

The forty-second embodiment is a method of predicting whether a person is in a physiological state that is conducive to making or performing high-quality or highly accurate decisions or actions. The method comprises equipping the person with one or more physiological sensors; collecting sensor data from the one or more physiological sensors during time windows preceding the person making a plurality of decisions and/or performing a plurality of actions; measuring the quality or accuracy of the decisions or actions; identifying correlations between the sensor data or derivatives of the physiological data and the quality or accuracy of the decisions or actions; and using subsequent collections of sensor data and the identified correlations to predict whether the person is likely to make a high-quality or highly accurate decision or action in response to an opportunity to decide or act.

In one implementation, the method further comprises presenting the prediction to the person before the person decides or acts. In another implementation, the method further comprises processing the sensor data to identify a physiological state that is correlated with above-average decisions or actions. In yet another implementation, the processing of the physiological data includes a set of procedures for preprocessing the sensor data. In a further implementation, the set of procedures for preprocessing the data includes filtering the data.

In one implementation, the set of procedures for preprocessing the data includes standardizing the data. In another implementation, the set of procedures for preprocessing the data includes a robust principal component analysis (PCA) of the data. In yet another implementation, the set of procedures for preprocessing the data includes identifying and rejecting bad channels. In a further implementation, the set of procedures for preprocessing the data includes identifying and rejecting bad sample in the data.

In a more detailed implementation, the processing of the physiological data includes performing a functional connection state estimation (FCSE) on the data. In another implementation, the FCSE of the data comprises transforming the physiological data into principal component channels of data. In a further implementation, the FCSE of the data comprises bandpass filtering the principal component channels of data into discrete frequency bands. In yet another implementation, the FCSE of the data further comprises usage of a Hilbert transformation of the principal component channels for each discrete frequency band to identify envelopes enclosing data signals of each of the principal component and frequency band channels. The statistical engine is configured to decompose and bandpass sensor data into components that extend across frequency bands and identify a first set of correlations between characteristics of the decomposed and bandpassed data in order to identify a first set of physiological states. The statistical engine is also configured to measure and quantify the person's performance with respect to the tasks and identify correlations between the first set of physiological states and the person's performance on the first set of tasks. Moreover, the statistical engine is configured to identify a second set of correlations between the sensor data or derivatives of the sensor data and the person's performance on the first set of tasks. The statistical engine, now trained with the person's physiological and performance data, later receives a new set of sensor data from the one or more physiological sensors, again during time windows preceding the person measuring the person's performance on a set of decisions or actions to take. As before, the statistical engine decomposes and bandpasses the new set of sensor data, identifies a current physiological state from the new set of sensor data, compares the current physiological state with the first set of physiological states, and, based on that comparison, generates an expected value of the person's performance on the second set of decisions or actions, before the person makes or performs the second set of decisions or actions.

In one implementation, the method further comprises computing correlation matrices between the envelopes using a sliding time window in order to identify co-modulations between the frequency bands along each principal component. In another implementation, the method further comprises clustering data of the correlation matrices using k-means.

The forty-third embodiment is an apparatus for predicting whether a person is in a physiological state that is conducive to making or performing high-quality or highly accurate decisions or actions. The apparatus comprises one or more physiological sensors, analog-to-digital converters, memory, electrical connectors, behavioral interface, and feed of comparative data. The one or more physiological sensors transduce signals received from the head or body of the person. The one or more analog to digital converters convert analog signals from the physiological sensors into digital signals. The memory stores the digital signals as sensor data. The behavioral interface facilitates the person's performance of one or more tasks and also quantifies the task results. The feed of comparative data might comprise a feed of stock market data A first processor under the direction of a data collection routine collects sensor data from the one or more physiological sensors during time windows preceding the person making a plurality of decisions and/or performing a plurality of actions. A performance analyzer measures the quality or accuracy of the decisions or actions. The first or a second processor under the direction of a correlation-determining routine identifies correlations between the sensor data or derivatives of the physiological data and the quality or accuracy of the decisions or actions. The first, second, or a third processor under the direction of a predictive routine uses subsequent collections of sensor data and the identified correlations to predict whether the person is likely to make a high-quality or highly accurate decision or action in response to an opportunity to decide or act.

The forty-fourth through forty-fifth embodiments are directed to a system and method for identifying physiological states that predict a person's performance and characterizing a person's performance as a function of physiological state. The forty-fourth embodiment is a system that comprises a physiological interface, a behavioral interface, and a data processing pipeline. The physiological interface includes one or more physiological sensors attached to the person that generate physiological data about the person while performing a task or real-world activity. The behavioral interface generates performance data about the person while the person is performing the task or real-world activity. The data processing pipeline collects the physiological data from the physiological interface, the performance data from the behavioral interface, and reference data from a population of people performing the same or similar tasks or real-world activities. The data processing pipeline also identifies characteristic physiological states derived from the physiological data, grades the performance data, compares the graded performance data to the characteristic physiological states, and identifies statistical relationships between the characteristic physiological states and levels of performance.

In one implementation, the physiological data is neurophysiological data. Furthermore, in various implementations, the characteristic physiological states are distributions of workload across the brain and/or brain states. In another implementation, the data processing pipeline identifies characteristic physiological states by decomposing the physiological data by preprocessing and transforming the physiological data to identify components associated with variances in or sources of the physiological data, bandpassing the components across several frequency bands, finding correlations between envelopes of the bandpassed components, and clustering the correlation data. In another implementation, the person is an equity trader, the grade is of the person's performance in making security executions, and the reference data is market data about the executed securities. In yet another implementation, the reference data is the volume weighted average price (VWAP) of the securities in a window of time around when the executions were made. In a further implementation, the method further comprises a database configured to store the reference data and to update the reference data with the person's physiological data and performance data.

In one implementation, the statistical engine uses two principal components analyses (PCAs), one to preprocess the physiological data and the other to transform the physiological data into frequency bandsourced components. In another implementation, the reference data includes information about characteristic levels of progress as a function of training and the statistical engine is configured to use an assessment of the person and the reference data to predict an amount of training needed to raise the person's level of performance to a goal. In a further implementation, the system includes a monitor that displays neuroimaging feedback to the person illustrating activation of brain regions and/or pathways as the person performs the task or real-world activity.

The forty-fifth embodiment is a method for identifying physiological states that predict a person's performance. The method comprises using a physiological interface that includes one or more physiological sensors attached to the person to generate physiological data about the person while performing a task or real-world activity, using a behavioral interface to generate performance data about the person while the person is performing the task or real-world activity, and collecting the physiological data from the physiological interface, the performance data from the behavioral interface, and comparative data from a population of people performing the same or similar tasks or real-world activities. The method also comprises identifying characteristic physiological states from the decomposed data, grading the performance data, comparing the graded performance data to the characteristic physiological states, and identifying statistical relationships between the characteristic physiological states and levels of performance.

In one implementation, the physiological data is neurophysiological data. Furthermore, in various implementations, the characteristic physiological states are distributions of workload across the brain and/or brain states. In another implementation, the data processing pipeline identifies characteristic physiological states, which includes: decomposing the data by preprocessing and transforming the physiological data to identify components associated with variances in or sources of the physiological data; bandpassing the components across several frequency bands; finding correlations between envelopes of the bandpassed components; and clustering the correlation data. In another implementation, the person is a trader, the grade is of the person's performance in making security executions, and the reference data is market data about the executed securities. In a further implementation, the statistical engine uses two principal components analyses (PCAs), one to preprocess the physiological data and the other to transform the physiological data into frequency bandsourced components.

In one implementation, the method further comprises storing the reference data in a database and updating the reference data with the person's physiological data and performance data. The reference data includes information about characteristic levels of progress as a function of training and the statistical engine is configured to use an assessment of the person and the reference data to predict an amount of training needed to raise the person's level of performance to a goal.

In another implementation, the method further comprises displaying neuroimaging feedback to the person illustrating activation of brain regions and/or pathways as the person performs the task or real-world activity. In a further implementation, the method comprises selecting a set of brain training tasks for the person to perform as a function of the person's performance on a plurality of assessment tasks.

It will be understood that many modifications could be made to the embodiments disclosed herein without departing from the spirit of the invention. For example, FIG. 21 could be modified to utilize neurometric sensors only when the person is performing an assessment (i.e., not when performing cognitive training).

As used in this specification, "engine" refers to a program or system of programs comprising code stored on a non-transitory medium, computer, or processor that, when executed, performs the recited functions.

Having thus described exemplary embodiments of the present invention, it should be noted that the disclosures contained in the drawings are exemplary only, and that various other alternatives, adaptations, and modifications can be made within the scope of the present invention. Accordingly, the present invention is not limited to the specific embodiments illustrated herein but is limited only by the following claims.

We claim:

1. A method of predicting whether a person is in a physiological state that is conducive to making or performing high-quality or highly accurate decisions and/or actions, the method comprising:
   equipping the person with one or more physiological sensors;
   generating sensor data through the one or more physiological sensors during time windows preceding and including the person making or performing a first set of decisions and/or actions;

decomposing and bandpassing the sensor data into components that extend across frequency bands;
identifying a first set of correlations between characteristics of the decomposed and bandpassed data in order to identify a first set of physiological states;
measuring and quantifying the person's performance with respect to the first set of decisions and/or actions;
identifying correlations between the first set of physiological states and the person's performance on the first set of decisions and/or actions;
identifying a second set of correlations between the sensor data or derivatives of the sensor data and performance on the first set of decisions and/or actions;
collecting a new set of sensor data from the one or more physiological sensors during time windows preceding the person measuring the person's performance on a second set of decisions and/or actions;
decomposing and bandpassing the new set of sensor data;
identifying a current physiological state from the new set of sensor data;
comparing the current physiological state with the first set of physiological states; and
based on that comparison, generating an expected value of the person's performance on the second set of decisions and/or actions, before the person makes or performs the second set of decisions and/or actions.

2. The method of claim 1, further comprising presenting the expected value to the person before the person makes or performs the second set of decisions and/or actions and providing the person an opportunity to refrain from action.

3. The method of claim 1, further comprising processing the sensor data to identify a physiological state that is correlated with above-average performance.

4. The method of claim 3, wherein the processing of the sensor data includes:
filtering the data;
standardizing the data; and
performing a robust principal component analysis (PCA) of the data.

5. The method of claim 4, wherein the performing the robust PCA of the data includes:
performing PCA to preprocess the sensor data; and
performing PCA to transform the sensor data into components.

6. The method of claim 3, wherein the processing of the sensor data includes performing a functional connection state estimation (FCSE) on the sensor data, including:
transforming the sensor data into principal component channels of data;
bandpass filtering the principal component channels of data into discrete frequency bands;
identifying envelopes enclosing data signals of each of the principal component and frequency band channels;
computing correlation matrices between the envelopes using a sliding time window in order to identify co-modulations between the frequency bands along each principal component; and
clustering data of the correlation matrices.

7. The method of claim 1, wherein identifying the first set of correlations between characteristics of the decomposed and bandpassed data in order to identify the first set of physiological states includes:
finding correlations between envelopes of the bandpassed components; and
clustering the correlations.

8. The method of claim 1, wherein the first set of physiological states includes brain states.

9. The method of claim 1, wherein the sensor data is indicative of neurophysiological data.

10. The method of claim 1, wherein the first set of actions includes the person making a security execution.

11. A system comprising:
a physiological interface including one or more physiological sensors that are configured to be attached to a person, wherein the one or more physiological sensors are configured to:
generate a first set of sensor data during time windows preceding and including the person making or performing a first set of decisions and/or actions, and
generate a second set of sensor data during time windows preceding the person measuring the person's performance on a second set of decisions and/or actions; and
a data processing pipeline configured to:
decompose and bandpass the first set of sensor data into components that extend across frequency bands,
identify a first set of correlations between characteristics of the decomposed and bandpassed data in order to identify a first set of physiological states,
measure and quantify the person's performance with respect to the first set of decisions and/or actions,
identify correlations between the first set of physiological states and the person's performance on the first set of decisions and/or actions,
identify a second set of correlations between the first set of sensor data or derivatives of the first set of sensor data and performance on the first set of decisions and/or actions,
decompose and bandpass the second set of sensor data,
identify a second physiological state from the second set of sensor data,
compare the second physiological state with the first set of physiological states, and
based on the comparison, generate an expected value of the person's performance on the second set of decisions and/or actions, before the person makes or performs the second set of decisions and/or actions.

12. The system of claim 11, wherein the data processing pipeline is configured to process the first set of sensor data to identify a physiological state that is correlated with above-average performance.

13. The system of claim 11, wherein the data processing pipeline is configured to:
filter the first set of sensor data;
standardize the first set of sensor data; and
perform a robust principal component analysis (PCA) of the first set of sensor data.

14. The system of claim 11, wherein the data processing pipeline is configured to perform a functional connection state estimation (FSCE) on the first set of sensor data.

15. The system of claim 11, wherein the data processing pipeline is configured to:
transform the first set of sensor data into principal component channels of data;
bandpass filter the principal component channels of data into discrete frequency bands;
identify envelopes enclosing data signals of each of the principal component and frequency band channels;
compute correlation matrices between the envelopes using a sliding time window in order to identify co-modulations between the frequency bands along each principal component; and
cluster data of the correlation matrices.

16. The system of claim 11, wherein the data processing pipeline is configured to:
- perform principal component analysis (PCA) to preprocess the first set of sensor data; and
- perform PCA to transfer the first set of sensor data into components.

17. The system of claim 11, wherein the data processing pipeline is configured to identify the first set of correlations between the decomposed and bandpassed data in order to identify the first set of physiological states by:
- finding correlations between envelopes of the bandpassed components; and
- clustering the correlations.

18. The system of claim 11, further comprising a monitor configured to display neuroimaging feedback, the neuroimaging feedback illustrating activation of brain regions and/or pathways as the person performs the first set of decisions and/or actions.

19. The system of claim 11, wherein the first set of sensor data is indicative of neurophysiological data.

20. The system of claim 11, wherein the first set of actions includes the person making a security execution.

* * * * *